United States Patent
Smith et al.

(10) Patent No.: US 12,076,483 B2
(45) Date of Patent: *Sep. 3, 2024

(54) PORTABLE APPARATUS FOR PROVIDING CHEST THERAPY

(71) Applicants: Brett Gene Smith, Canby, OR (US); Exemplar Medical LLC, Olathe, KS (US)

(72) Inventors: Brett Gene Smith, Canby, OR (US); Erica Renae Cusumano, Kansas City, MO (US); Christian Scott Moore, Las Vegas, NV (US); David Warner, Overland Park, KS (US)

(73) Assignee: Exemplar Medical LLC, Olathe, KS (US)

( * ) Notice: Subject to any disclaimer, the term of this patent is extended or adjusted under 35 U.S.C. 154(b) by 648 days.

This patent is subject to a terminal disclaimer.

(21) Appl. No.: 17/215,779

(22) Filed: Mar. 29, 2021

(65) Prior Publication Data
US 2021/0213216 A1 Jul. 15, 2021

Related U.S. Application Data

(63) Continuation-in-part of application No. 15/872,459, filed on Jan. 16, 2018, now Pat. No. 10,959,912, (Continued)

(51) Int. Cl.
*A61M 16/00* (2006.01)
*A61H 23/02* (2006.01)

(52) U.S. Cl.
CPC ..... *A61M 16/0006* (2014.02); *A61H 23/0263* (2013.01); *A61H 2205/084* (2013.01)

(58) Field of Classification Search
CPC ........ A61H 23/00–04; A61H 2023/045; A61H 11/00–02; A61H 2201/1619–1621;
(Continued)

(56) References Cited

U.S. PATENT DOCUMENTS

| | | |
|---|---|---|
| 3,896,795 A | 7/1975 | Solhkhah |
| 4,838,263 A | 6/1989 | Warwick et al. |

(Continued)

FOREIGN PATENT DOCUMENTS

| | | |
|---|---|---|
| CA | 2819683 C | 8/2018 |
| CA | 3010192 C | 1/2020 |

(Continued)

OTHER PUBLICATIONS

International Search Report and Written Opinion received for PCT Patent Application No. PCT/US2022/022259, mailed on Jul. 6, 2022, 9 pages.

(Continued)

*Primary Examiner* — Rachel T Sippel
(74) *Attorney, Agent, or Firm* — Shook, Hardy & Bacon L.L.P.

(57) ABSTRACT

An apparatus includes an elongated band having a first terminal end, a second terminal end, a top surface, and a bottom surface. A plurality of openings extend through the top surface and the bottom surface of the band. A plurality of moveable vibrating elements are coupled to the band at the plurality of openings. A plurality of moveable covers are also coupled to the band. Each of the covers encloses an internal cavity configured to receive one or more of the moveable vibrating elements. A releasable connection assembly includes a first terminal-end connector coupled to the first terminal end of the band and a second terminal-end connector coupled to the second terminal end of the elongated band. The second terminal-end connector is releasably connectable to the first terminal-end connector.

18 Claims, 55 Drawing Sheets

Related U.S. Application Data which is a continuation-in-part of application No. 14/563,644, filed on Dec. 8, 2014, now Pat. No. 9,901,510.

(60) Provisional application No. 61/913,409, filed on Dec. 9, 2013.

(58) Field of Classification Search
CPC ...... A61H 2201/165; A61H 2201/5002; A61H 2201/501; A61M 2205/05
See application file for complete search history.

(56) References Cited

U.S. PATENT DOCUMENTS

| | | |
|---|---|---|
| 4,977,889 A | 12/1990 | Budd |
| 5,056,505 A | 10/1991 | Warwick et al. |
| 5,569,170 A | 10/1996 | Hansen |
| 5,769,797 A | 6/1998 | Van Brunt et al. |
| 5,970,526 A | 10/1999 | Weathers |
| 6,030,353 A | 2/2000 | Van Brunt |
| 6,036,662 A | 3/2000 | Van Brunt et al. |
| 6,155,996 A | 12/2000 | Van Brunt et al. |
| 6,234,985 B1 | 5/2001 | Lurie et al. |
| 6,350,249 B1 | 2/2002 | Zicherman |
| D456,591 S | 5/2002 | Hansen |
| D461,897 S | 8/2002 | Hansen et al. |
| 6,547,749 B2 | 4/2003 | Hansen |
| 6,605,050 B2 | 8/2003 | Hansen |
| 6,676,613 B2 | 1/2004 | Cantrell et al. |
| 6,676,614 B1 | 1/2004 | Hansen et al. |
| 6,736,785 B1 | 5/2004 | Van Brunt |
| 6,916,298 B2 | 7/2005 | VanBrunt et al. |
| 6,958,047 B2 | 10/2005 | DeVlieger |
| 7,018,348 B2 | 3/2006 | Van Brunt et al. |
| 7,041,072 B2 | 5/2006 | Calvert |
| 7,316,658 B2 | 1/2008 | Gagne |
| 7,347,832 B2 | 3/2008 | Jensen et al. |
| 7,374,550 B2 | 5/2008 | Hansen et al. |
| 7,416,536 B2 | 8/2008 | DeVlieger |
| 7,497,837 B2 | 3/2009 | Sherman et al. |
| RE40,814 E | 6/2009 | Van Brunt et al. |
| 7,618,384 B2 | 11/2009 | Nardi et al. |
| 7,736,325 B2 | 6/2010 | Tung et al. |
| 7,762,967 B2 | 7/2010 | Warwick et al. |
| 7,785,280 B2 | 8/2010 | Kivisto |
| 7,895,690 B2 | 3/2011 | Kovalyak |
| D639,954 S | 6/2011 | Helgeson et al. |
| 8,010,190 B2 | 8/2011 | Olson et al. |
| 8,060,199 B2 | 11/2011 | Walker et al. |
| 8,092,406 B2 | 1/2012 | Gorsen |
| 8,121,681 B2 | 2/2012 | Hampton et al. |
| 8,192,381 B2 | 6/2012 | Nozzarella |
| 8,202,237 B2 | 6/2012 | Helgeson et al. |
| 8,226,583 B2 | 7/2012 | Keler et al. |
| 8,298,165 B2 | 10/2012 | Sherman et al. |
| RE44,187 E | 4/2013 | Marcovecchio et al. |
| 8,408,204 B2 | 4/2013 | Lurie |
| 8,460,223 B2 | 6/2013 | Huster et al. |
| 8,540,653 B2 | 9/2013 | Baldauf et al. |
| 8,663,138 B2 | 3/2014 | Huster et al. |
| 8,708,937 B2 | 4/2014 | Van Brunt et al. |
| 8,734,370 B1 | 5/2014 | Ignagni |
| 8,740,824 B2 | 6/2014 | Hansen et al. |
| 8,845,562 B2 | 9/2014 | Receveur et al. |
| 8,845,564 B2 | 9/2014 | Cascini et al. |
| 8,868,180 B2 | 10/2014 | Bystrom et al. |
| 8,870,796 B2 | 10/2014 | Hoffmann |
| 8,900,168 B2 | 12/2014 | Yamashiro et al. |
| 9,549,869 B2 | 1/2017 | DeVlieger et al. |
| 9,572,743 B2 | 2/2017 | Keler et al. |
| 9,744,097 B2 | 8/2017 | DeVlleger et al. |
| 9,968,511 B2 | 5/2018 | Huster et al. |
| 10,016,325 B2 | 7/2018 | Ribble et al. |
| 10,238,560 B2 | 3/2019 | O'Keefe et al. |
| 10,292,890 B2 | 5/2019 | DeVliegar et al. |
| 10,363,183 B2 | 7/2019 | Ribble et al. |
| 2003/0163176 A1* | 8/2003 | Bae .................. A61H 39/04 607/96 |
| 2004/0097850 A1 | 5/2004 | Plante |
| 2004/0176709 A1 | 9/2004 | Van Brunt |
| 2005/0059909 A1 | 3/2005 | Burgess |
| 2005/0113725 A1 | 5/2005 | Masuda |
| 2005/0234373 A1 | 10/2005 | Khalaf |
| 2007/0246045 A1 | 10/2007 | Hoffman |
| 2008/0021355 A1 | 1/2008 | Huster et al. |
| 2008/0027363 A1 | 1/2008 | Brueckmann et al. |
| 2008/0319359 A1* | 12/2008 | Moomiaie-Qajar ... A61H 11/00 601/152 |
| 2009/0192421 A1 | 7/2009 | Huster et al. |
| 2012/0022415 A1 | 1/2012 | Mullen et al. |
| 2012/0035515 A1 | 2/2012 | Ng |
| 2013/0085426 A1 | 4/2013 | Brodsky |
| 2013/0226255 A1 | 8/2013 | Chapman et al. |
| 2013/0261518 A1 | 10/2013 | Hansen et al. |
| 2013/0267877 A1 | 10/2013 | Van Brunt |
| 2013/0289456 A1 | 10/2013 | Chang Guo et al. |
| 2013/0331747 A1 | 12/2013 | Helgeson et al. |
| 2014/0012167 A1 | 1/2014 | Devlieger et al. |
| 2014/0024979 A1 | 1/2014 | Radbourne |
| 2014/0171843 A1 | 6/2014 | Huster et al. |
| 2014/0257151 A1 | 9/2014 | Chikkanaravangala et al. |
| 2014/0257153 A1 | 9/2014 | Nickelson |
| 2014/0276271 A1 | 9/2014 | Stryker et al. |
| 2015/0025425 A1 | 1/2015 | Mitchell |
| 2015/0173569 A1 | 6/2015 | Griggs |
| 2015/0224019 A1 | 8/2015 | Barbera |
| 2016/0331620 A1 | 11/2016 | Kazanchyan et al. |
| 2017/0119620 A1 | 5/2017 | Trapp |
| 2018/0049939 A1 | 2/2018 | Bobey et al. |
| 2018/0228687 A1 | 8/2018 | Huster et al. |
| 2019/0167502 A1 | 6/2019 | DeVlieger et al. |
| 2019/0290534 A1 | 9/2019 | Lazarides et al. |
| 2020/0100981 A1 | 4/2020 | Bobey et al. |

FOREIGN PATENT DOCUMENTS

| | | |
|---|---|---|
| EP | 1932501 A2 | 6/2008 |
| EP | 2777678 A1 | 9/2014 |
| EP | 2910233 A2 | 8/2015 |
| EP | 3103428 B1 | 3/2020 |
| JP | 4828513 B2 | 11/2011 |

OTHER PUBLICATIONS

"AffloVest, Answering Needs: The Role of the AffloVest in the Respiratory Market", International Biophysics Corporation: AffloVest White Paper, Retrieved from Internet URL : http://www.afflovest.com/wp-content/uploads/2013/06/White-Paper-on-AffloVest.pdf, accessed on Mar. 17, 2015, p. 12.

Bach, J. R., "Mechanical Exsufflation, Noninvasive Ventilation, and New Strategies for Pulmonary Rehabilitation and Sleep Disordered Breathing", Bull. N. Y. Acad. Med, vol. 68, No. 2, pp. 321-340 (Mar.-Apr. 1992).

Braverman, J. M., "Airway Clearance Needs in Duchenne Muscular Dystrophy: An Overview", Advanced Respiratory, pp. 8 (2001).

Ciesla, N. D., "Chest Physical Therapy for Patients in the Intensive Care Unit", Physical Therapy, vol. 76, No. 6, pp. 609-625 (Jun. 1996).

Mehta, S., and Hill, N. S., "Noninvasive Ventilation—State of the Art", American Journal of Respiratory and Critical Care Medicine, vol. 163, pp. 540-577 (2001).

International Preliminary Report on Patentability received for PCT Patent Application No. PCT/US2022/022259, mailed on Oct. 12, 2023, 8 pages.

* cited by examiner

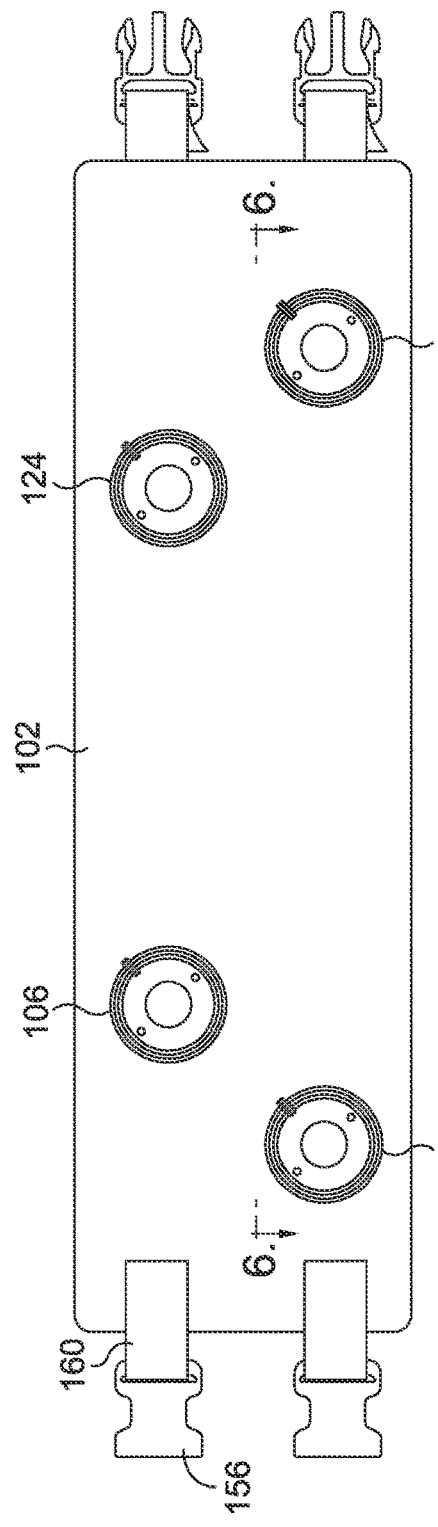
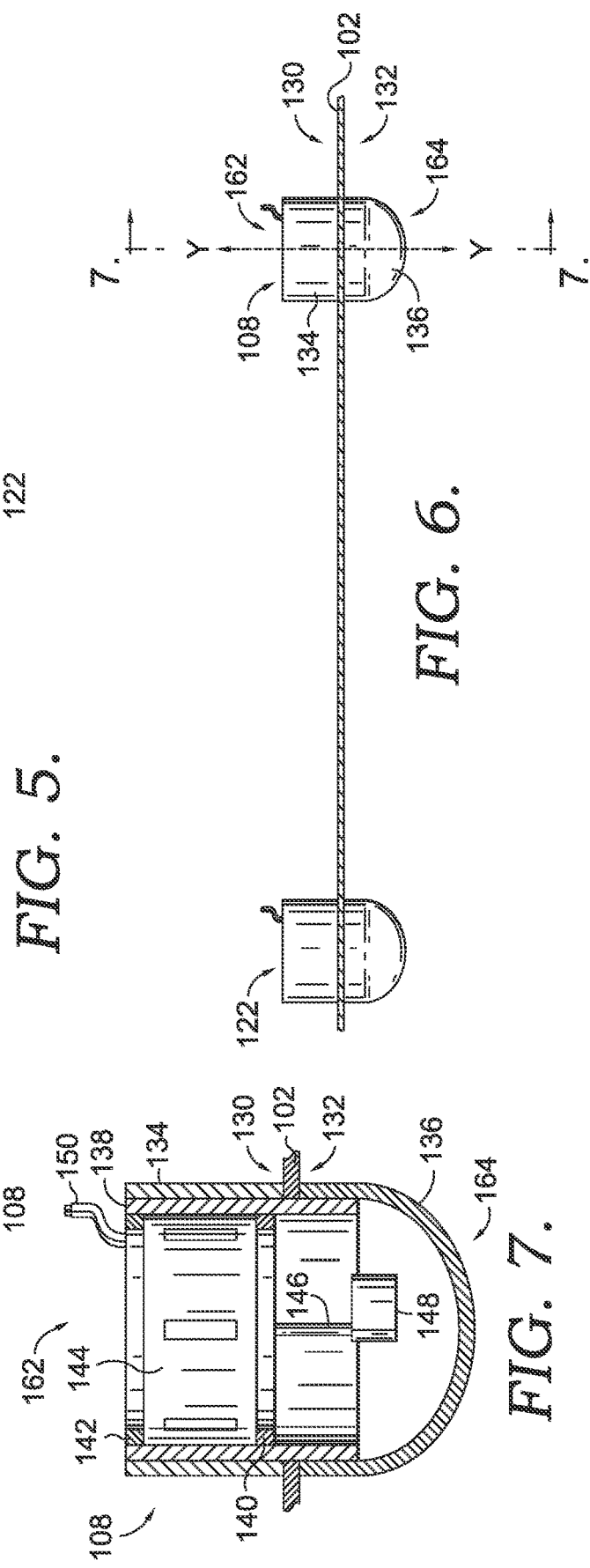

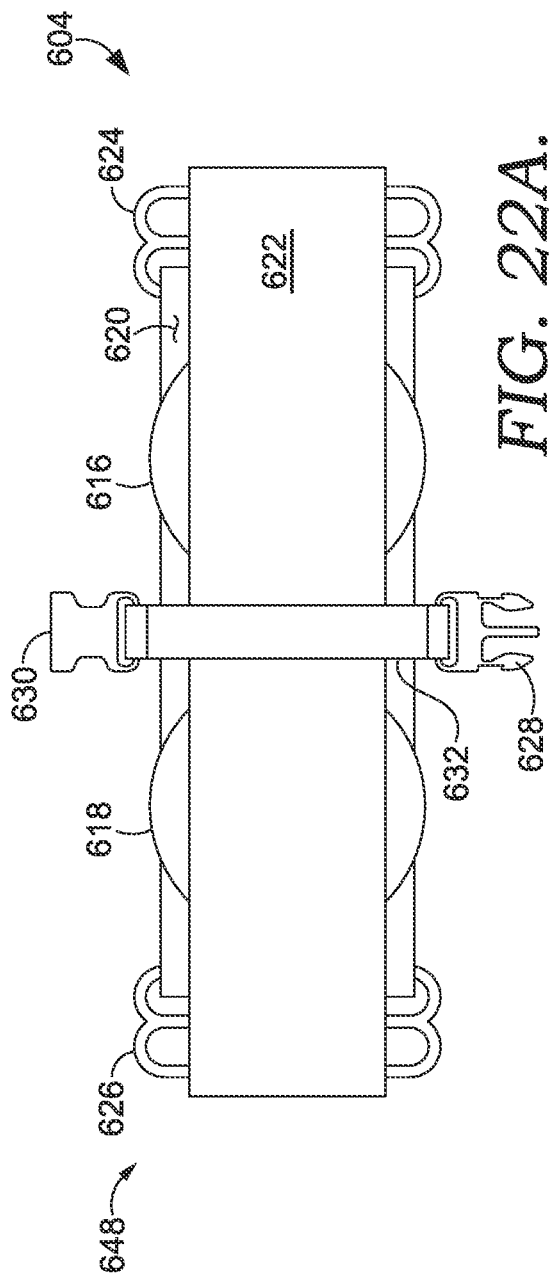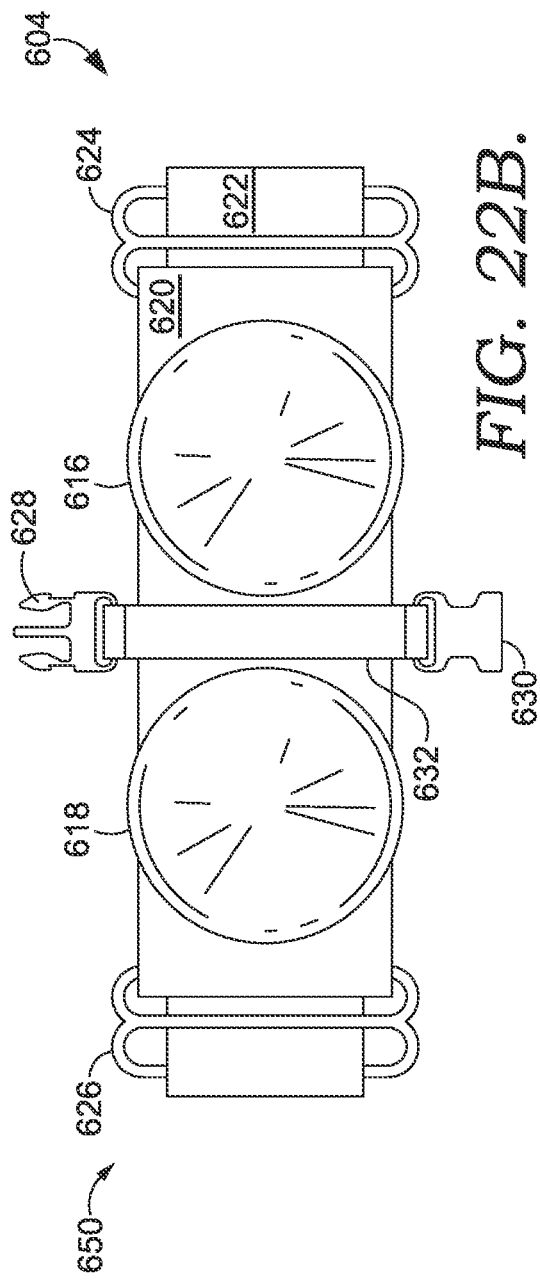

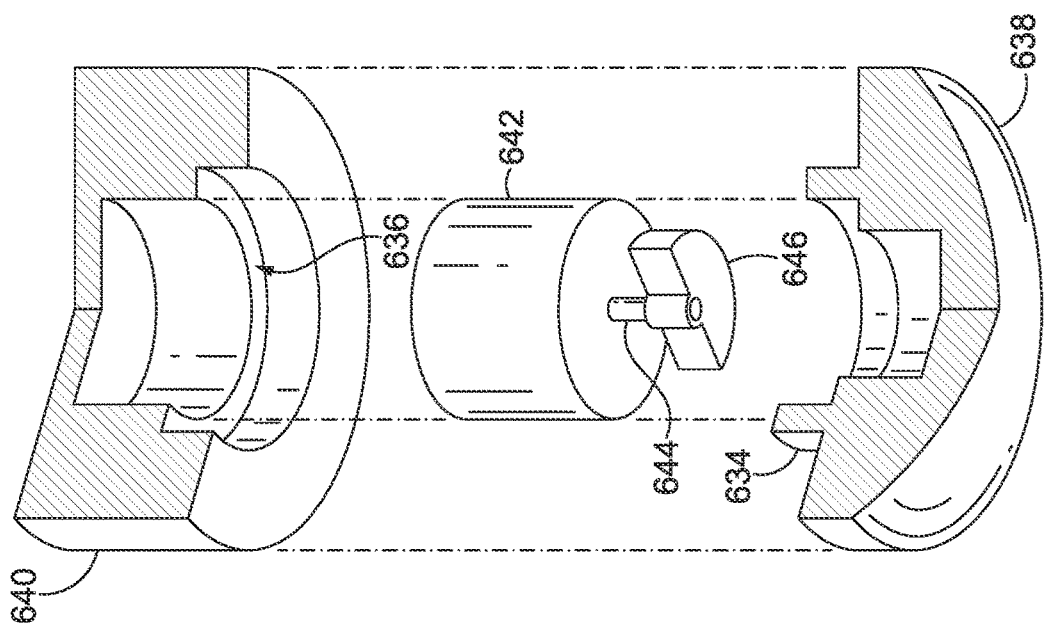
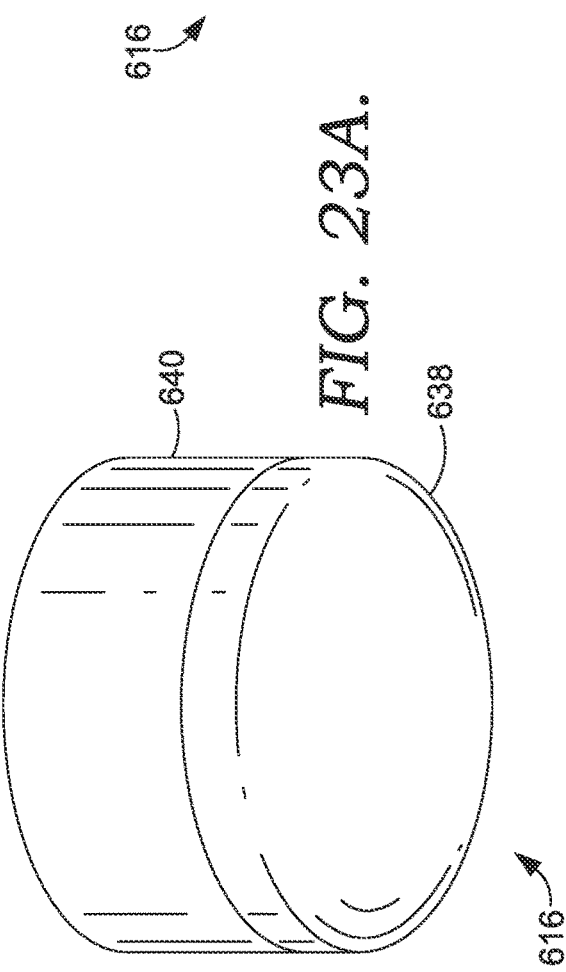
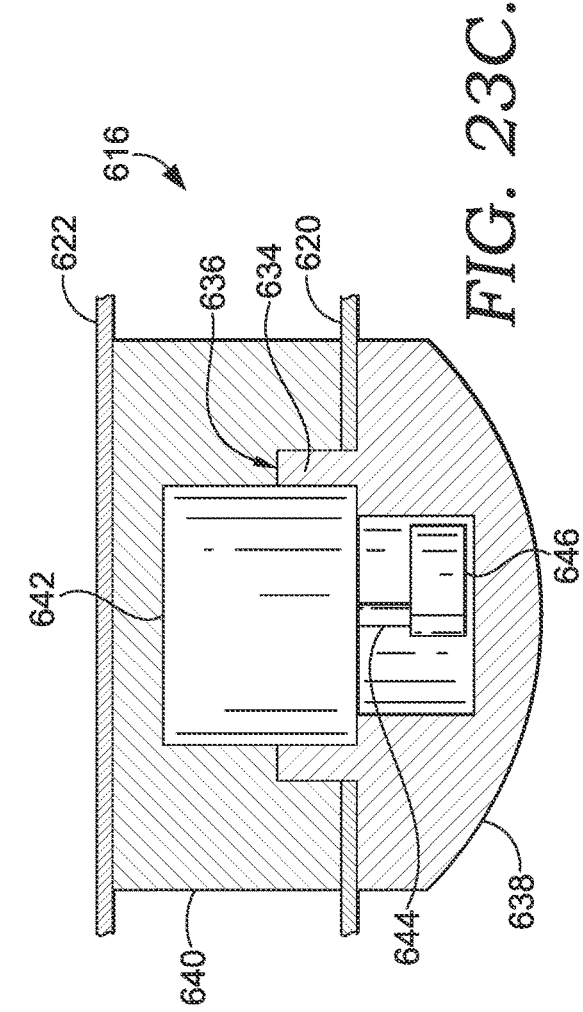

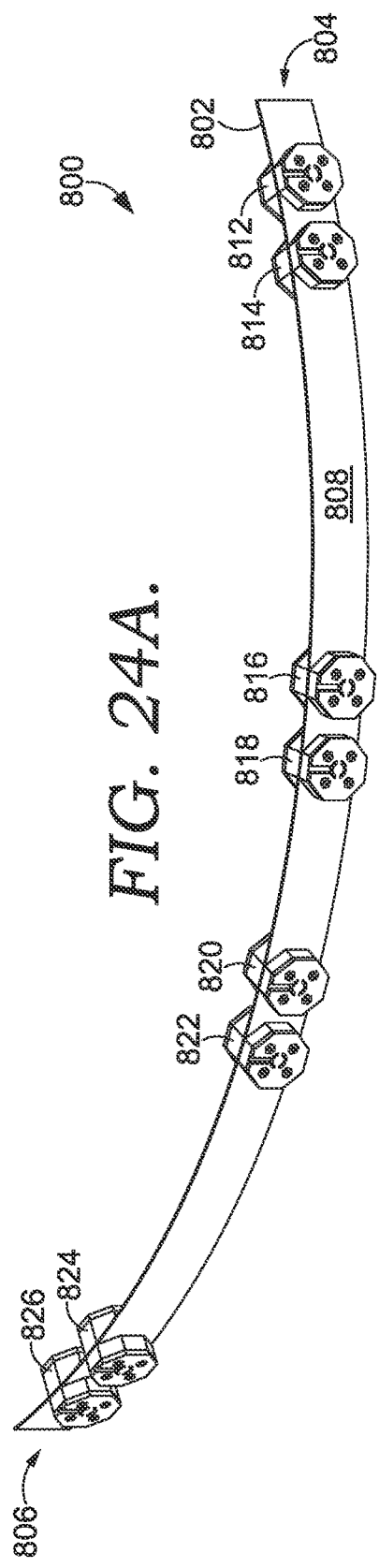
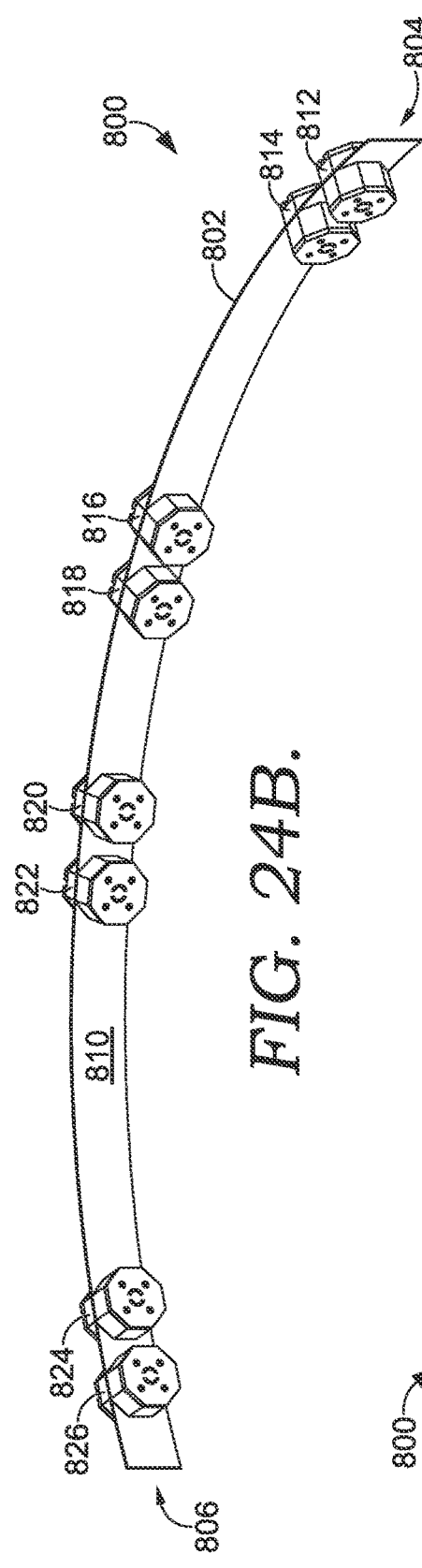
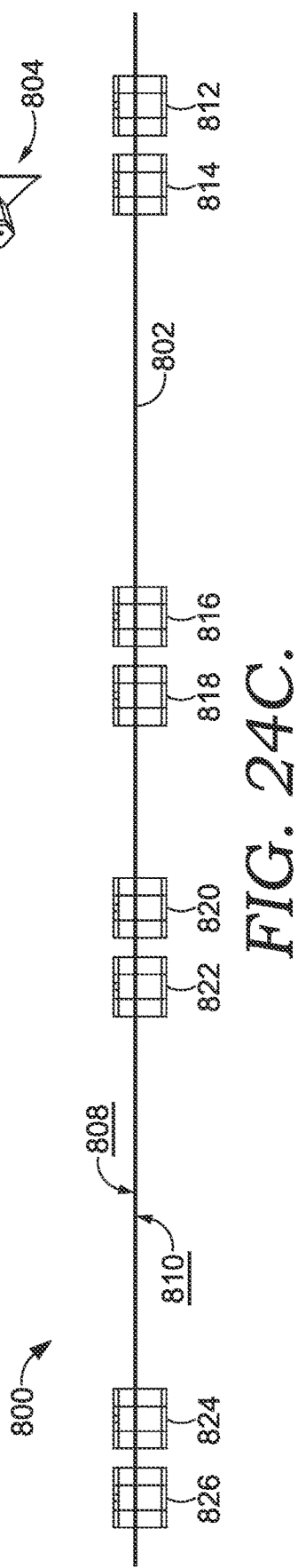
FIG. 24A.
FIG. 24B.
FIG. 24C.

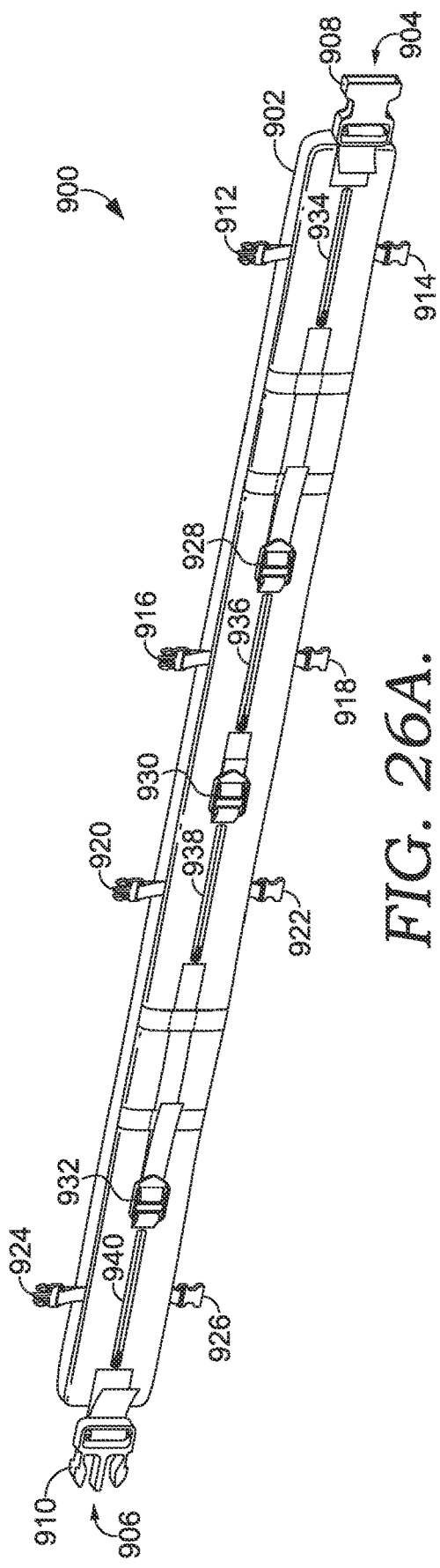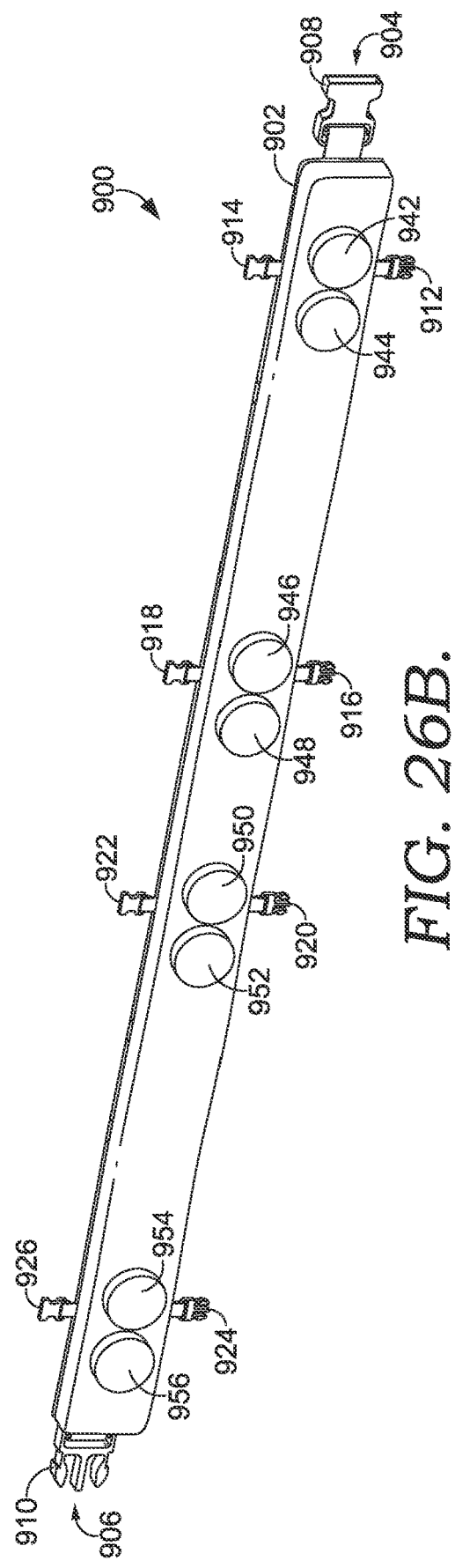

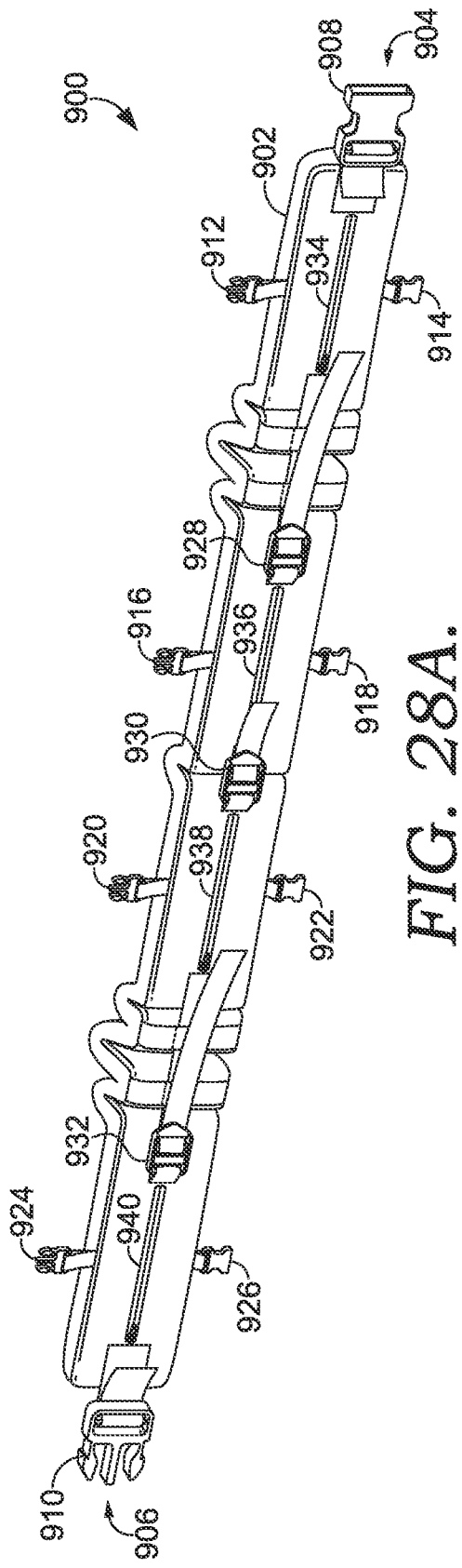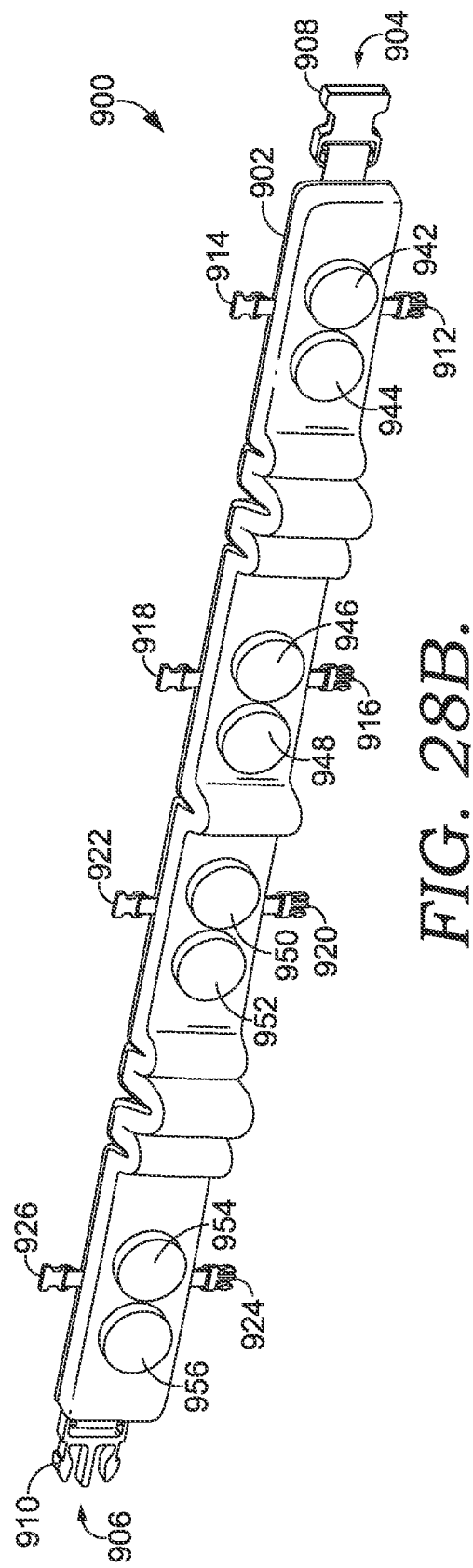

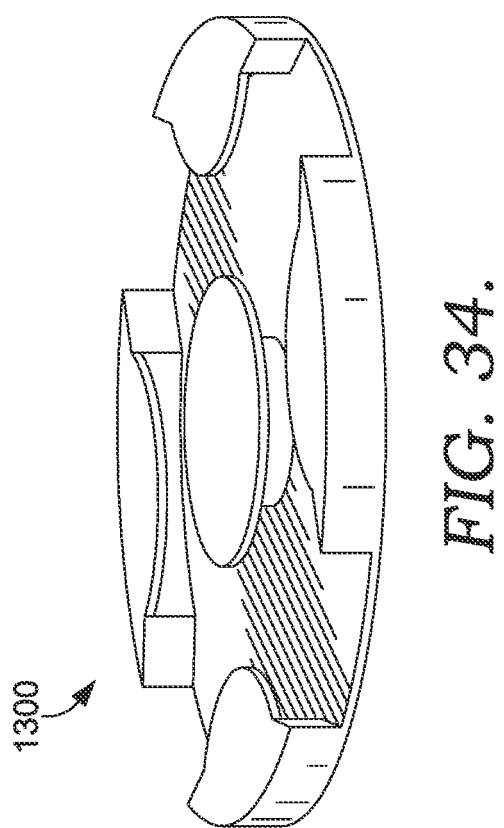

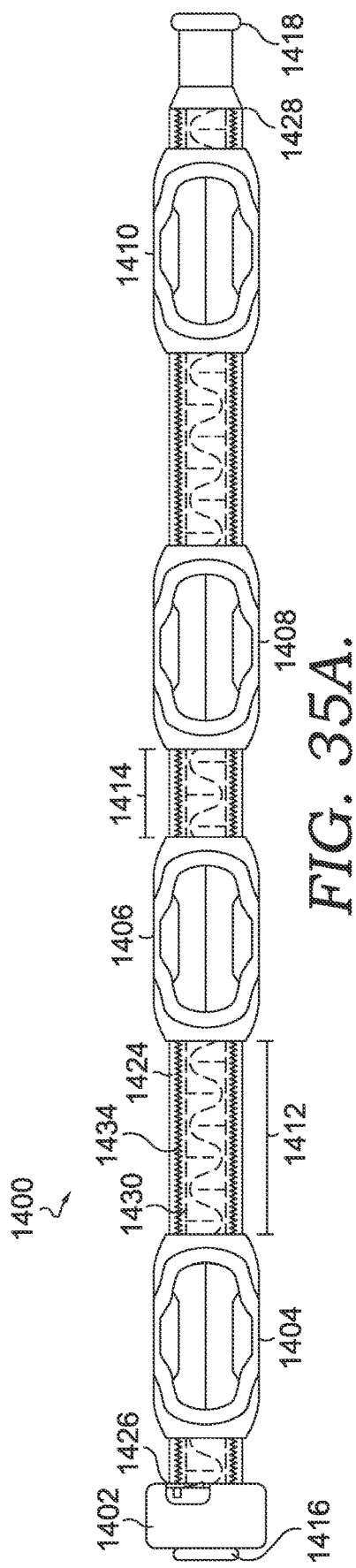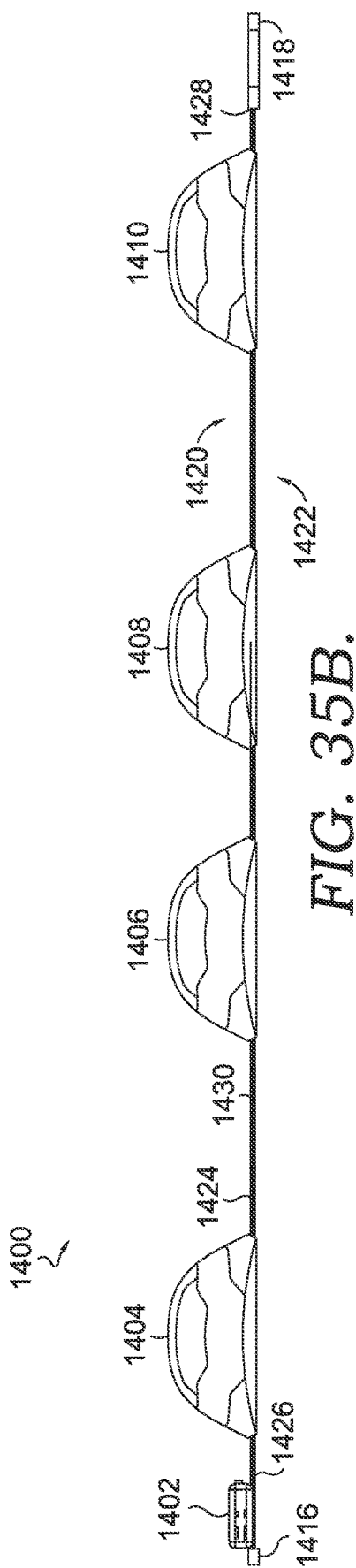

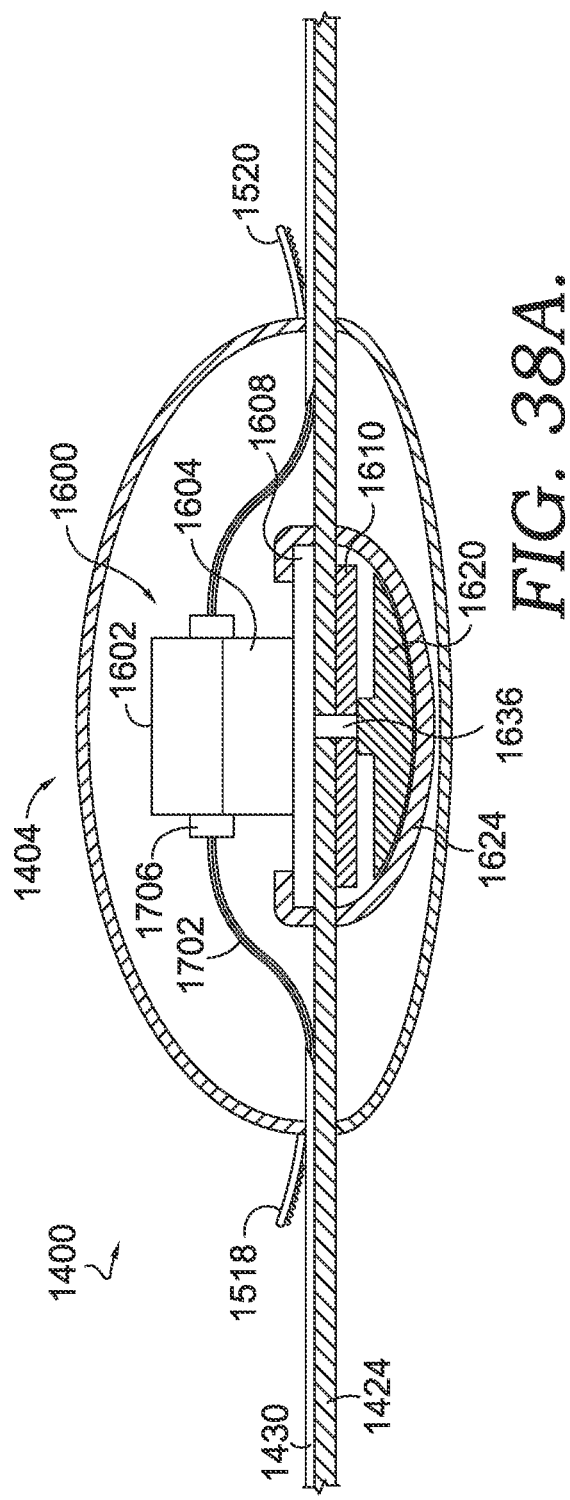
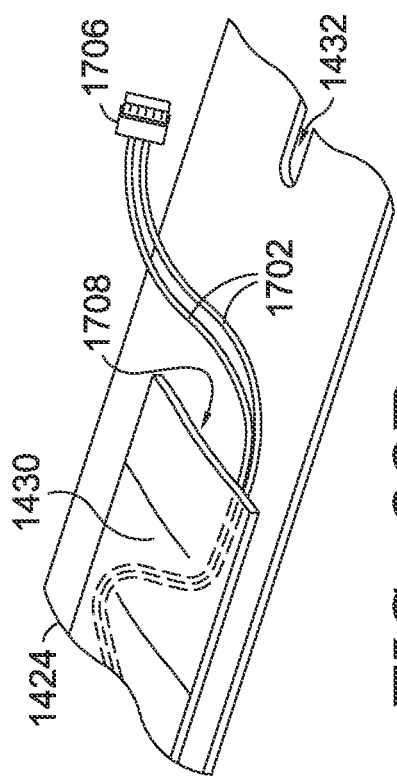
FIG. 38A.
FIG. 38B.

PORTABLE APPARATUS FOR PROVIDING CHEST THERAPY

CROSS-REFERENCE TO RELATED APPLICATIONS

This patent application is a continuation-in-part of pending U.S. application Ser. No. 15/872,459, filed on Jan. 16, 2018, and entitled "Portable Apparatus for Providing Chest Therapy," which is a continuation-in-part of U.S. application Ser. No. 14/563,644, filed on Dec. 8, 2014, and entitled "Portable Apparatus for Providing Chest Therapy," which claims the benefit of U.S. Provisional Application Ser. No. 61/913,409, filed on Dec. 9, 2013, and entitled, "Mobile Percussion Airway Clearance System." The entirety of the disclosures of each of U.S. application Ser. No. 15/872,459, U.S. application Ser. No. 14/563,644, and U.S. Provisional Application Ser. No. 61/913,409 is hereby incorporated by reference.

BACKGROUND

Individuals having certain medical conditions may undergo chest physical therapy to aid with lung drainage and airway clearance. Such medical conditions include cystic fibrosis, bronchiectasis, neuromuscular diseases (e.g., Guillain-Barré syndrome), progressive muscle weakness (e.g., myasthenia gravis), and tetanus. Individuals having lung diseases, such as pneumonia, bronchitis, and certain forms of chronic obstructive pulmonary disease ("COPD"), including chronic bronchitis, may also benefit from chest physical therapy.

SUMMARY

This Summary is provided to introduce a selection of concepts in a simplified form that are further described below in the Detailed Description. This Summary is not intended to identify key features or essential features of the claimed subject matter, nor is it intended to be used as an aid in isolation to determine the scope of the claimed subject matter. Embodiments of the invention are defined by the claims below, not this Summary.

In brief and at a high level this disclosure describes, among other things, a portable apparatus for providing therapy, such as chest physical therapy to a user. In one example, the portable apparatus may include a chest band having one or more vibrating elements coupled thereto. When the chest band is worn by a user, the vibrating elements may be positioned adjacent to the user's chest and/or thorax in order to provide a vibrational force to various portions of the user's chest and/or thorax. This vibrational force may, among other things, improve lung drainage, mobilize lung secretions, and promote airway clearance.

DESCRIPTION OF THE DRAWINGS

The present disclosure makes reference to the attached drawing figures, wherein:

FIG. 5 is a plan view of a top surface of an exemplary chest band segment, in accordance with an exemplary embodiment hereof;

FIG. 6 is a cross-section view of the exemplary chest band segment of FIG. 5, in accordance with an exemplary embodiment hereof;

FIG. 7 is an enlarged, cross-section view of an exemplary vibrating element of FIG. 6, in accordance with an exemplary embodiment hereof;

FIGS. 22A-B are plan views of a top and bottom surface, respectively, of an exemplary chest band segment including vibrating elements, in accordance with an exemplary embodiment hereof;

FIG. 23A is a perspective view of an exemplary vibrating element, in accordance with an exemplary embodiment hereof;

FIG. 23B is an exploded cutaway view of an exemplary vibrating element, in accordance with an exemplary embodiment hereof;

FIG. 23C is a cross-section view of the exemplary chest band segment of FIG. 22C, in accordance with an exemplary embodiment hereof;

FIGS. 24A-B are front and rear, perspective views, respectively, of an exemplary vibration band, in accordance with an exemplary embodiment hereof;

FIG. 24C is a side elevation view of the exemplary vibration band of FIGS. 24A-B, in accordance with an exemplary embodiment hereof;

FIGS. 26A-B are front and rear, perspective views, respectively, of an exemplary apparatus unit, in accordance with an exemplary embodiment hereof;

FIGS. 28A-B are front and rear, perspective views, respectively, of the exemplary apparatus unit of FIGS. 26A-B after its length has been adjusted, in accordance with an exemplary embodiment hereof;

FIG. 34 is a perspective view of an exemplary positioning mechanism, in accordance with an exemplary embodiment hereof;

FIG. 35A is a plan view of a top surface of an exemplary vibration band including covers that enclose one or more vibrating elements, in accordance with an exemplary embodiment hereof;

FIG. 35B is a side view of the exemplary vibration band of FIG. 35A, in accordance with an exemplary embodiment hereof;

FIG. 38A is a cross-section view of a cover coupled to a vibration band, in accordance with an exemplary embodiment hereof;

FIG. 38B is a top, perspective view of a wire tunnel coupled to a vibration band, in accordance with an exemplary embodiment hereof;

DETAILED DESCRIPTION

Figure 1:
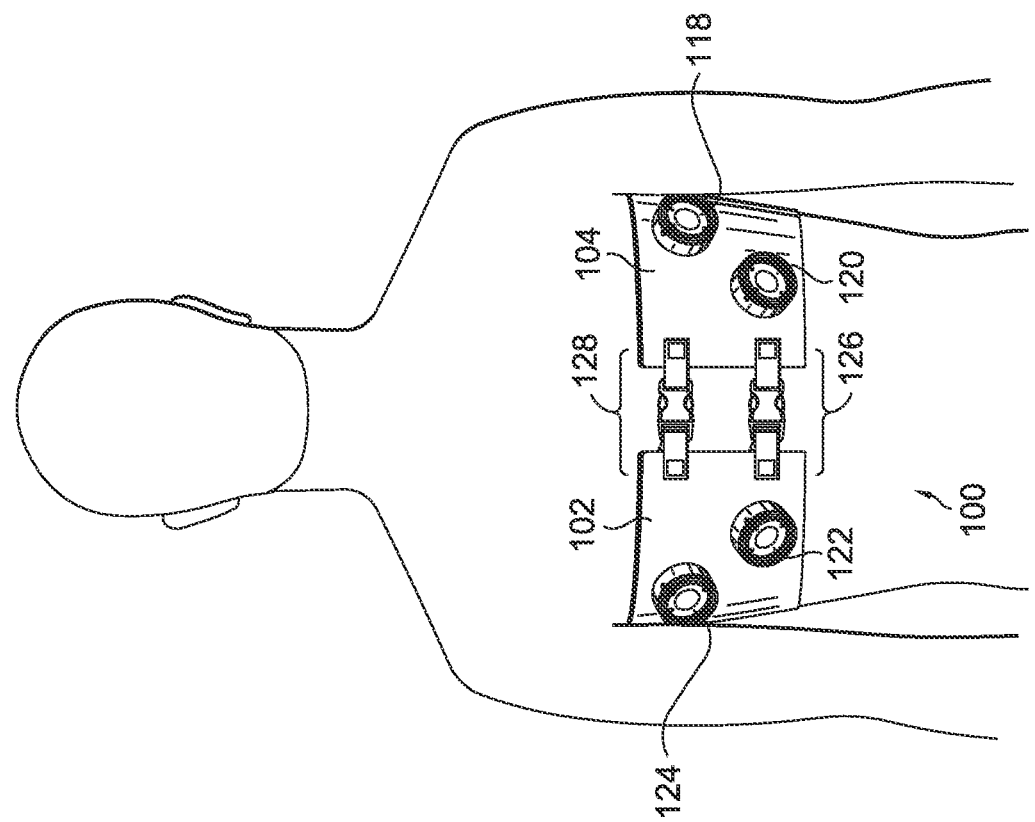
FIG. 1 is a front, perspective view of an exemplary chest band including vibrating elements, where the exemplary chest band is being worn by a user, in accordance with an exemplary embodiment hereof.

The subject matter of select embodiments may be described with specificity to meet statutory requirements. But the description itself is not intended to necessarily limit the scope of the claims. Rather, the claimed subject matter might be embodied in other ways to include different components, steps, or combinations thereof similar to the ones described in this document, in conjunction with other present or future technologies. Terms should not be interpreted as implying any particular order among or between various steps disclosed herein unless and except when the order of individual steps is explicitly described.

For purposes of this disclosure, the word "including" has the same broad meaning as the word "comprising." In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

Embodiments of the invention include a portable apparatus for providing therapy, such as chest physical therapy, to a user. The therapy provided by the apparatus may improve lung drainage, mobilize lung secretions, and promote airway clearance. Exemplary embodiments of the invention may be described as a "Mobile Percussion Airway Clearance System" or "MPACS."

Individuals having certain medical conditions and/or diseases may benefit from the chest therapy provided by the features described herein. Such medical conditions include cystic fibrosis, bronchiectasis, neuromuscular diseases (e.g., Guillain-Barré syndrome), progressive muscle weakness (e.g., myasthenia gravis), and tetanus. Individuals having lung diseases, such as pneumonia, bronchitis, and certain forms of COPD, including chronic bronchitis, may also benefit from chest physical therapy provided by the features described herein.

While the present disclosure focuses on chest physical therapy (which may be referred to herein as "chest therapy"), it will be understood by those having skill in the relevant art that the features described herein could be used for various other forms of physical therapy. Such other forms of physical therapy are included within the scope hereof.

An exemplary embodiment described herein may provide high-frequency chest wall percussions by way of a chest band including one or more vibrating elements. When the chest band is worn by a user, the vibrating elements may be positioned adjacent to the user's chest and/or thorax in order to provide a vibrational force to various portions of the user's chest and/or thorax. It is this force that may, among other things, improve lung drainage, mobilize lung secretions, and promote airway clearance.

A significant advantage of the portable apparatus including the features described herein is that it maximizes the mobility of the user while the user engages in a chest therapy session provided by the apparatus. To this end, the apparatus may be lightweight and portable. Accordingly, the user may engage in a chest therapy session provided by the apparatus while simultaneously participating in daily activities, such as cooking, walking, driving, cleaning, yard work, playing, and the like. The user may also engage in a chest therapy session provided by the apparatus while simultaneously participating in relatively strenuous activities, such as running, hiking, bike riding, exercising, and the like. Any encumbrance to the user during such daily and relatively strenuous activities is minimal. And because the apparatus is lightweight, portable, convenient, and comfortable, the user is likely to engage in chest therapy sessions more often than the user would if the user was required to use other devices that are heavier and more restrictive. Furthermore, the ability to exercise while engaging in a chest therapy session may provide particular advantages. For example, the chest therapy session might improve the user's ability to breath during exercise, thereby enhancing the user's exercise experience.

In one exemplary embodiment, the apparatus may include a wearable pack, where the wearable pack may be used to store and transport all components needed for chest therapy, as well as other types of therapy and/or treatment, such as nebulizer treatments. Even with these additional components, the apparatus may weigh approximately 8 pounds or less. Again, this enhanced mobility provides numerous benefits. For example, the user may easily carry the apparatus with him wherever he goes. The user need not return home (or to some other fixed location) in order to engage in a chest therapy and/or nebulizer treatment session. The user may maintain a physically and/or socially active schedule while also obtaining the benefits of frequent chest therapy sessions and nebulizer treatments. The apparatus may thereby provide psychological benefits due to significant lifestyle improvements.

A number of features provide the mobility advantages mentioned above. As already described, the apparatus may be lightweight and portable. Additionally, a portable power source, such as batteries, may be used to power the apparatus. As will be discussed in more detail below, a configuration of vibrating elements may maximize user mobility and minimize any physical interference caused by the apparatus. Additionally, a chest band may be comprised, at least in part, of elastic materials, thereby allowing a user to breathe normally during a chest therapy session. This exemplary feature, among others, allows a user to engage in strenuous activities that may result in heavy breathing while wearing the chest band.

Notably, exemplary embodiments hereof do not rely on pneumatic forces to provide chest therapy to a user. This may be advantageous, because the equipment required to provide such pneumatic force may be heavy, cumbersome, and power intensive.

This discussion of exemplary advantages is illustrative only and is not intended to be limiting. Based on the present disclosure, it will be understood that additional advantages are provided by a portable apparatus for providing therapy, as described herein.

Exemplary embodiments hereof include a portable apparatus for providing chest therapy to a user. The portable apparatus may include a wearable pack. A chest band including one or more chest band segments may be coupled to the wearable pack. The wearable pack may be configured to be worn around a chest of the user. A plurality of vibrating elements may be coupled to the one or more chest band segments. The plurality of vibrating elements may provide a vibrational force to the chest of the user when the chest band is worn around the chest of the user. The portable apparatus may further include a nebulizer treatment component coupled to the wearable pack. A user input component may be provided for receiving a user input regarding an operation of one or more of the nebulizer treatment component or the plurality of vibrating elements. The user input component may be electrically coupled to the plurality of vibrating elements and the nebulizer treatment component.

An additional embodiment includes a portable apparatus for providing chest therapy to a user. The portable apparatus may include a chest band segment including a top surface parallel to an opposite bottom surface. The bottom surface of the chest band segment may be configured to be positioned adjacent to a body of the user. A plurality of vibrating elements may be coupled to the chest band segment, where each of the plurality of vibrating elements provides a vibrational force.

Yet another embodiment provides an article of manufacture that includes a panel having a top surface that is parallel to an opposite bottom surface. The bottom surface may be configured to be positioned adjacent to a body of a user. A vibrating element may be coupled to the panel, where the vibrating element provides a vibrational force.

Another embodiment includes an apparatus comprising a vibration band, which includes an elongated band comprising a band first terminal end and a band second terminal end. One or more vibrating elements are disposed between the band first terminal end and the band second terminal end. An elongated cover that comprises a cover first terminal end and a cover second terminal end encloses the vibration band. The elongated cover includes a releasable connection assembly, which includes a first terminal-end connector that is coupled to the cover first terminal end and a second terminal-end connector that is coupled to the cover second terminal end and that is releasably connectable to the first terminal-end connector. The elongated cover further includes one or more interspaced connectors disposed between the cover first terminal end and the cover second terminal end.

An additional embodiment includes an apparatus comprising a vibration band and an elongated cover that encloses the vibration band. The vibration band includes a band that has a band first terminal end and a band second terminal end. One or more vibrating elements are disposed between the band first terminal end and the band second terminal end. The elongated cover includes one or more pockets, each of which is configured to receive a respective one of the one or more vibrating elements.

Yet another embodiment includes an apparatus comprising a vibration band and an elongated cover that encloses the vibration band. The vibration band includes an elongated chest band having a band first terminal end and a band second terminal end. One or more vibrating elements are disposed between the band first terminal end and the band second terminal end. The elongated cover includes a cover first terminal end and a cover second terminal end. The cover further includes a releasable connection assembly, which includes a first terminal-end connector that is coupled to the cover first terminal end and a second terminal-end connector that is coupled to the cover second terminal end and that is releasably connectable to the first terminal-end connector. The cover also includes one or more interspaced connectors disposed between the cover first terminal end and the cover second terminal end. Additionally, the cover includes one or more pockets, each of which is configured to receive a respective one of the one or more vibrating elements.

In another embodiment, an apparatus comprises an elongated band having a first terminal end, a second terminal end opposite the first terminal end, a top surface, a bottom surface opposite the top surface, and a plurality of openings extending through the top surface and the bottom surface of the elongated band. A plurality of moveable vibrating elements are coupled to the elongated band at the plurality of openings. A plurality of moveable covers are coupled to the elongated band. Each of the plurality of covers encloses an internal cavity configured to receive one or more of the plurality of moveable vibrating elements. A releasable connection assembly includes a first terminal-end connector coupled to the first terminal end and a second terminal-end connector coupled to the second terminal end of the first elongated band. The second terminal-end connector is releasably connectable to the first terminal-end connector.

In an additional embodiment, an apparatus comprises a band having a first terminal end, a second terminal end opposite the first terminal end, a top surface, a bottom surface opposite the top surface, and one or more openings disposed between the first terminal end and the second terminal end. The apparatus further includes one or more moveable vibrating elements coupled to the band at the one or more openings, as well as one or more moveable covers coupled to the band. Each of the one or more moveable covers encloses an internal cavity configured to receive a moveable vibrating element of the one or more moveable vibrating elements.

In yet another embodiment, an apparatus includes a first vibration band and a second vibration band. The first vibration band includes a first elongated band comprising one or more elongated openings disposed along a length of the first elongated band, as well as one or more moveable vibrating elements coupled to the first elongated band at the one or more elongated openings. The second vibration band includes a second elongated band comprising one or more elongated openings disposed along a length of the second elongated band, as well as one or more moveable vibrating elements coupled to the second elongated band at the one or more elongated openings.

With reference now to the figures, components included in a portable apparatus for providing chest therapy to a user are described in accordance with embodiments of the invention. Various embodiments are described with respect to the figures in which like elements are depicted with like reference numerals.

Figure 2:
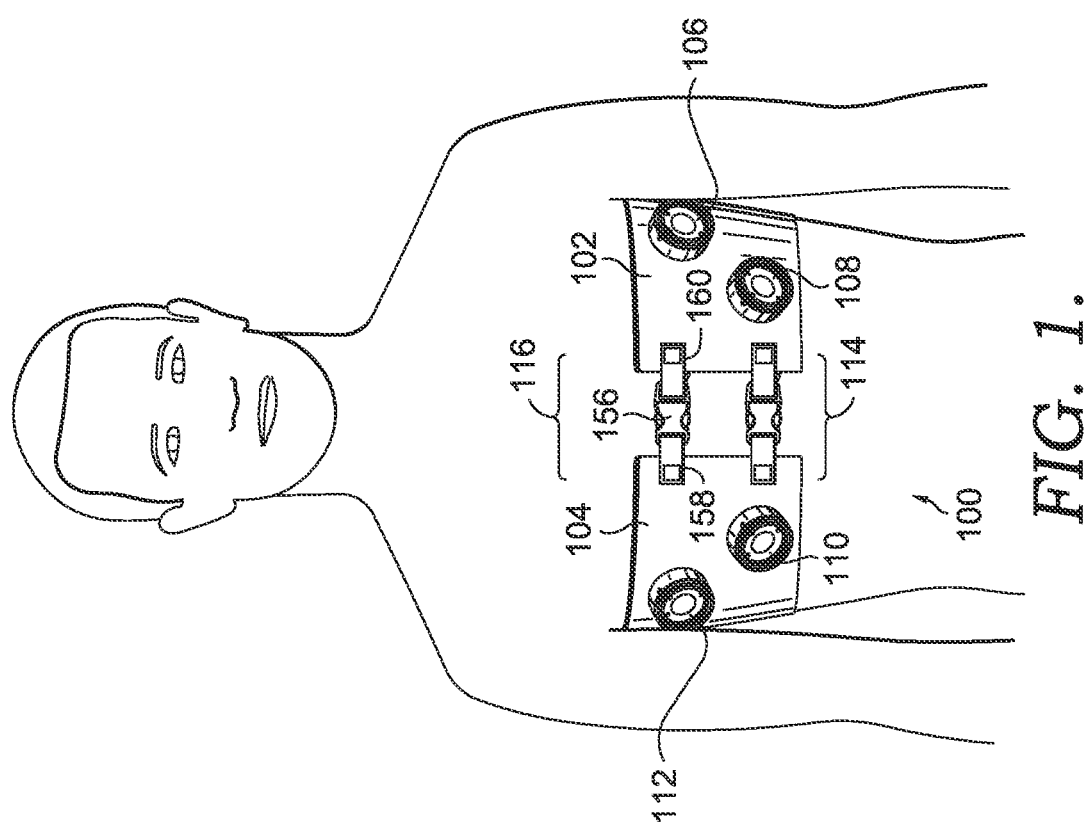
FIG. 2 is a rear, perspective view of an exemplary chest band including vibrating elements, where the exemplary chest band is being worn by a user, in accordance with an exemplary embodiment hereof.

Referring initially to FIG. 1, a front, perspective view of an exemplary chest band 100, where the exemplary chest band is being worn by a user, is provided. FIG. 2 provides a rear, perspective view of the exemplary chest band 100 being worn by the user. The chest band 100 may include one or more chest band segments, such as the chest band segments 102 and 104. Each chest band segment may include one or more vibrating elements. For example, the chest band segment 102 includes vibrating elements 106, 108, 122, and 124, and the chest band segment 104 includes vibrating elements 110, 112, 118, and 120. The vibrating elements may be uniform in size and/or shape. Additionally or alternatively, the vibrating elements may vary in size and/or shape. At the front of the user's body, the chest band segments 102 and 104 are coupled to one another by connection components 114 and 116. At the back of the user's body, the chest band segments 102 and 104 are coupled to one another by connection components 126 and 128.

As shown in FIGS. 1-2, one or more chest band segments may be coupled to one another to form a circumferential chest band. While the exemplary chest band 100 includes two chest band segments (chest band segments 102 and 104), any number of chest band segments is contemplated as being within the scope hereof. For example, a single chest band segment might wrap around the body of the user. In this case, one or more connection components may be needed in only one location in order to couple one end of the single chest band segment to the opposing end of the single chest band segment. In other examples, more than two chest band segments may be coupled to one another in order to form a chest band. In this instance, connection components may be used to couple one chest band segment to the next in order to form a continuous circumferential chest band. A chest band comprising multiple chest band segments may provide several advantages. For example, chest band segments having various uniform configurations may be manufactured, and each individual user may select a number of chest band segments having a desired configuration to serve the particular user's needs. For example, if a user has a relatively large chest circumference, the user might require several chest band segments, while a young child having a relatively small chest circumference might require fewer chest band segments. Additionally or alternatively, multiple sizes of chest band segments and/or chest bands might be provided. A further advantage of chest bands comprising multiple chest band segments is that a user may easily replace a single chest band segment that is malfunctioning. In other words, if one vibrating element on one chest band segment is not working, the user may simply replace that singular chest band segment with a new one, rather than incurring the expense of replacing the entire chest band.

The chest band segments 102 and 104 may be comprised of any type and/or number of materials. For example, a rigid and/or semi-rigid material, such as a plastic, may be used. Additionally or alternatively, a flexible material, such as a foam and/or elastic material, may be used. In some instances, any combination of rigid, semi-rigid, and flexible materials may be used to form a chest band segment.

The illustrative connection components 114, 116, 126, and 128 shown in the figures include a snap-fit buckle that joins two straps, each of which is coupled to a chest band segment. For example, connection component 116 includes a snap-fit buckle 156 that joins strap 158, which is coupled to the chest band segment 104, with strap 160, which is coupled to the chest band segment 102. The snap-fit buckle 156 may allow the length of strap 158 and/or strap 160 to be adjusted. The remaining connection components may provide similar features. In this way, the circumference of the chest band 100 may be easily adjusted and tailored to the size of a particular user. Additionally, the material comprising straps 158 and 160 may be elastic, such that the connection components may stretch in length. Advantageously, this allows the chest band 100 to fit snugly around the chest of the user, while also allowing the user to take deep breaths and cough. Thus, the user need not pause or discontinue treatment in order to breathe deeply or cough to expel mucus from the lungs. Accordingly, the user may engage in any number of activities while wearing the chest band and engaging in chest therapy.

Figure 18:
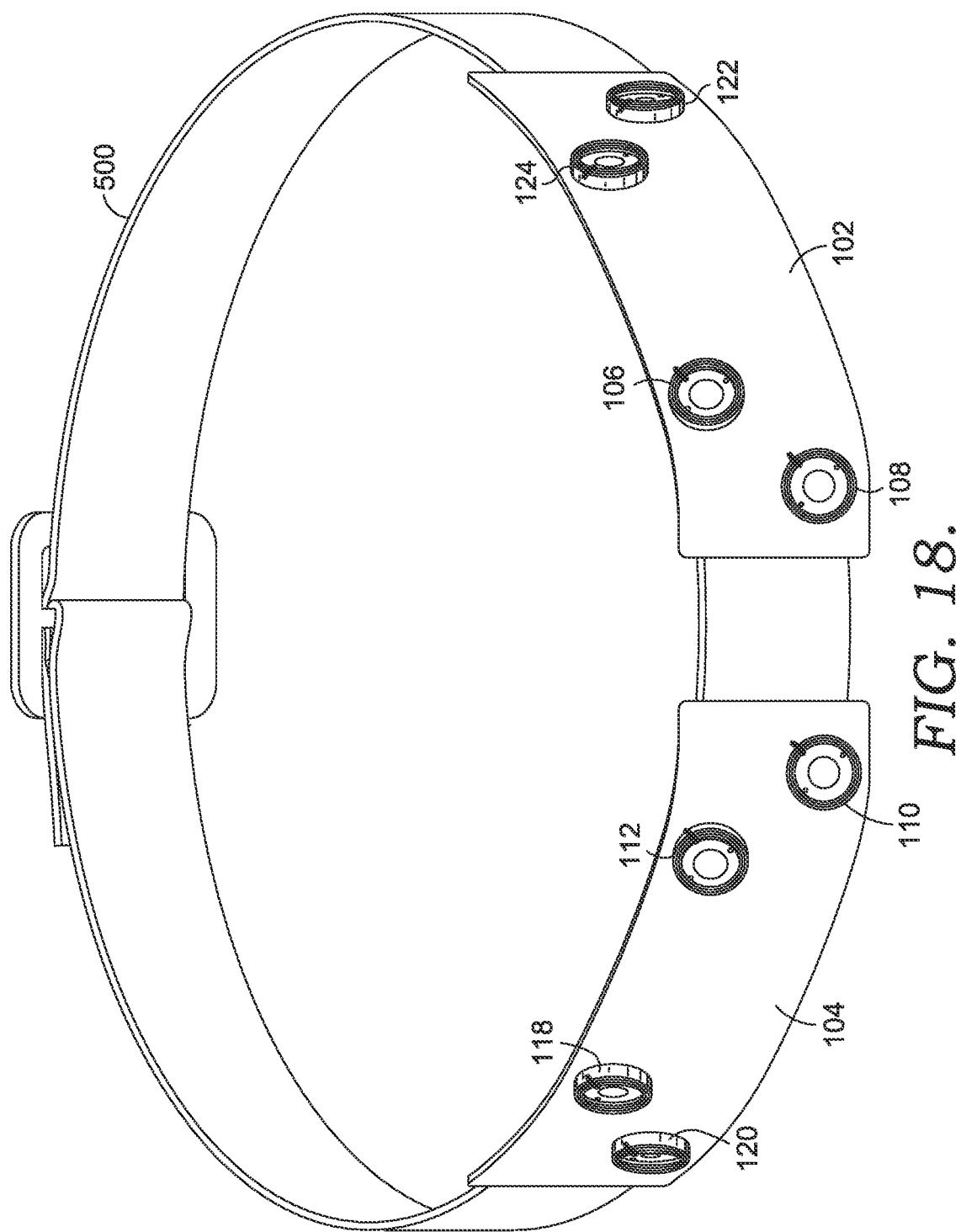
FIG. 18 is a front, perspective view of an exemplary belt on which chest band segments are mounted, in accordance with an exemplary embodiment hereof.

It will be understood that the connection components 114, 116, 126, and 128 are exemplary only, and that any number of other connection component configurations are included within the scope hereof. For example, the connection components may comprise clasps, belts, hook-and-loop fasteners, ties, laces, zippers, or any other means for connecting one chest band segment to another. Any combination of these components is included within the scope hereof. It will further be understood that the number of connection components illustrated in FIGS. 1-2 is exemplary only, and that any number of connection components may be used to connect one chest band segment to another. In some instances, the chest band segments may be mounted on a belt, such as an elastic belt, where the belt wraps around the chest of the user. Thus, in some instances, the chest band segments might not include connection components, but might instead be mounted on a belt or other item that may be secured around the user's chest. For example, FIG. 18 shows an exemplary belt 500 on which chest band segments 102 and 104 are mounted.

As shown in FIGS. 1-2, the vibrating elements 106, 108, 110, 112, 118, 120, 122, and 124 may be coupled to the chest band segments 102 and 104. When the user wears the chest band, the vibrating elements are positioned at various portions of the user's body, and when the vibrating elements are in operation, they provide a vibrational force to the user's body. The operation of the vibrating elements and the vibrational force provided to the user's body are discussed in more detail with respect to FIGS. 6-10 below, while exemplary configurations of the vibrating elements are discussed here with respect to FIGS. 1-2.

The vibrating elements may be positioned at particular locations on the chest band segments, such that when the chest band is worn by a user and the chest band segments are positioned adjacent to the user's body, the vibrating elements are located at a desired portion of the user's lung. For example, the vibrating elements may be placed according to particular lung lobe regions in order to provide a vibrational force to areas of the lung where mucus accumulates. The configuration of vibrating elements illustrated in FIGS. 1-2 is exemplary only. In other instances, the vibrating elements may be positioned at any location on the chest band segments 102 and 104.

The exemplary configuration shown in FIGS. 1-2 does, however, provide certain advantages, including enhanced mobility of the user while he is wearing the chest band. This enhanced mobility is at least partially attributable to the positioning of the upper vibrating elements, including vibrating elements 106, 112, 118, and 124, at a lateral area of the user's body, and the positioning of the lower vibrating elements, including vibrating elements 108, 110, 120 and 122, at a medial area of the user's body. As a user moves and swings his arm, the upper portion of his arm, near his armpit, has a more limited range of motion than a lower portion of his arm, near his elbow. Thus, as the user walks, runs, or engages in any number of activities, the lower portion of the user's arm may swing across the user's body or rub against the user's torso. The motion of the upper portion of the user's arm, by contrast, will be more limited. Accordingly, an upper vibrating element, such as the vibrating element 106, may be located at a lateral portion of the user's body and may have limited impact on the user's arm motions. Because the lower portion of the user's arm has a greater range of motion, a lower vibrating element, such as vibrating element 108, may be located at a medial portion of the user's body. Thus, as the user's arm moves next to the user's side, the user's arm is less likely to catch on and/or rub against the vibrating element 108, because it is located at a medial portion of the user's chest. Accordingly, the exemplary configuration depicted in FIGS. 1-2 allows the vibrating elements to be positioned at various portions of the user's lungs, while also maximizing the mobility of the user and allowing the user to swing his arms freely when the user is wearing the chest band.

Figure 3:
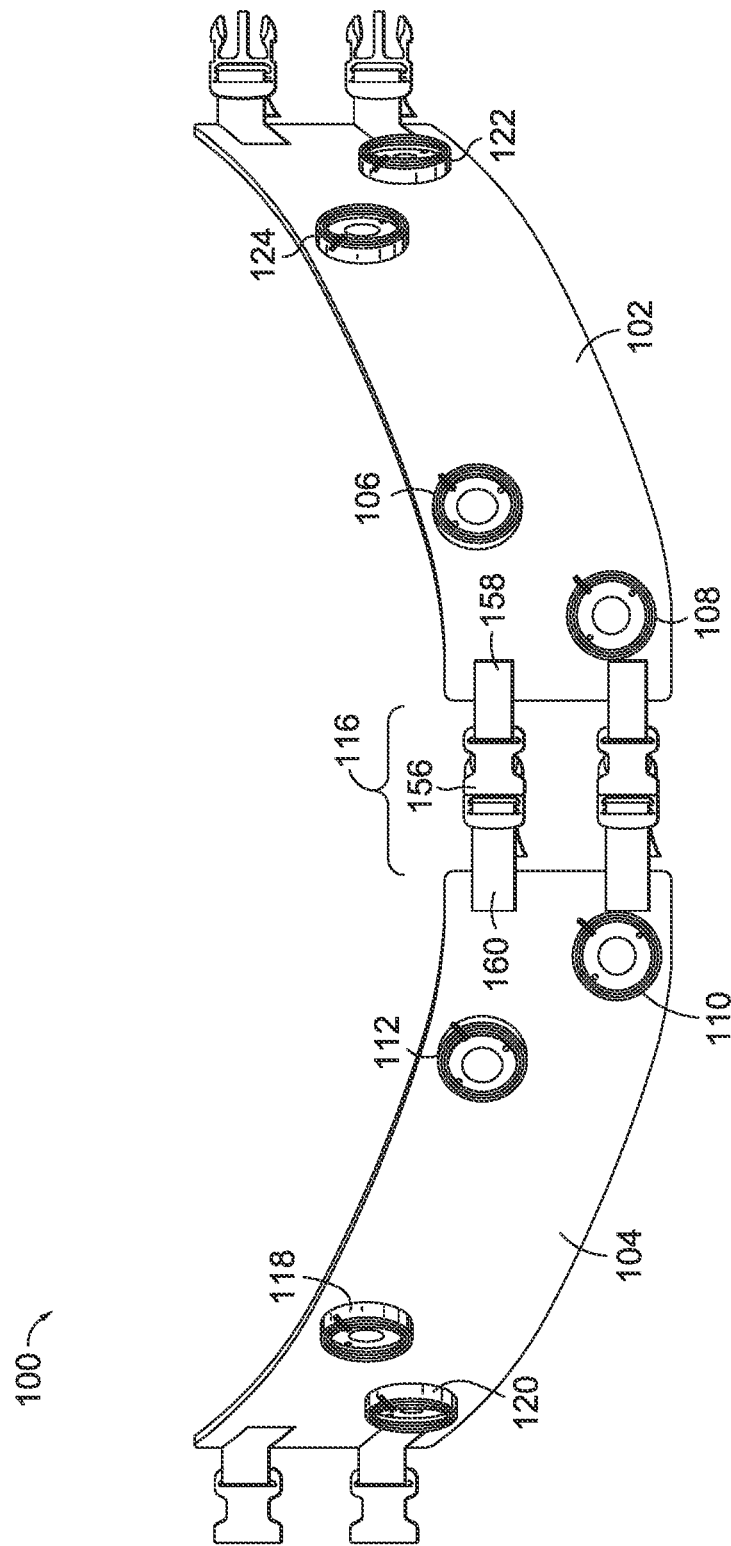
FIG. 3 is a front, perspective view of an exemplary chest band including vibrating elements, in accordance with an exemplary embodiment hereof.
Figure 4:
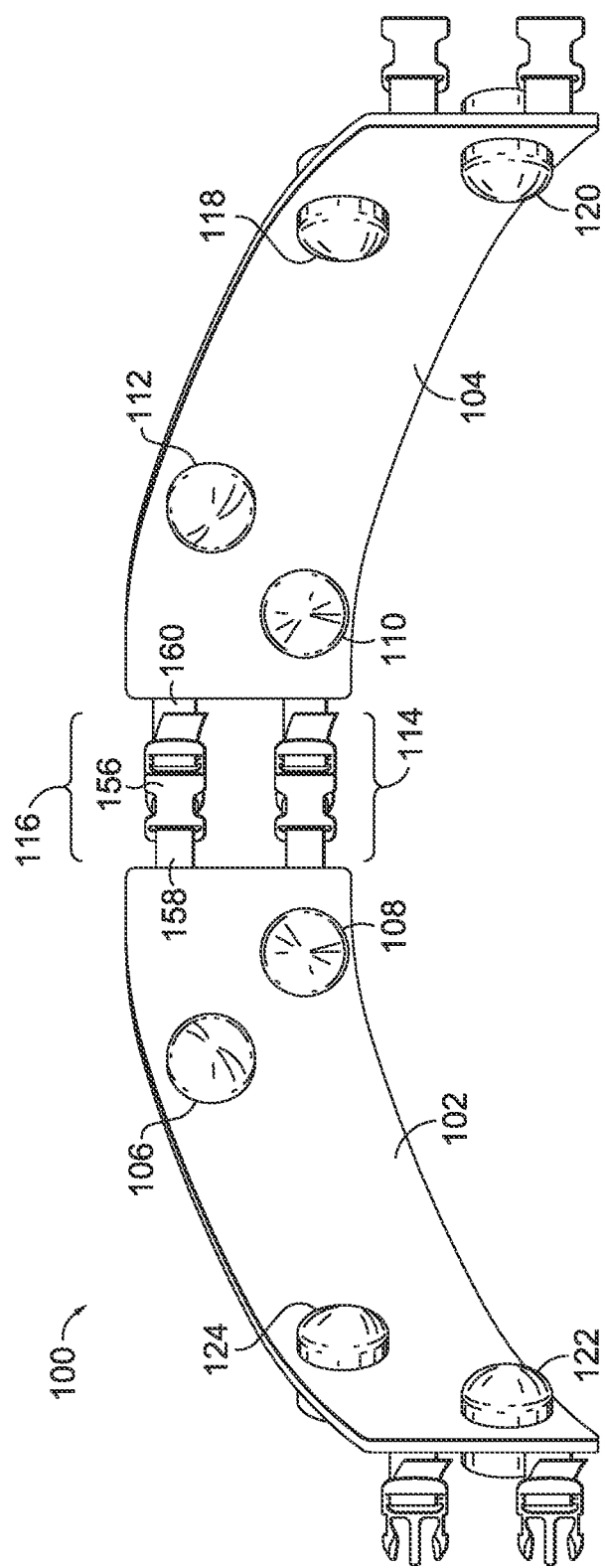
FIG. 4 is a rear, perspective view of an exemplary chest band including vibrating elements, in accordance with an exemplary embodiment hereof.

Turning now to FIGS. 3-4, a front, perspective view of the exemplary chest band 100 is provided in FIG. 3. The portion of the chest band 100 that is visible in FIG. 3 is the portion that may face away from the user when the user wears the chest band. In other words, it is the same portion that is visible in FIGS. 1-2. A rear, perspective view of the exemplary chest band 100 is provided in FIG. 4. The portion of the chest band 100 that is visible in FIG. 4 is the portion that may be adjacent to the user's body when the user wears the chest band 100. In other words, this portion of the chest band 100 is not visible when the user wears the chest band, because this is the portion that presses against the user's body.

FIG. 5 shows a plan view of a top surface of the exemplary chest band segment 102. FIG. 6 provides a cross-section view of the exemplary chest band segment 102 of FIG. 5. As shown in FIG. 6, the chest band segment may resemble a flat panel. In particular, the chest band segment 102 may include a top surface 130 that is parallel to an opposite bottom surface 132, such that the chest band segment forms a plane. The chest band segment 102 may be configured such that the bottom surface 132 is positioned adjacent to the user's body when the chest band segment 102 is in use. The vibrating elements 108 and 122 extend through the bottom surface 132 and the top surface 130 of the chest band segment 102. As can be seen in this cross-section view of FIG. 6, the vibrating elements 108 and 122 are maintained in a vertical position with respect to the planar surface provided by the chest band segment 102. This vertical positioning of vibrating elements will be discussed in greater detail below with respect to FIGS. 6-7, after the exemplary components that may be included in the vibrating elements are described with respect to the vibrating element 108 in FIGS. 8-10.

Figure 8:
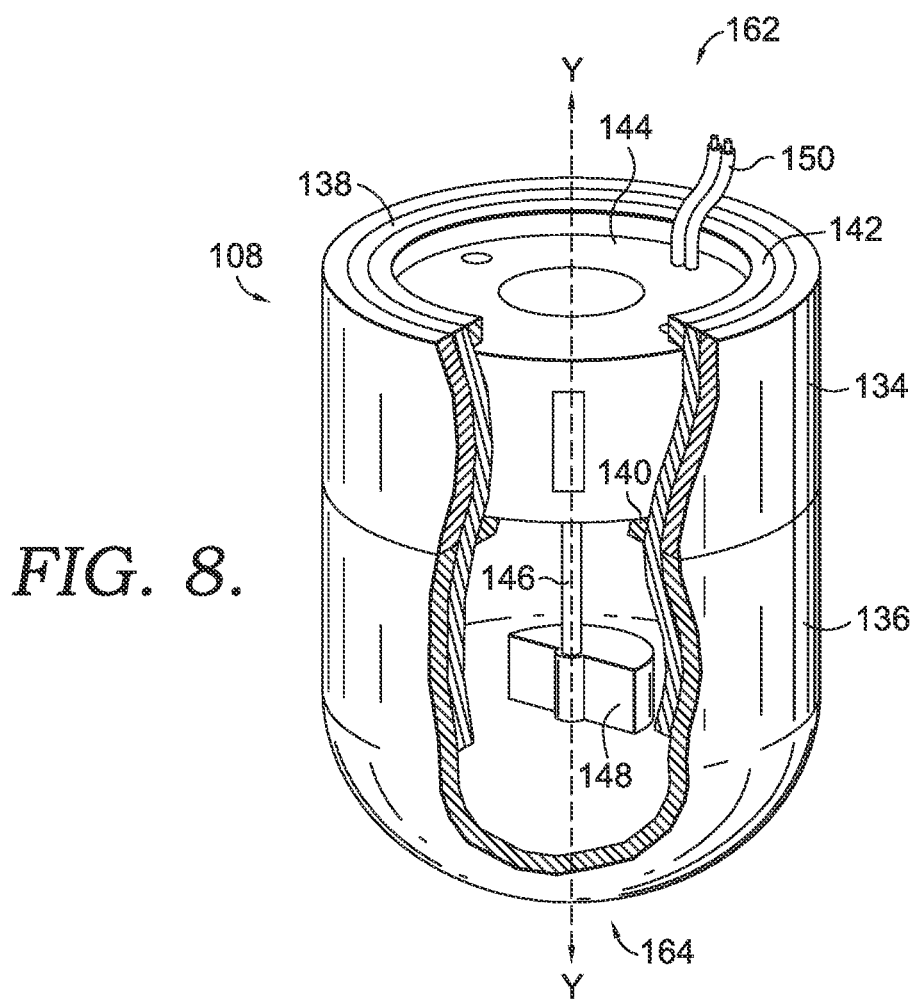
FIG. 8 is a cutaway view of an exemplary vibrating element, in accordance with an exemplary embodiment hereof.

A cutaway view of the exemplary vibrating element 108 is provided in FIG. 8. The vibrating element 108 may have a top end 162 and an opposite bottom end 164. In embodiments, the top end 162 and the bottom end 164 are axially opposed along a central vertical axis Y. The vibrating element may include a motor having various components, such as a motor body 144, a shaft 146, and a mass 148. A power connection 150 may provide power to the motor. The vibrating element 108 may further include a housing for the motor components. In particular, an inner housing 138 and an outer housing having an upper portion 134 and a lower portion 136 may be provided. The position of the motor body 144 may be maintained within the inner housing 138 by one or more positioning rings. For example, an upper positioning ring 142 may be positioned adjacent to the top of the motor body 144 at the top end 162 of the vibrating element 108. A lower positioning ring 140 may be positioned adjacent to the bottom of the motor body 144. In this way, the upper positioning ring 142 and the lower positioning ring 140 may maintain the motor body 144 at a desired position within the inner housing 138. The exemplary embodiment depicted in the figures includes an asymmetric outer housing. For example, the lower portion 136 of the outer housing, which is adjacent to the user's chest during use, may include a rounded surface that serves as a percussion cap. The percussion cap may enhance the user's comfort during chest physical therapy. For example, even if an intense vibrational force is provided to the user's body by the vibrating elements, the percussion cap may allow such force to be provided with minimal discomfort to the user. Other configurations of an outer housing are included within the scope hereof. In some instances, a symmetric outer housing may be used.

Figure 10:
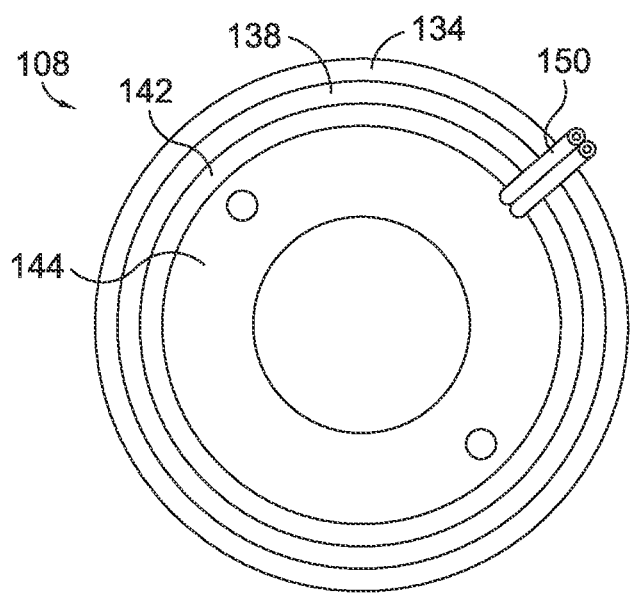
FIG. 10 is a top-down plan view of an exemplary vibrating element, in accordance with an exemplary embodiment hereof.
Figure 9:
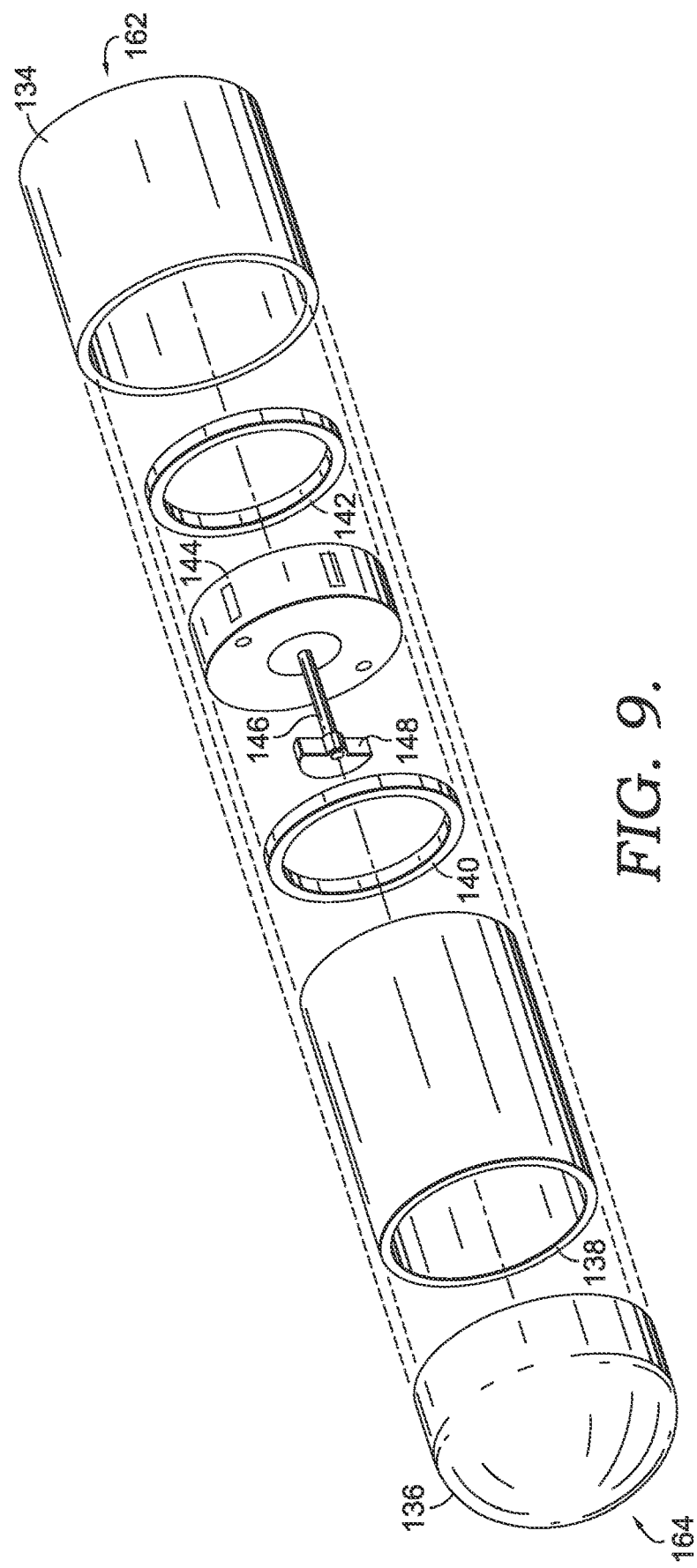
FIG. 9 is an exploded view of an exemplary vibrating element, in accordance with an exemplary embodiment hereof.

Each of the vibrating element components described with respect to FIG. 8 is also depicted in the exploded view of the vibrating element 108 provided by FIG. 9. As shown in FIG. 9, the upper positioning ring 142 and the lower positioning ring 140 may be positioned adjacent to a top surface and a bottom surface, respectively, of the motor body 144. The two positioning rings and the motor may fit within the inner housing 138. The outer housing upper portion 134 and the outer housing lower portion 136 may fit over the inner housing 138. FIG. 10 provides a top-down plan view of the exemplary vibrating element 108.

As mentioned, when the vibrating element 108 is in operation, it may provide a vibrational force. In particular, when power is supplied to the motor via the power connection 150, the mass 148 may be caused to rotate about the vertical axis Y. Due to the asymmetric configuration of the mass 148, as the mass 148 rotates, it causes displacement of the vibrating element 108. This displacement creates a vibrational force. The shaft 146 and the mass 148 may be allowed to rotate freely in order to maximize the vibrational force provided. As used herein, the term "asymmetric mass" includes a mass that is asymmetric in shape, such as the exemplary mass 148, as well as a mass that is symmetric in shape but that is coupled asymmetrically to the shaft 146. For example, a cylindrical weight is symmetric in shape, but when the shaft 146 is coupled to the cylindrical weight at a point near the perimeter of the cylinder face, as opposed to the center of the cylinder face, the cylindrical weight lacks rotational symmetry about the axis Y corresponding to the shaft 146. A mass that is symmetric in shape but that is off-center with respect to the shaft 146 will cause displacement of the vibrating element 108 as the mass rotates and is therefore included in the term "asymmetric mass."

The frequency at which the vibrating element 108 vibrates may be controlled by controlling the speed of the rotation of the mass 148. In one example, the vibrating element 108 may vibrate at a frequency between approximately 5 cycles per second and approximately 65 cycles per second (or between 5 hertz and 65 hertz). In another example, the vibrating element may vibrate at a frequency within a range of approximately 20 cycles per second to approximately 50 cycles per second (or 20 hertz to 50 hertz). In some embodiments, an "unbalanced motor," such as a low profile unbalanced motor, or a "vibration motor" may be included in the vibrating element. For example, the "Uni Vibe™ 24 mm Vibration Motor—13 mm Type," having a rated operating voltage of 12V and offered for sale by Precision Microdrives™, may be included in the vibrating element 108.

Returning now to FIG. 6, the vertical positioning of the vibrating elements 108 and 122 with respect to the planar surface provided by the chest band segment 102 will be discussed. As illustrated in FIG. 6, the vibrating element 108 may extend through the bottom surface 132 and the top surface 130 of the chest band segment 102. In particular, the vibrating element may extend vertically through these surfaces, such that the vibrating element 108 is maintained in a vertical position with respect to the planar surface provided by the chest band segment 102. In one instance, a vertical position may be characterized by the central vertical axis Y being approximately perpendicular to the planar surface provided by the chest band segment. As used herein, the terms "approximately" or "substantially," when used to describe a quantity and/or value, include a range of 85% to 115% of the specified quantity and/or value. For example, according to the statement above, if an angle between the vertical axis Y of the vibrating element 108 and the planar surface provided by the chest band segment 102 ranges between 76.5° and 103.5° (i.e. 85% and 115% of 90°, respectively), the central vertical axis Y of the vibrating element 108 may be described as "approximately" or "substantially" perpendicular to the planar surface provided by the chest band segment 102.

This vertical positioning may provide numerous advantages. One such advantage is that when the bottom end 164 of the vibrating element is positioned adjacent to the user's body, the vibrating element provides a vibrational force to the user's body. In particular, as the mass 148 rotates, the vibrating element 108 shakes and creates a percussive and/or tapping force on the user's body. This vibrational force may aid in loosening mucus in the user's lungs and clearing the user's airways. If the vibrating element was positioned horizontally, such that the vertical axis Y of the vibrating element 108 was parallel to the planar surface provided by the chest band segment 102, the vibrating element 108 might provide a "stroking" force, but it would not provide the vibrational force that is provided by the vertical orientation shown in FIG. 6. Nonetheless, in some instances, one or more vibrating elements may be positioned approximately parallel to the planar surface provided by the chest band segment 102.

In an exemplary embodiment, the vibrating element 108 is maintained in a vertical position with respect to the chest band segment 102 by, at least in part, a coupling between the housing for the vibrating element 108 and the chest band segment 102. As shown, the upper portion 134 of the outer housing is positioned adjacent to the top surface 130 of the chest band segment 102 and the lower portion 136 of the outer housing is positioned adjacent to the bottom surface 132 of the chest band segment 102.

FIG. 7 provides an enlarged, cross-section view of the vibrating element 108 of FIG. 6. This view more clearly illustrates an exemplary coupling between the housing for the vibrating element 108 and the chest band segment 102. As shown, the inner housing 138 may fit through an opening in the chest band segment 102, such that a first portion of the inner housing 138 is above the top surface 130 of the chest band segment 102 and a second portion of the inner housing 138 is below the bottom surface 132 of the chest band segment 102. The upper portion 134 of the outer housing may be secured to the first portion of the inner housing 138 that is above the top surface 130 of the chest band segment 102. Similarly, the lower portion 136 of the outer housing may be secured to the second portion of the inner housing 138 that is below the bottom surface 132 of the chest band segment 102. The outer housing portions may be secured to the inner housing 138 in any number of ways, such as gluing, snapping, clamping, threading, or any other means of securing the outer housing portions to the inner housing portions. As shown in FIG. 7, the upper portion 134 and the lower portion 136 of the outer housing may be positioned directly adjacent to the top surface 130 and the bottom surface 132, respectively, of the chest band segment 102. For example, the outer housing portions may pinch the chest band segment 102 such that the vibrating element does not slide up and down with respect to the chest band segment 102 during use. In other words, the vibrating element 108 may remain coupled to the chest band segment 102 in a fixed position during operation. This configuration may advantageously maintain the vibrating element in a vertical position, even as the mass 148 rotates and causes the vibrating element to vibrate. For example, as the vibrating element vibrates, it does not tip over; instead, it may remain substantially upright, such that the bottom end 164 of the vibrating element may remain adjacent to the user's body and may continue to provide a vibrational force to the user's body.

According to this exemplary configuration, if the position of the motor body 144 corresponds to the upper portion 134 of the outer housing, as maintained by the positioning rings 140 and 142 within the inner housing 138, the motor body 144 is positioned above the top surface 130 of the chest band segment 102. This is illustrated in FIG. 7. Additionally, if the motor body 144 is positioned in this way, the position of the mass 148 corresponds to the lower portion 136 of the outer housing. Thus, the mass 148 is positioned below the bottom surface 132 of the chest band segment. This is also illustrated in FIG. 7. In this example, when the vibrating element is secured to the chest band segment 102 at a point that falls between the motor body 144 and the mass 148, a pivot point may be created, where the vibrating element may rock and/or shake based on that pivot point. In the exemplary embodiment depicted in the figures, the entirety of the motor body 144 is disposed above the top surface 130 of the chest band segment 102, and the entirety of the mass 148 is disposed below the bottom surface 132 of the chest band segment. However, a pivot point may be created where only a portion of the motor body 144 is disposed above the top surface 130 and/or only a portion of the mass 148 is disposed below the bottom surface. The exact positioning of the vibrating element may be adjusted to optimize this pivot point location, thereby optimizing the vibrational force that may be provided to the user's body, as well.

It will be understood that while an exemplary embodiment of a vibrating element coupled to a chest band segment is described with respect to various separate components, in other embodiments, certain parts may be machined particularly for use with the apparatus described herein. For example, a vibrating element may be machined such that it comprises components different in number and/or nature from those described above, but nonetheless provides the desired vibrating effect. All such variations are included within the scope hereof.

As mentioned, the chest band segment 102 may be comprised of any number of materials. A material selection may take into account a preference to maintain the vibrating elements in a vertical position.

Figure 11:
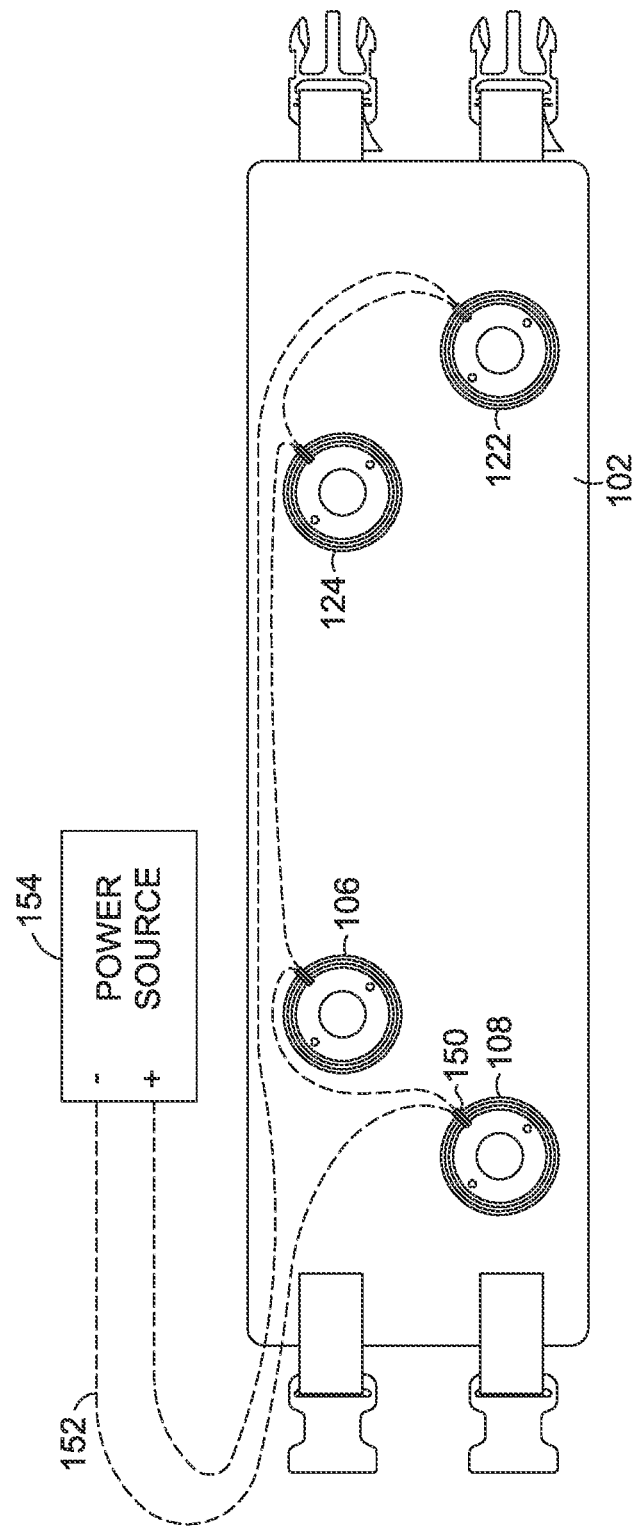
FIG. 11 is a plan view of a top surface of an exemplary chest band segment including vibrating elements, where each of the vibrating elements is electrically coupled to a power source, in accordance with an exemplary embodiment hereof.
Figure 12:
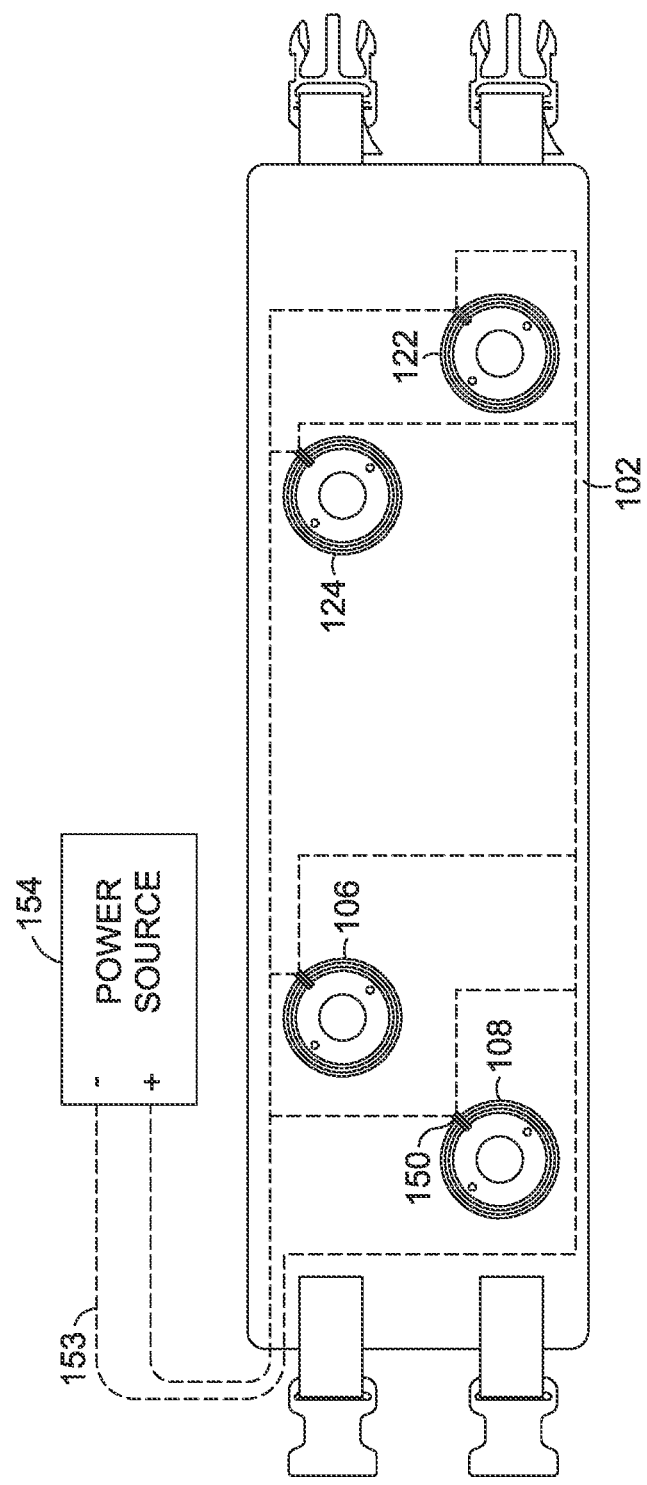
FIG. 12 is a plan view of a top surface of an exemplary chest band segment including vibrating elements, where each of the vibrating elements is electrically coupled to a power source, in accordance with an exemplary embodiment hereof.

Turning now to FIG. 11, a top-down plan view of the exemplary chest band segment 102 is provided. In particular, FIG. 11 illustrates the way in which multiple different vibrating elements may be electrically coupled to a single power source 154 by way of a series circuit 152. FIG. 12 illustrates the way in which multiple different vibrating elements may be electrically coupled to a single power source 154 by way of a parallel circuit 153. In either scenario, one or more wires may connect a power connection, such as the power connection 150 discussed with respect to FIGS. 6-10, to the power source 154. A selection of a series circuit 152 or a parallel circuit 153 may be based on considerations of battery life and motor effectiveness, among other things. A series circuit 152, for example, may provide for increased battery life (such as increased life of the power source 154) but decreased effectiveness of the vibrating element (such as a decreased effectiveness of a motor component included in a vibrating element). By contrast, a parallel circuit 153 may utilize the full potential of a vibrating element (such as the full potential of a motor component included in a vibrating element), but may cause the power source 154 to be drained more quickly. Additionally, in a parallel circuit 153, if one vibrating element fails, the remaining vibrating elements may continue to function properly. In a series circuit 152, if one vibrating element fails, then the remaining vibrating elements included in the circuit will not function properly, either. Accordingly, each circuit configuration is associated with various advantages and disadvantages.

The power source 154 of FIGS. 11-12 may include a rechargeable battery, such as a lithium-ion battery. As shown, the power source 154 may be external to the chest band segment 102. In some instances, the power source 154 may be integrated into the chest band segment 102. In additional instances, the vibrating elements may be coupled to multiple power sources. Any combination of the above is included within the scope hereof.

Figure 13:
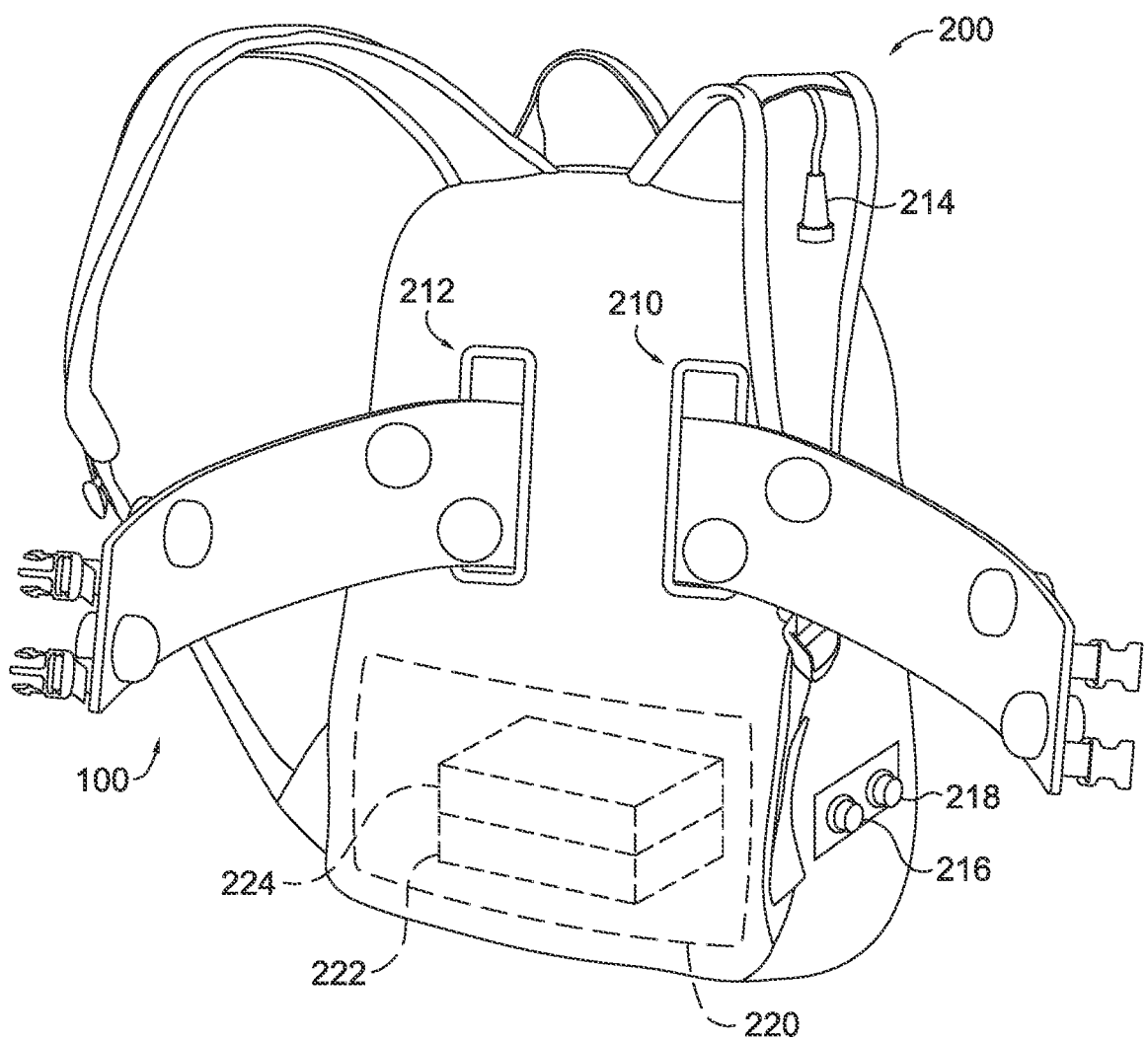
FIG. 13 is a rear, perspective view of an exemplary chest band coupled to an exemplary wearable pack, in accordance with an exemplary embodiment hereof.
Figure 14:
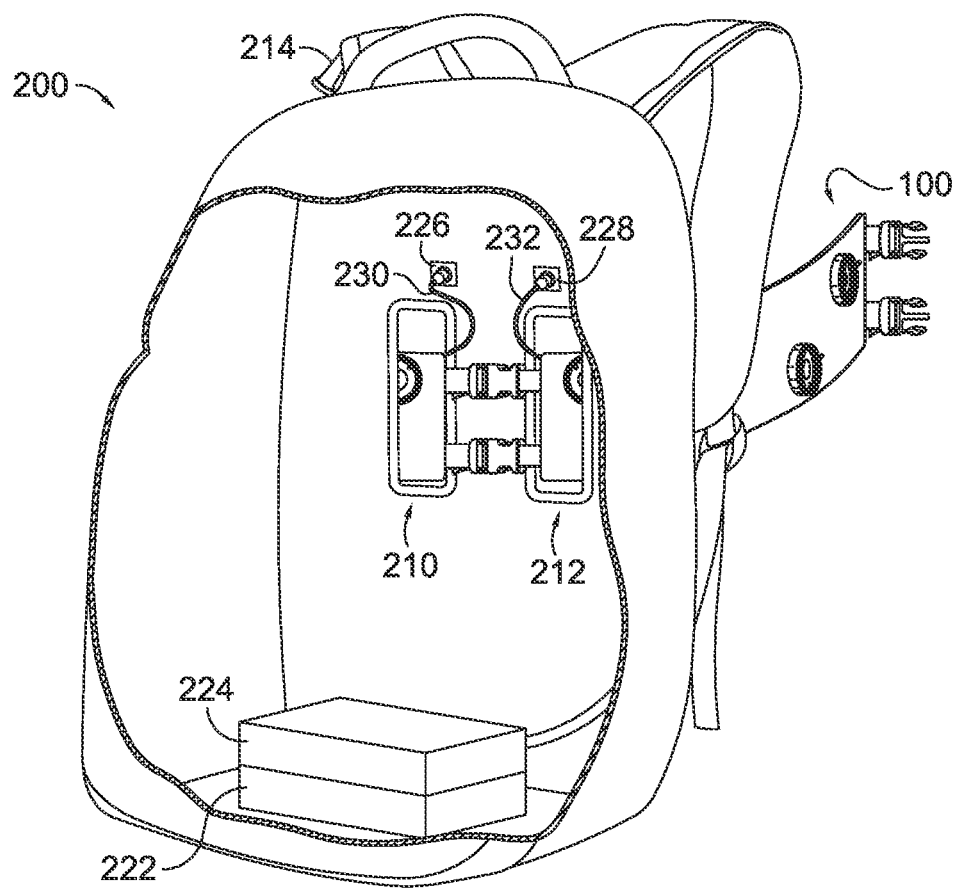
FIG. 14 is a cutaway view of an exemplary wearable pack coupled to an exemplary chest band, in accordance with an exemplary embodiment hereof.

As previously mentioned, a significant advantage of the apparatus described herein is that it is portable. In one example, this portability is enhanced by providing the components of the apparatus in conjunction with a wearable pack. A rear, perspective view of an exemplary wearable pack 200 is illustrated in FIG. 13 and a cutaway view showing an exemplary interior of the wearable pack 200 is illustrated in FIG. 14. The wearable pack 200 may be, for example, a backpack. Numerous other wearable packs are included within the scope hereof, including fanny packs, sling bags, shoulder bags, purses, and any other pack that may be worn and/or carried by a user. Additionally or alternatively, the apparatus may be integrated into a garment, such as a jacket, sweatshirt, vest, or other garment.

Figure 15:
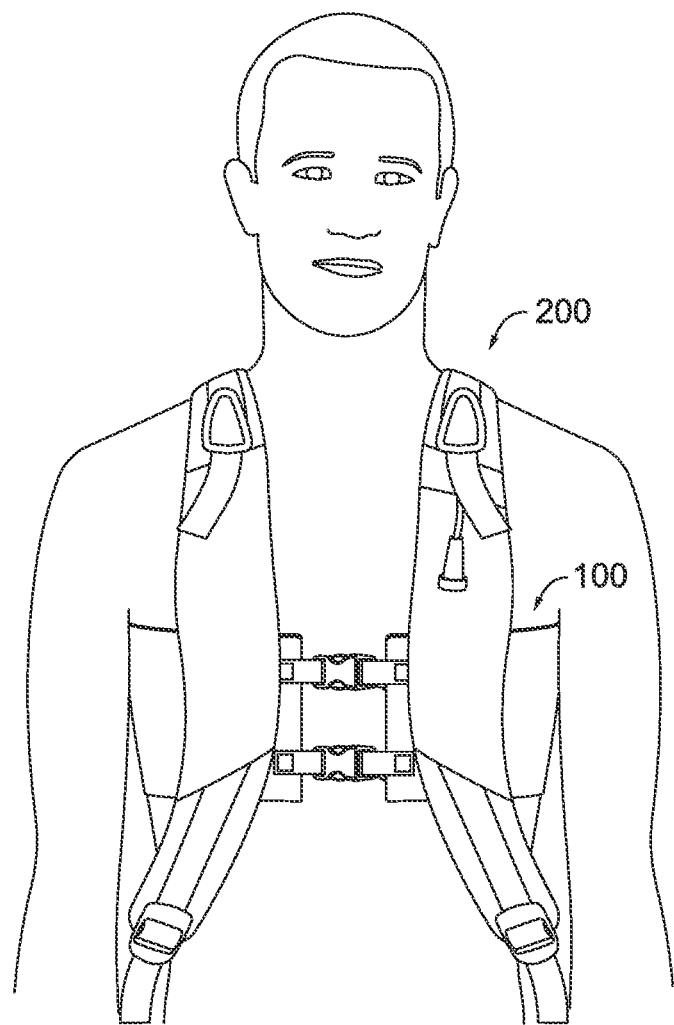
FIG. 15 is a front, perspective view of an exemplary chest band coupled to an exemplary wearable pack, where the combination of the chest band and the wearable pack is being worn by a user, in accordance with an exemplary embodiment hereof.

FIGS. 13-14 illustrate one exemplary way in which the chest band 100 may be coupled to the wearable pack 200. In this example, the chest band 100 slides through two chest band slots 210 and 212. The user may then fasten the chest band 100 around his chest and wear the wearable pack 200 on his back, as illustrated in FIG. 15.

As shown in FIG. 14, the chest band 100 may be electrically coupled to a power source 222. This exemplary electrical coupling may be achieved by plugging the power components 230 and 232 into the power ports 226 and 228, respectively. The power ports 226 and 228 may be electrically coupled to the power source 222. For example, one or more wires may run from the power ports 226 and 228 to the power source 222. These wires may be sewn into an interior wall of the wearable pack 200.

The chest band 100 and the power source 222 may further be electrically coupled and/or communicatively coupled to user input components 216 and 218. Thus, the operation of the vibrating elements included on the chest band 100 may be initiated and/or adjusted based on a user input received at user input component 216, for example. In one basic embodiment, the chest band 100, the user input component 216, and the power source 222 may operate to provide the chest therapy described herein. The user input component 216 may include a resistor, such as an analog resistor, a variable resistor, or a combination thereof, in order to provide a variety of operational settings (e.g., high, medium, or low vibrational intensity, as well as any number of intermediate settings; a pulse setting; a waterfall setting). These components may be electrically coupled via a printed circuit board, for example. Because all of these components are relatively small and lightweight, they may be easily stored and/or transported, thereby providing enhanced mobility for the user. As used herein, the term "electrically coupled" includes wireless electrical connections, such as a Bluetooth® connection. For example, chest band 100 may be controlled via a user input component at a mobile device application and/or a remote control.

In one example, the user input component 216 may enable a user to turn on the vibrating elements included in the chest band 100 and select a desired level of vibrational force. As mentioned, the user input component 216 may provide for any number of power settings. For example, six different settings associated with varying levels of vibrational intensity may be provided. As mentioned, the frequency of vibration provided by the vibrating elements may range from 5 hertz to 65 hertz, in some embodiments. In one example, a "low" setting may correspond to a frequency of 20 hertz and a "high" setting may correspond to a frequency of 50 hertz, where intermediate settings may correspond to frequencies between 20 hertz and 50 hertz. Thus, the same apparatus may provide a desired intensity of chest therapy to users of any number of ages and/or sizes. A small child, for example, might choose a low power setting, while a large adult might choose a high power setting. A user can thus choose a setting that is both effective and comfortable, according to his individual needs.

In addition to the chest band 100, the wearable pack 200 may include other therapy and/or treatment components. For example, a nebulizer treatment component 224 may be provided. The nebulizer treatment component 224 may include an air compressor connected to tubing that runs to a desired location on the wearable pack 200. An auxiliary attachment 214 may be connected to the end of the tubing. The auxiliary attachment 214 may be configured to attach to a nebulizer mouth piece. The wearable pack 200 may include an opening that allows the auxiliary attachment 214 to be accessed from the exterior of the wearable pack 200. For example, as shown in FIGS. 13-14, the auxiliary attachment 214 may be located at an exterior portion of a shoulder strap of the wearable pack 200, such that a user may easily attach a nebulizer mouth piece and conveniently engage in a nebulizer treatment. The nebulizer treatment component 224 may be electrically coupled to the power source 222, as well as the user input components 216 and 218. For example, the user input component 218 may allow a user to turn the nebulizer treatment component on and off.

Accordingly, the user input components 216 and 218 may allow a user to engage a desired operational setting of the chest band 100 and/or the nebulizer treatment component 224. Advantageously, the user may simultaneously engage in chest therapy using the chest band 100 and a nebulizer treatment using the nebulizer treatment component 224. And because the apparatus is designed to be portable, the user may engage in such therapy and treatment while performing any number of activities. For example, the apparatus may enable the user to engage in a chest therapy session and/or a nebulizer treatment while walking, running, biking, playing, or any other desired activity.

In additional embodiments, a programmable controller might also be electrically coupled to some or all of the components mentioned above. The controller may control the operation of the chest band 100, including the multiple vibrating elements, based on user input received at the user input component 216. The controller may be programmable to provide an expanded selection of operating settings. For example, the controller may provide any number of customized programs. One program might simultaneously engage all vibrating elements at the same power setting, thereby providing a similar vibrational force to the user's body from each vibrating element. Another program might selectively engage particular vibrating elements at customized power settings. For example, all vibrating elements might be simultaneously engaged, but the vibrational force provided by each vibrating element might vary. Additionally or alternatively, only a portion of the vibrating elements might be engaged at a particular point in time. The controller may further provide for timed programming, such that a particular program runs for a predetermined period of time. Any and all such combinations of the above are included within the scope hereof. The controller might also be electrically coupled to the nebulizer treatment component 224 and may provide customized operational settings for nebulizer treatments.

As shown in FIG. 13, the wearable pack 200 may include a compartment 220 for housing certain components, such as the power source 222 and the nebulizer treatment component 224. This compartment 220 may be a separate pocket included in the wearable pack 200, such that the components included therein are separated from other articles that may be stored in the wearable pack.

It will be understood that additional components might be included in an apparatus for providing chest therapy. For example, an alert component might remind a user that it is time to engage in a chest therapy and/or nebulizer treatment session. An alert provided by the alert component might include any combination of visual, audio, and/or tactile alerts. For example, a flashing light, a sounding alarm, and/or a vibration may remind a user that a predetermined period of time has elapsed since the last therapy and/or treatment session.

It should be noted that in the exemplary embodiment of FIGS. 13-14, the chest band 100 is both physically coupled and electrically coupled to the wearable pack 200 during use. However, the chest band 100 need not necessarily be physically attached to the wearable pack 200 in order for the chest band 100 to provide physical chest therapy. For example, if the wearable pack is a fanny pack, then the fanny pack may be worn around the user's waist, while the chest band 100 is worn separately around the user's chest. In this example, the chest band 100 may be electrically coupled to the fanny pack during operation, but need not be physically touching the fanny pack.

Furthermore, while exemplary embodiments above are discussed with respect to a wearable pack, in a further embodiment, the components required for operating the chest band 100 might be fully integrated into the chest band 100, itself. For example, a power source, a controller, and user input components might all be included in the chest band, such that a user can store and transport the chest band 100 in any way desired. Additionally, as mentioned, the components required for operating the chest band 100 and/or nebulizer treatment component 224 might be integrated into a garment, such as a jacket, sweatshirt, vest, or other article of clothing.

Turning now to FIG. 15, a front, perspective view is provided of the exemplary chest band 100 coupled to the exemplary wearable pack 200, where the combination of the chest band 100 and the wearable pack 200 is being worn by a user. In this exemplary embodiment, the chest band segments of the chest band 100 include covers that conceal the vibrating elements from view. Thus, the vibrating elements and any associated wiring may be hidden from view. In this instance, the connection components described above with respect to FIGS. 1-2 may be coupled to the cover material of the chest band segments. In addition to aesthetic considerations, chest band segments might include covers in order to enhance the comfort of the user while the chest band 100 is in use. For example, a cover comprising a particular material might make chest therapy sessions more comfortable for the user. The covers may be removable in some embodiments, such that a user may access the vibrating elements, wiring, and/or other components. This may facilitate maintenance and/or repairs, for example.

As mentioned, the configurations of the chest band and/or chest band segments discussed above are exemplary. Turning now to the remaining figures, additional configurations are discussed.

Figure 19A:
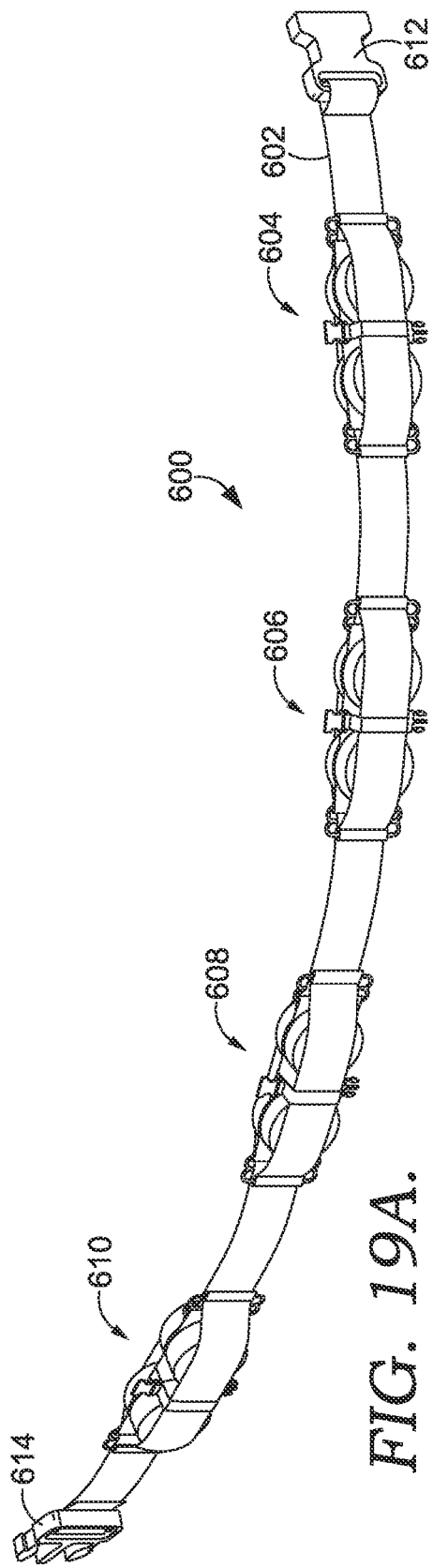
FIGS. 19A-B are front and rear, perspective views, respectively, of an exemplary chest band including a belt on which chest band segments are mounted, in accordance with an exemplary embodiment hereof.
Figure 19B:
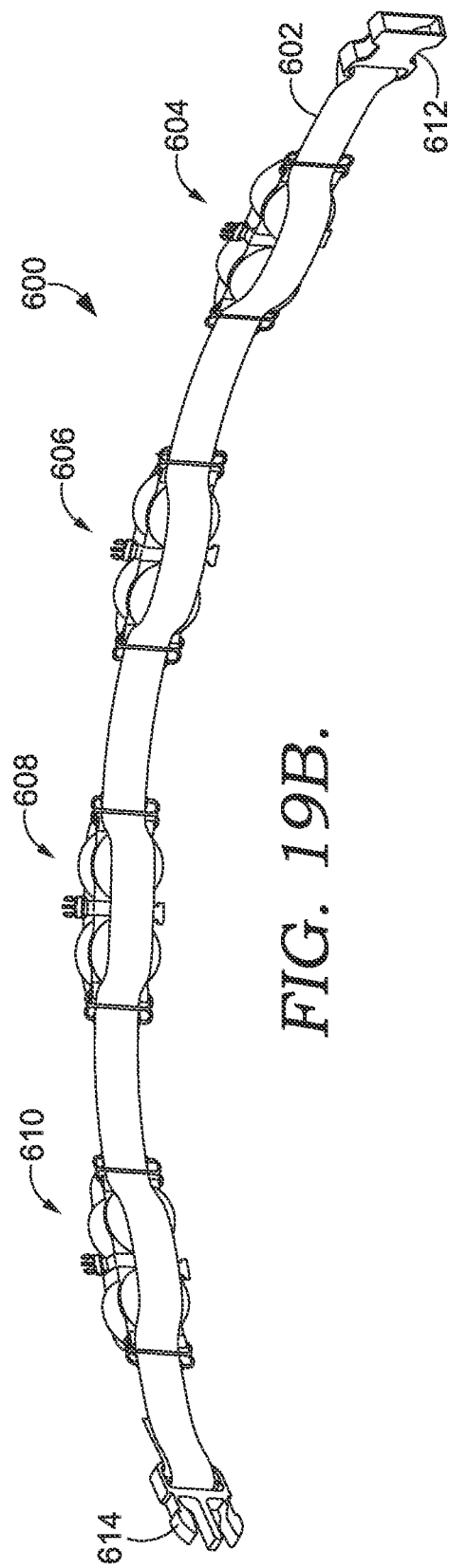
Figure 20A:
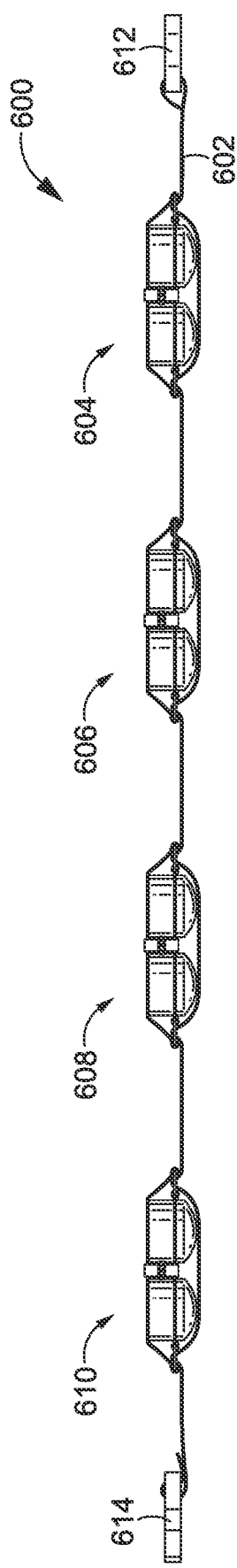
FIG. 20A is a side elevation view of the exemplary chest band of FIGS. 19A-B, in accordance with an exemplary embodiment hereof.
Figure 20B:
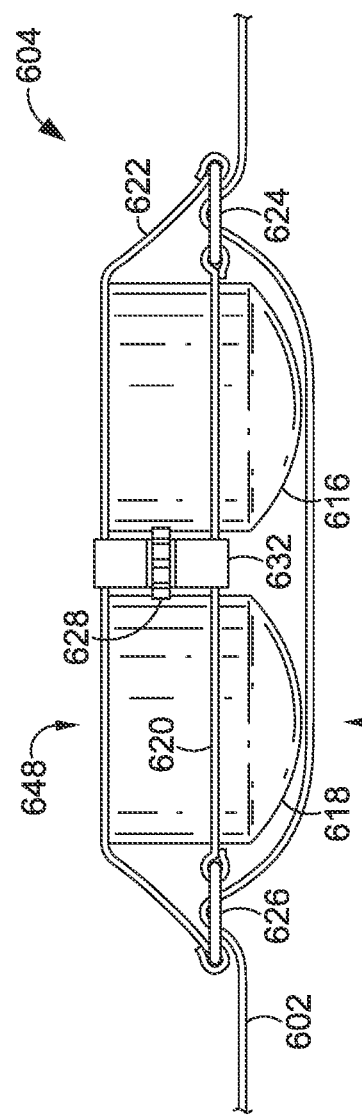
FIG. 20B is an enlarged side elevation view of a portion of the exemplary chest band of FIG. 20A, in accordance with an exemplary embodiment hereof.

FIG. 19A provides a front, perspective view of an exemplary chest band 600, and FIG. 19B provides a rear, perspective view of the exemplary chest band 600. The front, perspective view provided in FIG. 19A shows the side of the chest band 600 that faces away from a user's body when the user wears the chest band (i.e. the portion that is visible to an observer). The rear, perspective view provided in FIG. 19B shows the side of the chest band 600 that is adjacent to the user's body when the user wears the chest band 600 (i.e. the portion that is not visible to an observer). FIG. 20A provides a side elevation view of the chest band 600, and FIG. 20B provides an enlarged side elevation view of a portion of the chest band 600.

The chest band 600 includes a belt 602 onto which chest band segments 604, 606, 608, and 610 are mounted. Each of chest band segments 604, 606, 608, and 610 include vibrating elements for providing a vibrational force to a user's chest. The chest band segments may be permanently or adjustably mounted on the belt 602. For example, in the figures, chest band segments 604, 606, 608, and 610 are slidably mounted on the belt 602. Adjustable mounting allows a user to position each chest band segment at a precise desired location along the length of the belt 602. In the figures, the chest band segments 604, 606, 608, and 610 are evenly spaced along the length of the belt 602, but in use, they may be positioned at any location along the length of the belt 602 in order to provide a percussive force at a desired location on the user's body. While the exemplary chest band 600 includes four chest band segments, any number of chest band segments, each of which may include any number of vibrating elements, may be mounted on the belt 602. The modular design of the chest band 600 allows it to be customized based on the unique needs of a particular user.

Figure 21A:
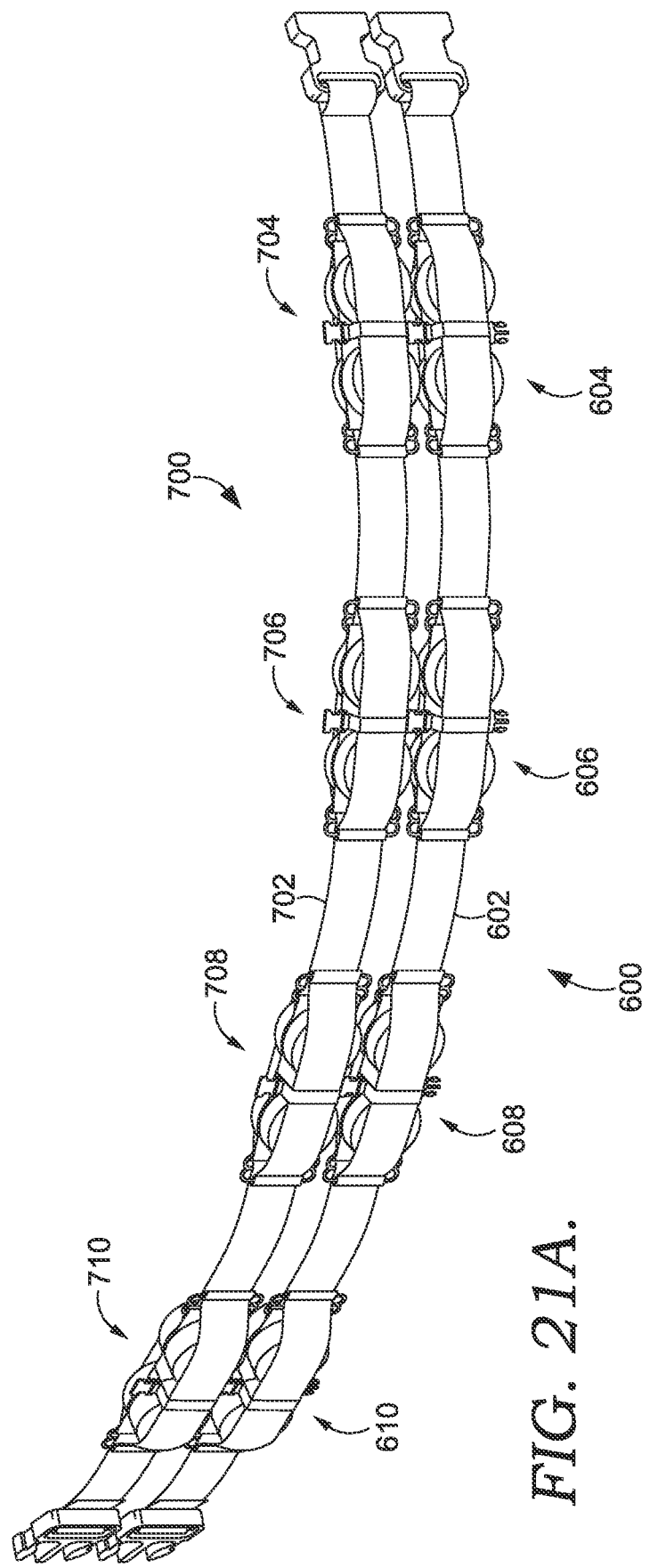
FIGS. 21A-B are front and rear, perspective views, respectively, of two exemplary chest bands that are coupled together in parallel, in accordance with an exemplary embodiment hereof.
Figure 21B:
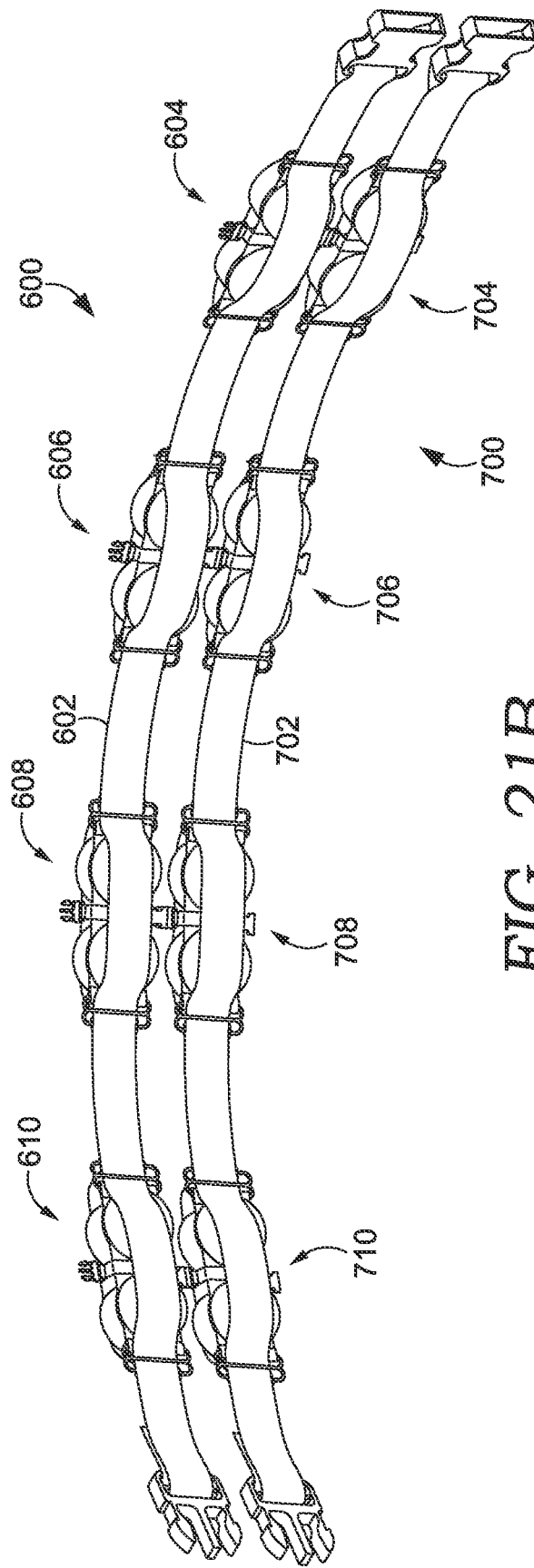

In order to provide further customization based on the unique needs of a particular user, the chest band 600 may be coupled to one or more other chest bands in parallel, as is depicted by the chest bands 600 and 700 in FIGS. 21A-B. This ladder configuration provides for the application of a percussive force across a larger area of the user's body. Accordingly, the apparatus can be customized based on user size and/or body shape (e.g., an adult may use two or more chest bands coupled together in parallel, while a child may use only one), severity of medical condition (e.g., a person having a very severe medical condition may use several chest bands coupled together in parallel, each of which includes multiple chest band segments, while a person having a less severe condition may use fewer chest bands and/or chest band segments), and other considerations. FIGS. 21A-B illustrate a one-to-one correspondence between the chest band segments on the belt 602 and the chest band segments on the belt 702, but based on the modular design of the chest bands 600 and 700, this need not necessarily be the case. For example, chest band segment 708 could be omitted from the multi-chest-band configuration. It may be desirable omit a particular chest band segment if percussive therapy is not desired at a particular location on a user's body and/or if a chest band segment at that particular location would impair the user's mobility. Similarly, it may be desirable to stagger chest band segments on multiple different bands. For example, chest band segment 708 might be mounted to the belt 702, but it may be staggered from chest band segment 608. The modular design of the chest bands 600 and 700 allow for such customization.

Exemplary features of various components of the chest band 600 will now be discussed, beginning with the belt 602. The belt 602 is characterized by a length that is greater than its width. For example, the ratio of the length to width of the belt 602 may be between approximately 5:1 and 30:1. The length of the belt 602 may be adjustable in order to provide a customized fit for a particular user. The belt 602 may be constructed of an elastic material. An elastic material advantageously permits a user to cough during a chest therapy session. However, in embodiments, the belt 602 may be constructed of non-elastic materials or a combination of elastic and non-elastic materials.

The belt 602 includes connectors 612 and 614, which are coupled to opposite terminal ends of the belt 602 and are used to secure the chest band 600 around the body of a user (the terms "connector" and "connection component" may be used interchangeably herein). For example, connectors 612 and 614 may be detachably coupled to one another in order to form a circumferential chest band around the user, a crisscross configuration over the shoulders and around the torso of the user, or any number of other configurations. In the figures, connectors 612 and 614 are depicted as complimentary ends of a snap-fit buckle. But connectors may comprise clasps, belts, hook-and-loop fasteners, ties, laces, zippers, or any other means of connection. The connectors 612 and 614 may be removably coupled to the terminal ends of the belt 602 in order to facilitate the addition and/or removal of chest band segments, as will be explained in more detail below.

Figure 22C:
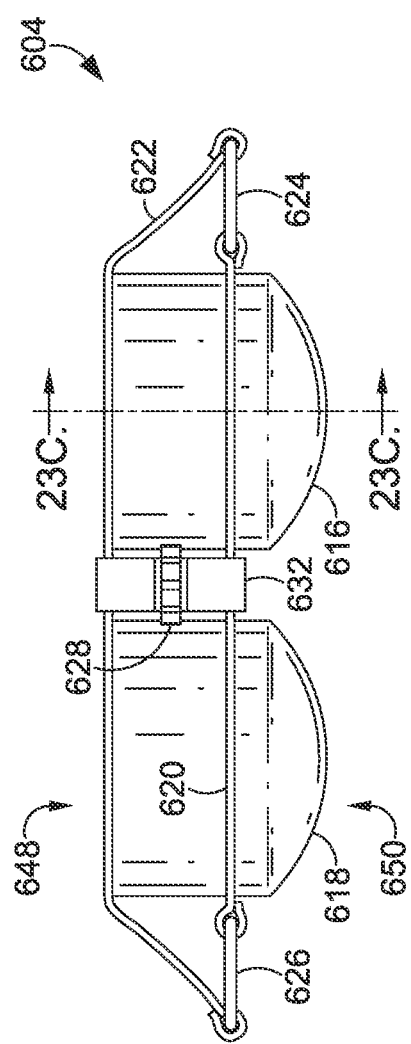
FIG. 22C is a side elevation view of the exemplary chest band segment of FIGS. 22A-B, in accordance with an exemplary embodiment hereof.

Exemplary features of the chest band segments 604, 606, 608, and 610, which are mounted on the belt 602, will now be discussed with respect to FIGS. 22A-C. FIG. 22A shows a plan view of a top side 648 of the chest band segment 604. When the user wears the chest band 600, the top side 648 of the chest band segment 604 faces away from the user (i.e. it is visible to an observer). FIG. 22B shows a plan view of a bottom side 650 of the chest band segment 604. The bottom side 650 faces the user's body when the user wears the chest band 600 (i.e. it is not visible to an observer). FIG. 22C provides a side elevation view of the chest band segment 604.

The chest band segment 604 includes a lower panel 620 and an upper panel 622 for holding vibrating elements 616 and 618 in place. The lower panel 620 is depicted as being wider than the upper panel 622, but in other exemplary embodiments, the lower panel 620 and the upper panel 622 may be the same size, or the lower panel 620 may be narrower than the upper panel 622. Any relative dimensions are included within the scope hereof. The lower panel 620 and the upper panel 622 may be comprised of any type and/or number of materials. For example, a rigid and/or semi-rigid material, such as a plastic, may be used. Additionally or alternatively, a flexible material, such as a foam, elastic, and/or other textile material, may be used. Any combination of rigid, semi-rigid, and flexible materials may be used to form the lower panel 620 and the upper panel 622. The lower panel 620 and the upper panel 622 may be comprised of the same materials or of different materials.

The lower panel 620 and the upper panel 622 are coupled to mounting components 624 and 626. In the figures, mounting components 624 and 626 are depicted as tri-bar slide adjusters. The tri-bar slide adjusters include three parallel bars for receiving and maintaining end portions of the lower panel 620 and the upper panel 622 and for adjustably mounting the chest band segment 604 on the belt 602.

For example, as shown in FIG. 20B, the belt 602 is threaded through the tri-bar slide adjusters 624 and 626. The tri-bar slide adjusters 624 and 626 provide enough resistance that the chest band segment 604 is prevented from inadvertently slipping back and forth on the belt, but at the same time, allow a user to intentionally slide the chest band segment 604 up and down the length of the belt 602 in order to position the chest band segment 604 at a desired location.

Any number of chest band segments can be mounted on the belt 602. Chest band segments may be added or removed by sliding the chest band segments on or off one end of the belt 602 or by otherwise attaching or removing the chest band segments to or from the belt 602. As mentioned, the connectors 612 and 614 may be removably coupled to the terminal ends of the belt 602 in order to facilitate sliding chest band segments on or off the belt 602. The tri-bar slide adjusters 624 and 626 are one example of a mounting component. Other mounting components may include slides, fasteners, buckles, clips, hook-and-loop fasteners, zippers, and other hardware.

Figure 29A:
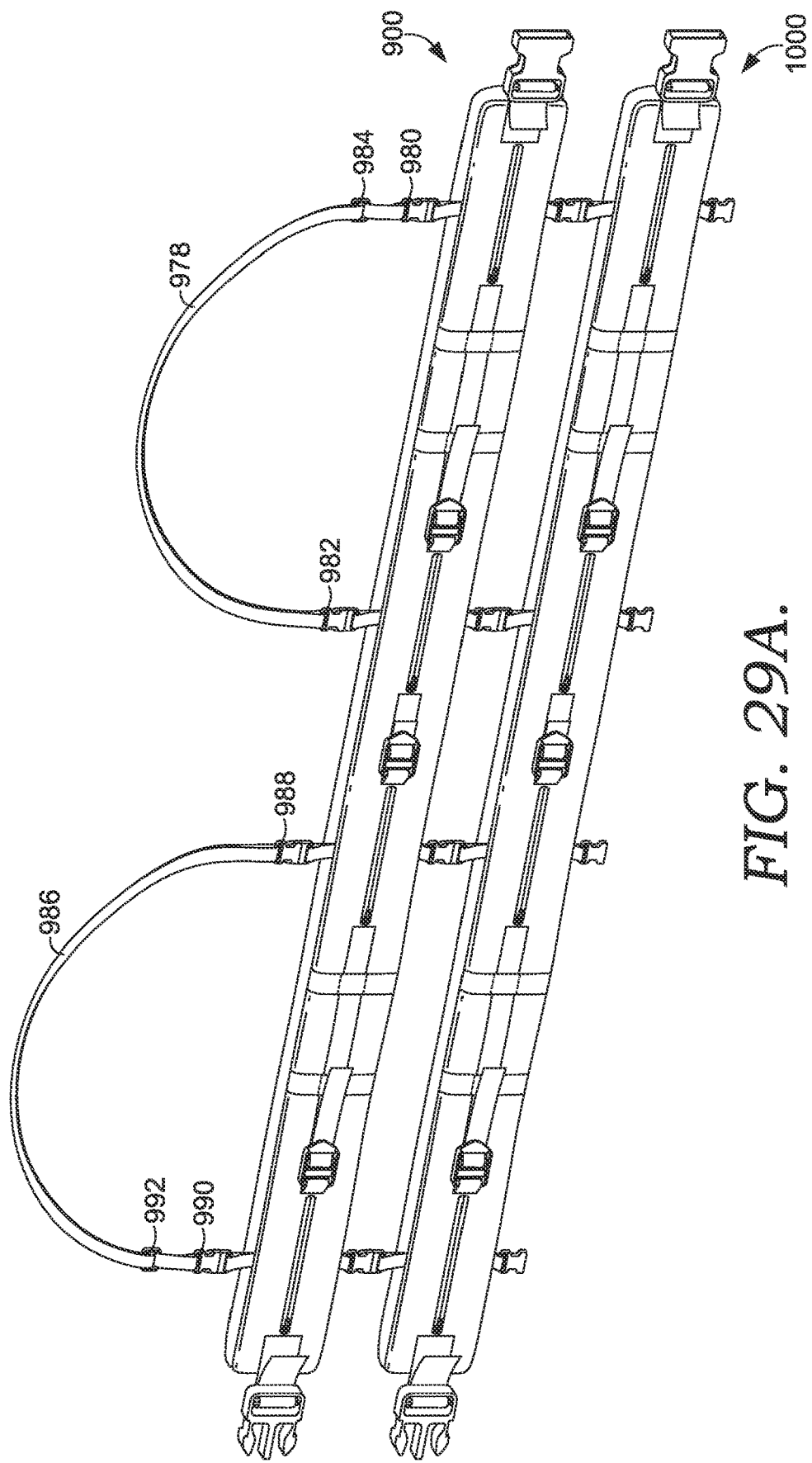
FIGS. 29A-B are front and rear, perspective views, respectively, of two exemplary apparatus units that are coupled together in parallel, in accordance with an exemplary embodiment hereof.
Figure 29B:
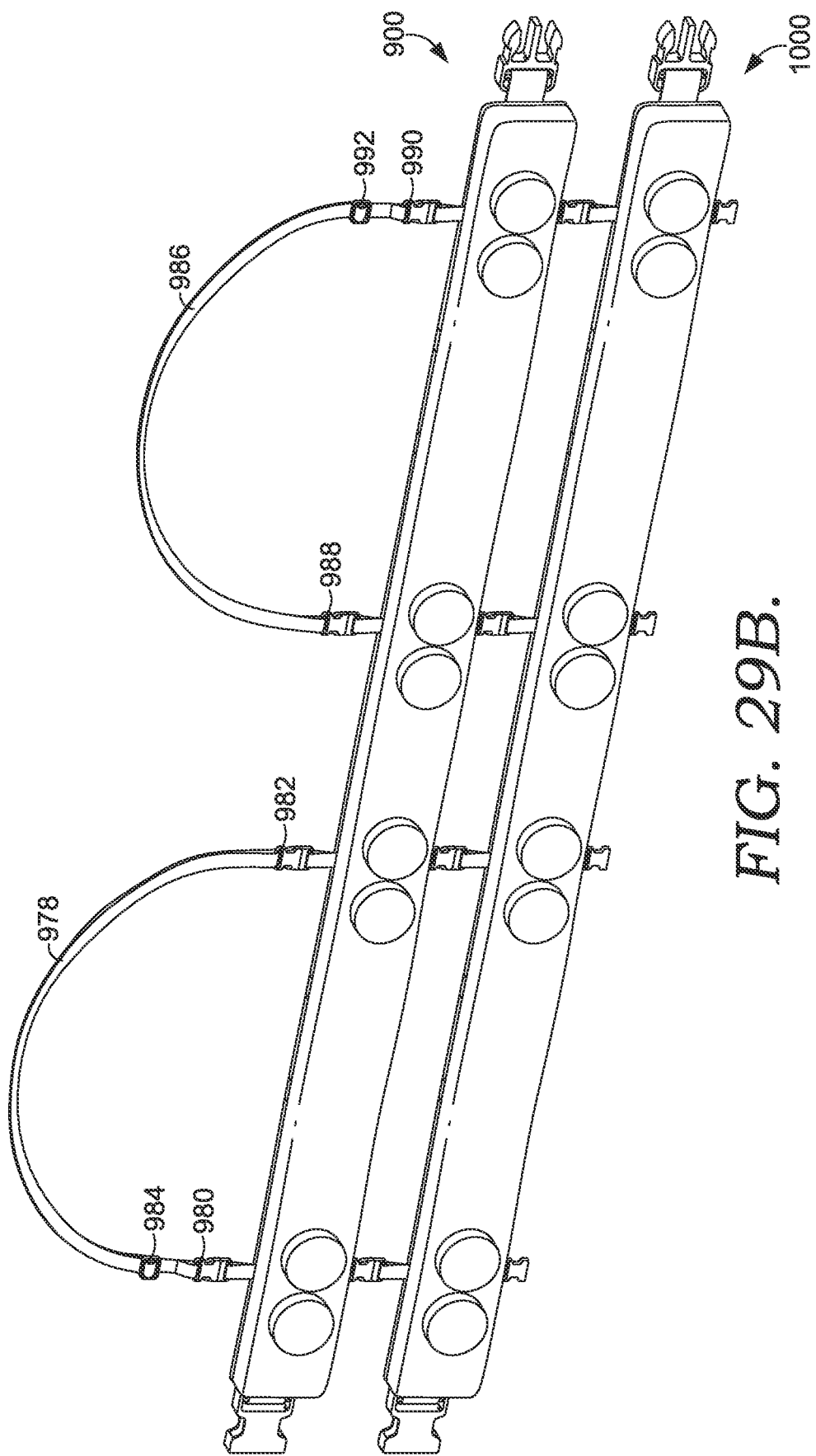

The chest band segment 604 includes connectors 628 and 630 extending laterally from the chest band segment 604, as shown in FIGS. 22A-B. These connectors are used to facilitate the multi-chest band configuration depicted in FIGS. 21A-B. As shown in FIGS. 21A-B, chest band segments 604, 606, 608, and 610, which are mounted on the belt 602, are secured via connectors to the chest band segments 704, 706, 708, and 710, which are mounted on the belt 702. In this way, the chest bands 600 and 700 are coupled to one another in a parallel fashion. Any number of belts having any number of chest band segments may be incorporated into a multi-chest-band configuration in this manner. The connectors may also be used to attach shoulder straps to a chest band. Exemplary shoulder strap configurations are discussed with respect to FIGS. 29A-B below.

In the exemplary embodiment depicted in FIGS. 22A-C, the connectors 628 and 630 are coupled to a connector strap 632 that forms a loop around the lower panel 620 and the upper panel 622. The connector strap 632 may be unsecured, such that it rotates freely around the chest band segment 604 and may be removed from the chest band segment 604, altogether. Additionally or alternatively, the connector strap may be detachably or permanently affixed to the chest band segment 604. For example, the connector strap 632 may be affixed to the chest band segment 604 via hook-and-loop fasteners, loops, buckles, sewing, glue, or any other means. Furthermore, the connectors 628 and 630 may be coupled to the chest band segment 604 by means other than the connector strap 632. For example, the connectors 628 and 630 may be directly attached to the lower panel 620 and/or upper panel 622 via hook-and-loop fasteners, loops, buckles, sewing, glue, or any other means.

The depiction of connectors 628 and 630 in the figures is exemplary only. Other types and configurations of connectors are included within the scope hereof. For example, buckles, clasps, belts, hook-and-loop fasteners, ties, laces, zippers, and any number of other connectors may be used to couple a chest band to another chest band and/or to shoulder straps.

Exemplary details regarding the vibrating elements and the manner in which they may be coupled to the chest band segment 604 will now be discussed with respect to FIGS. 23A-C. Beginning with FIG. 23A, the vibrating element 616 having a lower housing portion 638 and an upper housing portion 640 is depicted. FIG. 23B provides an exploded view of the vibrating element 616. As shown, the vibrating element 616 may include features similar to those discussed above with respect to the vibrating element 108. For example, a motor 642 is coupled to a mass 646 via a shaft 644, and this assembly is housed within the upper housing portion 640 and the lower housing portion 638. As discussed with respect to vibrating element 108, the lower housing portion 638 includes a rounded surface that serves as a percussion cap and that enhances the user's comfort during chest physical therapy. The upper housing portion 640 and the lower housing portion 638 may include a tongue 634 and groove 636 or other complimentary and/or interlocking components that facilitate securing the upper housing portion 640 and the lower housing portion 638 in place with respect to one another. As also shown, an interior of the upper housing portion 640 and the lower housing portion 638 may include a cavity for retaining the motor 642 and mass 646 assembly. Although wires and other power connections are not depicted for ease of viewing, it will be understood that the vibrating element 616 may include wires for connecting the motor 642 to a power source. Such wires may extend through one or more apertures in the housing for the vibrating element, such as one or more apertures in the upper housing portion 640. In embodiments, each vibrating element may be powered by a battery or other means such that wires need not extend outside of the housing. The configuration of the vibrating element 616 depicted in the figures is exemplary only, and it will be understood that the vibrating element 616 may include different and/or additional features, such as those discussed herein with respect to other vibrating element configurations.

FIG. 23C provides an exemplary cross-section view of the vibrating element 616 coupled to the chest band segment 604. The lower panel 620 of the chest band segment 604 may include one or more apertures for receiving and maintaining one or more vibrating elements. The lower housing portion 638 of the vibrating element 616 may be positioned adjacent to a bottom surface of the lower panel 620, with the tongue 634 extending through an aperture in the lower panel. The upper housing portion 640 may be positioned adjacent to an opposite top surface of the lower panel 620, such that the groove 636 receives the tongue 634 and the upper housing portion 640 sits between the lower panel 620 and the upper panel 622. The vibrating element may then be secured in place via any number of methods. For example, once positioned on opposing surfaces of the lower panel 620, the upper housing portion 640 may be glued to the lower housing portion 638. Additionally or alternatively, the vibrating element may be screwed in place, such as by inserting a bolt or screw through the lower housing portion 638, the lower panel 620, and the upper housing portion 640. A removable fastener like a bolt or screw allows the vibrating element to be quickly and easily decoupled from the chest band segment 604. This may be desirable for purposes of repairing and/or replacing a particular vibrating element. This may also be desirable for purposes of customizing the number of vibrating elements that a chest band segment includes.

As shown in the exemplary configuration depicted in FIG. 23C, the upper housing portion 640, which retains the motor 642, is disposed above a top surface of the lower panel 620. The lower housing portion 638, which retains the mass 646, is disposed below a bottom surface of the lower panel 620. Details regarding the vibrational force provided by vibrating elements 616 and 618 (e.g., the vibrational force that is provided as an asymmetric mass rotates about an axis corresponding to a shaft) were discussed above and are not repeated here. Additionally, the vertical configuration of the vibrating element and the pivot point that is created when the motor body and the mass are disposed on opposite sides of the chest band segment were previously discussed. It will be understood that the previous discussion of these and other features are also applicable to the vibrating elements 616 and 618 and the chest band segment 604; accordingly, these details are also not repeated here. The figures show the entirety of the motor body disposed above one surface of the lower panel 620 and the entirety of the mass disposed below an opposite surface of the lower panel 620. As used herein, the terms "disposed above" and "disposed below" mean that at least a portion of the relevant component, but not necessarily the entirety of the relevant component, is disposed above or below the specified object. Vibrating elements may be coupled to a chest band segment at a point that is not between the motor body and the mass. All such configurations are included within the scope hereof.

Any number of vibrating elements may be included on a chest band segment, and the configuration including two vibrating elements is exemplary only. A chest band segment may be configured to maintain a certain number of vibrating elements, such as one or more vibrating elements (e.g., the lower panel 620 of the chest band segment 604 may include two apertures and is therefore configured to maintain two vibrating elements). In use, the chest band segment may include the number of vibrating elements for which it is configured to receive, but it may also include fewer than such number. For example, although the chest band segment 604 is configured to maintain two vibrating elements, in use, it may include only one vibrating element.

The chest band segment 604 is substantially rectangular in shape. However, other shapes may also be utilized. For example, other shapes, such as a circle, oval, square, polygon, elongated polygon, or other shape, may be utilized. The shape of the chest band segment 604 may depend on the number of vibrating elements that are coupled to the chest band segment. For example, if only one vibrating element is coupled to a chest band segment, then the chest band segment may be a square.

In embodiments, the chest band 600 may further include one or more covers for covering at least a portion of the chest band 600. For example, each chest band segment may be individually covered such that the vibrating elements are contained within the cover. The covered chest band segments may then be mounted on the belt. Additionally or alternatively, the belt and the chest band segments may be contained within a single cover. For example, a cover may comprise a sleeve that slips over the chest band after the chest band segments have been mounted on the belt. The one or more covers may be removable to permit access to the belt, the chest band segments, and/or the vibrating elements (e.g., to permit a user to adjust the location of the chest band segments, to add or remove chest band segments, to adjust the length of the belt, and/or to perform maintenance on the vibrating elements or other components). For example, the one or more covers may include one or more clasps, belts, hook-and-loop fasteners, ties, laces, zippers, or any other means for securing the cover over the desired portion of the chest band. The cover may be adjustable, such that the length of the chest band may be increased or decreased by adjusting the cover.

Turning now to the remaining figures, additional exemplary configurations of a chest band and/or chest band segments are discussed.

FIG. 24A provides a front, perspective view of an exemplary vibration band 800, and FIG. 24B provides a rear, perspective view of the exemplary vibration band 800. FIG. 24C provides a side elevation view of the vibration band 800. The vibration band 800 includes a band 802 to which vibrating elements 812, 814, 816, 818, 820, 822, 824, and 826 are coupled. Thus, the vibration band 800 is an exemplary embodiment of a chest band comprising one chest band segment that includes vibrating elements, as discussed above. For example, the band 802 is an exemplary chest band segment, and the vibrating elements 812, 814, 816, 818, 820, 822, 824, and 826 may have features similar to those previously discussed with respect to vibrating elements. The term "vibration band" is introduced here for ease of reference to the combination of a band and one or more vibrating elements.

In the exemplary configuration depicted in FIGS. 24A-C, the band 802 is elongated in shape. As used herein, the term "elongated" is used to describe an object that has a length exceeding its width. For example, the ratio of the length to width of the band 802 may be between approximately 5:1 and 30:1. In other exemplary configurations, the band 802 may have a different shape, such as non-elongated shape. In the exemplary configuration depicted in FIGS. 24A-C, the band 802 has a width that is approximately the same as, or slightly wider than, the width of the vibrating elements. But as shown in FIG. 1, for example, the width of the band 802 may be significantly greater than the width of a vibrating element. The band 802 may be constructed of elastic materials, non-elastic materials, or a combination of elastic and non-elastic materials.

The band 802 has a first terminal end 804 and a second terminal end 806, which are at opposite ends of a longitudinal axis of the band 802. The band 802 has a top surface 808 and an opposing bottom surface 810. The top surface 808 is the surface that faces away from a user's body when the user wears the vibration band 800, and the bottom surface 810 is the surface that faces toward the user's body in an in-use configuration.

The vibrating elements 812, 814, 816, 818, 820, 822, 824, and 826 are disposed between the first terminal end 804 and the second terminal end 806 of the band 802. In the exemplary embodiment depicted in the figures, the vibrating elements are disposed in pairs. For example, vibrating elements 812 and 814 constitute a first pair, vibrating elements 816 and 818 constitute a second pair, vibrating elements 820 and 822 constitute a third pair, and vibrating elements 824 and 826 constitute a fourth pair. The vibrating elements in each pair are disposed relatively close to one another (e.g., the distance between the two vibrating elements is less than the width of a single vibrating element). The pairs are uniform, in that the space occupied by each pair on the band is approximately the same (i.e. the total width of the two vibrating elements, including the space between them, is approximately the same for each pair). The pairs of vibrating elements are spaced along the longitudinal axis of the band 802. In the figures, the pairs are spaced unevenly, with the distance between the first pair and the second pair being greater than the distance between the second pair and the third pair, and with the distance between the third pair and the fourth pair being approximately the same as the distance between the first pair and the second pair. This uneven spacing may be desirable for providing percussive chest therapy at particular regions of a user's body.

It will be understood that the depicted configuration is exemplary only and that in embodiments, the vibrating elements need not be disposed in pairs. For example, the vibrating elements may be disposed in groupings of more than two vibrating elements. The groupings may be uniform, non-uniform, or a combination of the two. Additionally or alternatively, the vibrating elements may not be disposed in groups, at all. Furthermore, the number of vibrating elements depicted is exemplary only. Any number of vibrating elements is included within the scope hereof. Accordingly, one or more vibrating elements may be spaced evenly and/or unevenly, in groupings and/or not in groupings, along the band 802.

Exemplary details regarding the vibrating elements and the manner in which they may be coupled to the band 802 will now be discussed with respect to FIGS. 25A-E. Beginning with FIG. 25A, an exploded view of the vibrating element 816 is provided. As shown, the vibrating element includes a motor 828 and mass 830 assembly that is housed within a vibrating element housing 834, similar to the exemplary vibrating element configurations previously discussed above. The vibrating element housing may include one or more pieces. For example, the housing 834 for vibrating element 816 includes four quadrants 836, 838, 840, and 842 that are sandwiched by two end caps 844 and 846. The various pieces may be assembled and held in place with respect to one another via bolts and nuts, as discussed in more detail below.

An interior portion of the vibrating element housing 834 includes a cavity for retaining the motor 828 and mass 830 assembly. Although wires and other power connections are not depicted for ease of viewing, it will be understood that the vibrating element 816 may include wires for connecting the motor 828 to a power source. Such wires may extend through one or more apertures in the housing for the vibrating element, such as the apertures depicted in the end caps 844 and 846. In embodiments, each vibrating element may be powered by a battery or other means such that wires need not extend outside of the housing. The configuration of the vibrating element 816 depicted in the figures is exemplary only, and it will be understood that the vibrating element 816 may include different and/or additional features, including those discussed herein with respect to other vibrating element configurations.

Figure 25A:
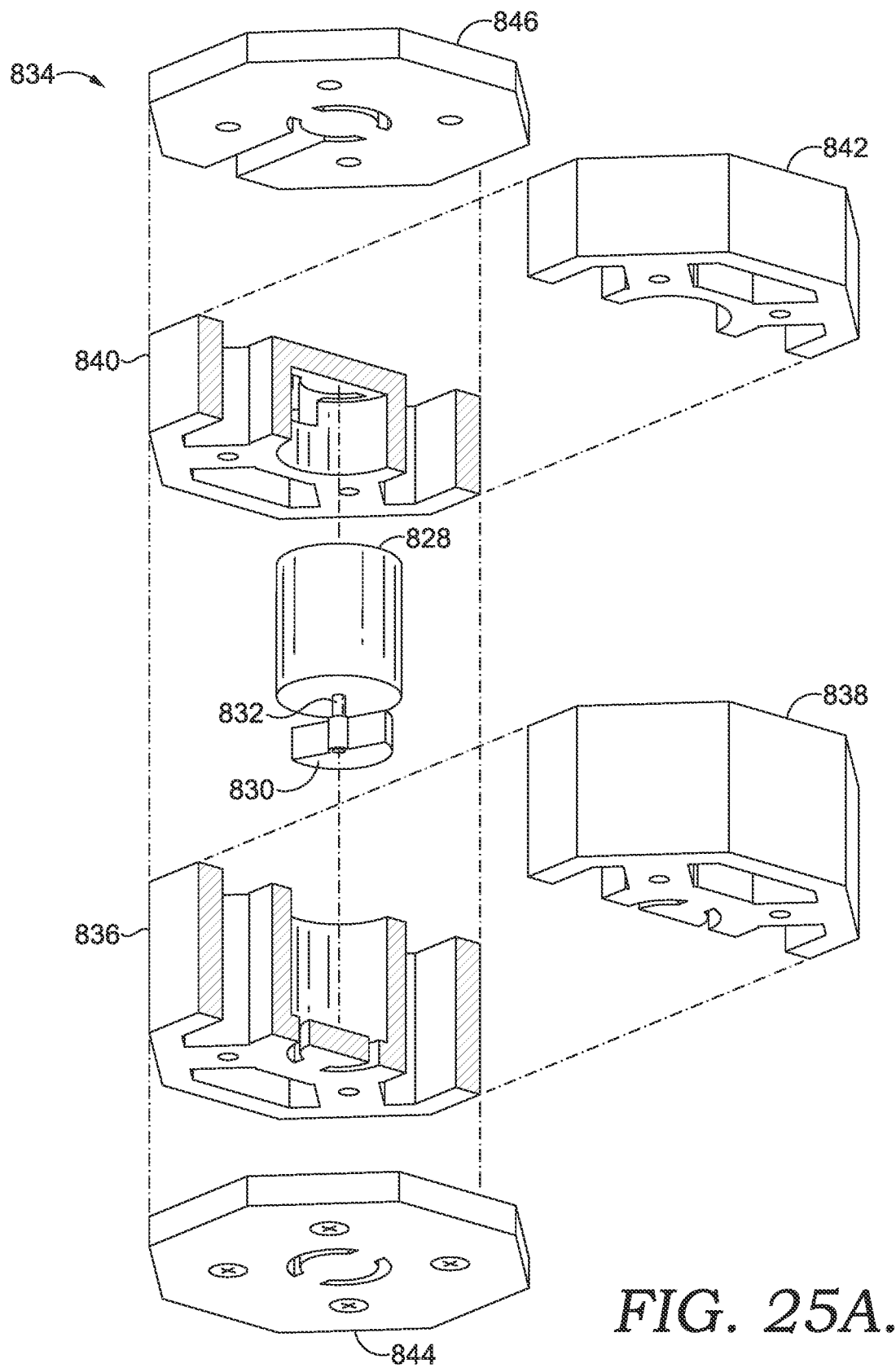
FIG. 25A is an exploded view of an exemplary vibrating element, in accordance with an exemplary embodiment hereof.
Figure 25C:
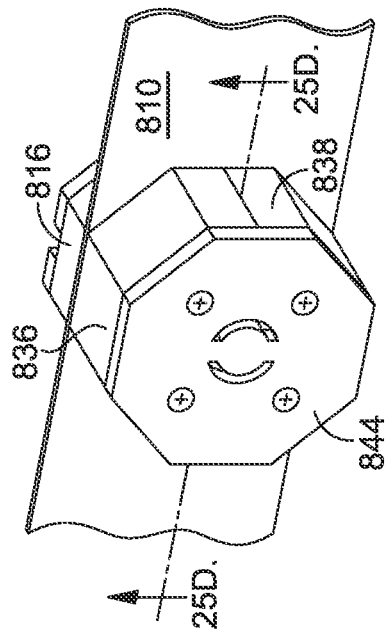
FIGS. 25B-C are enlarged front and rear, perspective views, respectively, of a portion of the exemplary vibration band of FIGS. 24A-B, in accordance with an exemplary embodiment hereof.
Figure 25E:
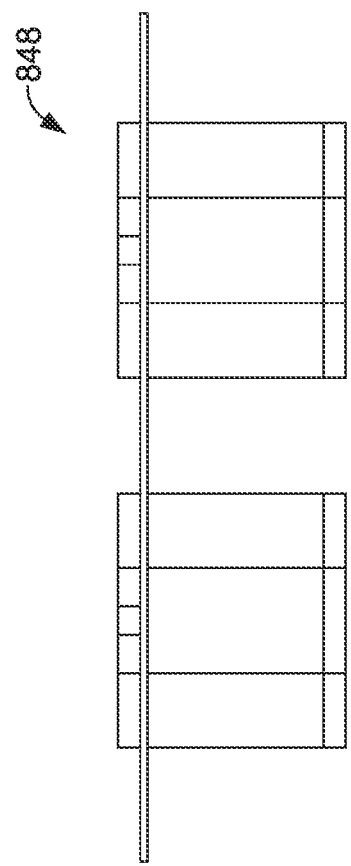
FIG. 25E is a side elevation view of a portion of an exemplary vibration band, in accordance with an exemplary embodiment hereof.
Figure 25B:
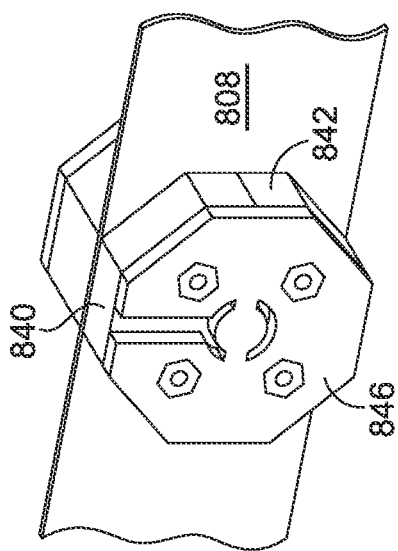
Figure 25D:
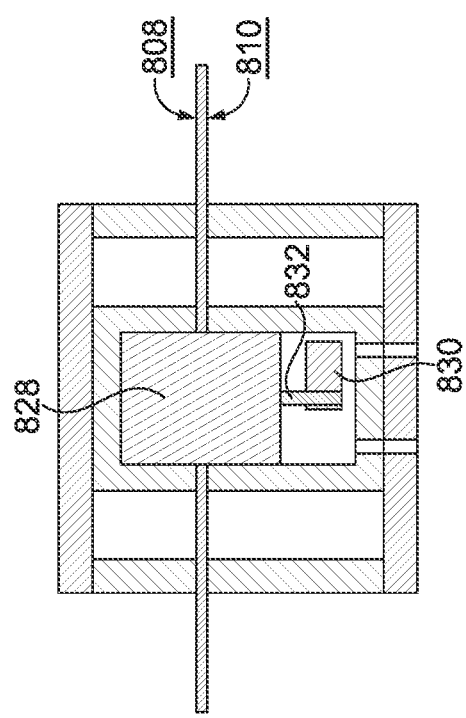
FIG. 25D is a cross-section view of the portion of the exemplary vibration band shown in FIG. 25C, in accordance with an exemplary embodiment hereof.

FIGS. 25B-D depict an exemplary manner in which vibrating element 816 is coupled to the band 802. As shown, quadrants 836 and 838 may be positioned adjacent to the bottom surface 810 of the band 802, and quadrants 840 and 842 may be positioned adjacent to the top surface 808 of the band 802. The band 802 may include an aperture through which the motor 828 and mass 830 assembly extends when the four quadrants are positioned in this manner. Although not pictured, the four quadrants may include tongues and grooves or other complimentary and/or interlocking components that facilitate securing the four quadrants in place with respect to one another and the band 802, similar to the configuration discussed above with respect to FIGS. 22-23. End caps 844 and 846 may sandwich the four quadrants, as shown. In the figures, the housing 834 and the enclosed motor 828 and mass 830 assembly are coupled to the band 802 via bolts that extend through the end cap 846, through the quadrants, and through the end cap 844, and that are secured in place by nuts. The exterior surface of the end cap 844 may include recessed portions configured to receive the nuts so that the nuts sit flush with the end cap 844. This may reduce the risk of the nuts catching on surrounding fabric. The exterior surface of the end cap 846 may similarly include recessions for the heads of the bolts. The nuts and bolts depicted in the figures are exemplary only, and it will be understood that vibrating elements may be coupled to the band 802 in many other ways, including other removable and nonremovable fasteners.

As shown in the exemplary configuration depicted in FIG. 25D, the motor 828 and mass 830 are disposed on opposite sides of the band 802, with the motor 828 being above the band 802 and the mass 830 and shaft 832 being below the band 802. Details regarding the vibrational force provided by vibrating element 816 (e.g., the vibrational force that is provided as an asymmetric mass rotates about an axis corresponding to a shaft) were discussed above and are not repeated here. Additionally, the vertical configuration of the vibrating element and the pivot point that is created when the motor body and the mass are disposed on opposite sides of the band were previously discussed. It is understood that the previous discussion of these and other features are also applicable to the vibrating element 816 and the band 802; accordingly, these details are also not repeated here.

The vibrating element housing 834 and the manner in which it is coupled to the band 802 in FIGS. 25B-D is exemplary only. The vibrating element housing 834 has the shape of an octagonal prism, but other housing shapes are included within the scope hereof. The vibrating element housing 834 includes six different pieces (four quadrants and two end caps), but a larger or smaller number of pieces may be used. For example, the housing may include two halves and two end caps (e.g., quadrants 836 and 840 may be a single piece and quadrants 838 and 842 may be a single piece). In this instance, the housing may be secured to the band 802 in the configuration 848 shown in FIG. 25E, with an end cap disposed on one side of a band and the remainder of the housing disposed on the other side of the band. In this instance, the motor and mass are disposed on the same side of the band. Such configurations are included within the scope hereof. Accordingly, the vibrating element housing 834 may be configured in any number of ways, and the vibrating element housing 834 may be secured to the band 802 in any number of ways.

The vibration band 800 may be secured around a user's body in order to provide percussive therapy. For example, the vibration band 800 may be secured around a user's torso in order to provide percussive chest therapy. The vibration band 800 may be used to provide percussive therapy at other portions of a user's body, as well. The vibration band 800 may be sized according to the area of the body at which percussive therapy will be provided. Releasable connection assemblies, such as buckles, may be secured to the terminal ends of the band 802 in order to facilitate securing the vibration band 800 around a user's body. Additionally or alternatively, the vibration band 800 may be paired with a cover that facilitates securing the vibration band 800 around a user's body and provides additional features. An exemplary cover is described directly below.

In FIGS. 26A-B, an apparatus unit 900 that includes a cover 902 enclosing the vibration band 800 is shown. FIG. 26A provides a front, perspective view of the exemplary cover 902, which shows the side of the cover 902 that faces away from a user's body when the user wears the apparatus unit 900. FIG. 26B provides a rear, perspective view of the exemplary cover 902, which shows the side of the cover 902 that faces toward the user's body when the user wears the apparatus unit 900. At a high level, the cover 902 is configured to receive the vibration band 800. The cover 902 may include one or more pockets that correspond to the one or more vibrating elements on the vibration band. For example, the cover 902 includes pockets 942, 944, 946, 948, 950, 952, 954, and 956, each of which is configured to receive a vibrating element.

In the exemplary configuration depicted in FIGS. 26A-B, the cover 902 is elongated in shape. For example, the ratio of the length to width of the cover 902 may be between approximately 5:1 and 30:1. However, the cover 902 may also have a different shape, such as non-elongated shape. In the figures, the width of the cover 902 corresponds to the width of the band 802. For example, the width of the cover 902 may be approximately one to two times the width of the band 802.

The cover 902 has a first terminal end 904 and a second terminal end 906, which are at opposite ends of a longitudinal axis of the cover 902. The pockets 942, 944, 946, 948, 950, 952, 954, and 956 are disposed between the first terminal end 904 and the second terminal end 906. In the exemplary embodiment depicted in the figures, the spacing between the pockets corresponds to the spacing between the vibrating elements on the band 802. For example, the pockets are disposed in uniform pairs that are spaced unevenly along a longitudinal axis of the cover 902. As discussed with respect to the vibrating elements, the pockets may be spaced evenly and/or unevenly, in groupings (which may be uniform and/or non-uniform) and/or not in groupings, along the cover 902.

The pockets are constructed on one side of the cover 902, and an opposite side of the cover 902 includes closeable openings 934, 936, 938, and 940. Each opening provides access to a vibrating element cavity associated with a pair of pockets. For example, the closeable opening 934 provides access to a vibrating element cavity associated with pockets 942 and 944. The closeable openings may be located on other portions of the cover 902 and may differ in number and size from those shown in the figures. Additional details regarding the construction of the cover 902, the pockets 942, 944, 946, 948, 950, 952, 954, and 956, the vibrating element cavities, and the closeable openings 934, 936, 938, and 940 will be provided with respect to FIGS. 27A-E below.

The cover 902 includes a releasable connection assembly that may be used to secure the unit 900 around a user's body (e.g., a user's torso) and form a circumferential band. The releasable connection assembly includes a terminal-end connector 908 coupled to the first terminal end 904 and a terminal-end connector 910 coupled to the second terminal end 906. The terminal-end connectors 908 and 910 may be releasably connectable to one another. As used herein, the term "releasably connectable" refers to components that are intended to be connected and disconnected repeatedly without degrading the structural integrity of the components. For example, buckles, clasps, belts, hook-and-loop fasteners, ties, laces, and zippers are examples of releasable connection assemblies that include connectors that are releasably connectable to one another. In the figures, terminal-end connectors 908 and 910 are complimentary ends of a snap-fit buckle. However, other types of releasable connection assemblies, included those listed above, are included within the scope hereof. Furthermore, the terminal ends 904 and 906 may be non-releasably connectable. As used herein, the term "non-releasably connectable" refers to components that cannot be connected and disconnected repeatedly without degrading the structural integrity of the components. For example, the terminal ends 904 and 906 may be glued or stitched together such that the unit 900 is permanently or semi-permanently configured as a circumferential band.

The cover also includes length-adjustment mechanisms 928, 930, and 932 for adjusting a length of the unit 900 (i.e. adjusting a distance between the first terminal end 904 and the second terminal end 906) and providing a customized fit for a particular user. For example, a user with a relatively small torso may shorten the length of the unit 900, such that when the unit is planar (i.e. is lying flat, as shown in FIGS. 26A-B and FIGS. 28A-B), the distance between the first terminal end 904 and the second terminal end 906 is reduced. FIGS. 28A-B show the unit 900 after the length-adjustment mechanisms 928, 930, and 932 have been used to shorten the length of the unit 900. In the figures, the length-adjustment mechanisms 928, 930, and 932 are adjustable straps with buckles that are coupled to an exterior surface of the cover 902. Other types of length-adjustment mechanisms, as well as length-adjustment mechanisms that are coupled to other surfaces of the cover 902, are also included within the scope hereof. For example, the length-adjustment mechanisms may include snaps, clasps, zippers, elastic, drawstrings, and other mechanisms. In an example, the cover 902 may be constructed of an elastic material and/or the cover may include elastic bands so that the length of the unit 900 in a relaxed state is relatively short. When the cover is placed on a user's body, the elastic may stretch to fit around the user's body and provide a snug fit. Length-adjustment mechanisms may be located in an interior portion of the cover 902.

In the figures, each length-adjustment mechanisms is located between two pairs of pockets on a side of the cover 902 that is generally opposite the side of the cover 902 on which the pockets are constructed. This allows a user to adjust the spacing between the pairs of pockets and the corresponding vibrating elements and thus position the vibrating elements to provide percussive force at a desired location on the user's body. The length-adjustment mechanisms may be uniform or non-uniform. For example, as shown in the figures, length-adjustment mechanisms 928 and 932 have longer straps than length-adjustment mechanism 930 does, and length-adjustment mechanisms 928 and 932 thus facilitate a greater degree of length adjustment than length-adjustment mechanism 930 does. Accordingly, in the figures, the length-adjustment mechanisms are non-uniform. The degree of length adjustment that is provided by a particular length-adjustment mechanism may correspond to the distance between the two pairs of pockets between which the length-adjustment mechanism is located. For example, the distance between the pair of pockets 946 and 948 and the pair of pockets 950 and 952 is smaller than the distance between the pair of pockets 942 and 944 and the pair of pockets 946 and 948. Accordingly, the length-adjustment mechanism 928 provides for a greater degree of length adjustment than does length-adjustment mechanism 930.

The cover 902 also includes interspaced connectors 912, 914, 916, 918, 920, 922, 924, and 926 that are positioned along a longitudinal axis of the cover 902 between the first terminal end 904 and the second terminal end 906 and that extend laterally from the cover 902 in a direction that is perpendicular to the longitudinal axis of the cover and that is also perpendicular to a direction in which the pockets protrude. These interspaced connectors may be configured to releasably connect to a mating connector, such as a mating connector coupled to another apparatus unit. For example, in FIGS. 29A-B, the interspaced connectors are used to releasably connect the unit 900 to another unit 1000. As previously discussed, the ability to couple one or more units in parallel provides for the application of a percussive force across a larger area of a user's body and facilitates customization for a particular user.

The interspaced connectors may also be used to connect shoulder straps to the unit 900. For example, in FIGS. 29A-B, the interspaced connectors are used to releasably connect shoulder straps 978 and 986 to the unit 900 via shoulder connectors 980, 982, 988, and 990. The shoulder straps may include length-adjustment mechanisms 984 and 992 for adjusting the length of the shoulder straps and providing a customized fit for a particular user.

The configuration and number of interspaced connectors in the figures is exemplary only. For example, the cover 902 may include an interspaced connector comprising a zipper that runs along the length of the cover 902 between the first terminal end 904 and the second terminal end 906. As another example, the cover 902 may include eyelets through which a lace is threaded and used to connect the unit 900 to another unit. Accordingly, buckles, clasps, belts, hook-and-loop fasteners, ties, zippers, laces, and any number of other connectors may be used as one or more interspaced connectors for releasably connecting the unit 900 to another unit and/or to shoulder straps. Additionally or alternatively, the unit 900 may be non-releasably connected to another unit and/or to shoulder straps.

Figure 27A:
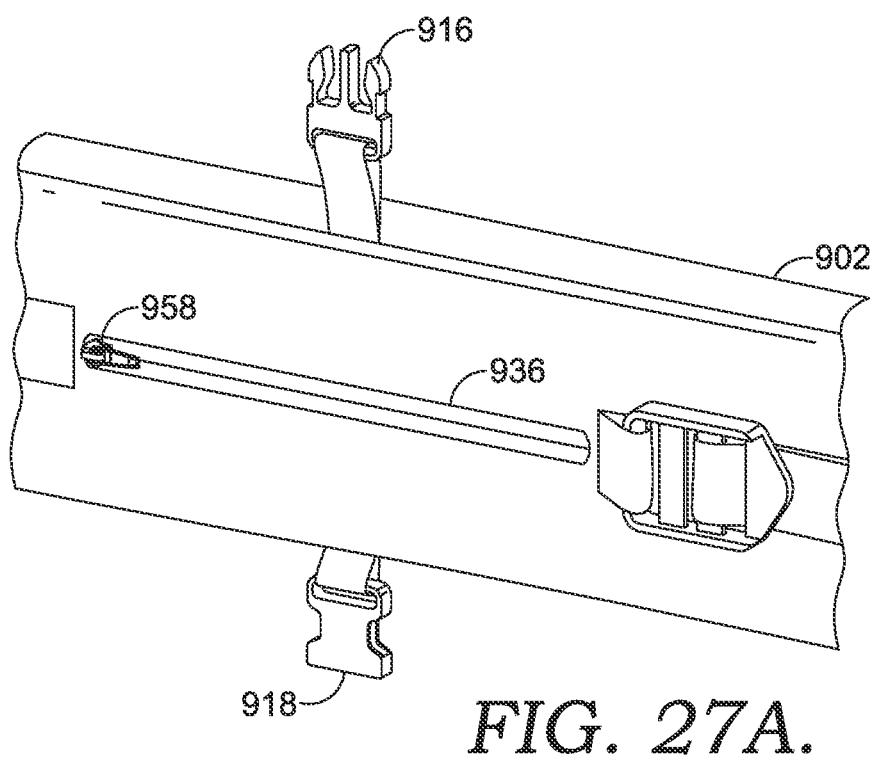
FIGS. 27A-B are enlarged perspective views of a portion of a cover of the exemplary apparatus unit of FIGS. 26A-B, in accordance with an exemplary embodiment hereof.
Figure 27B:
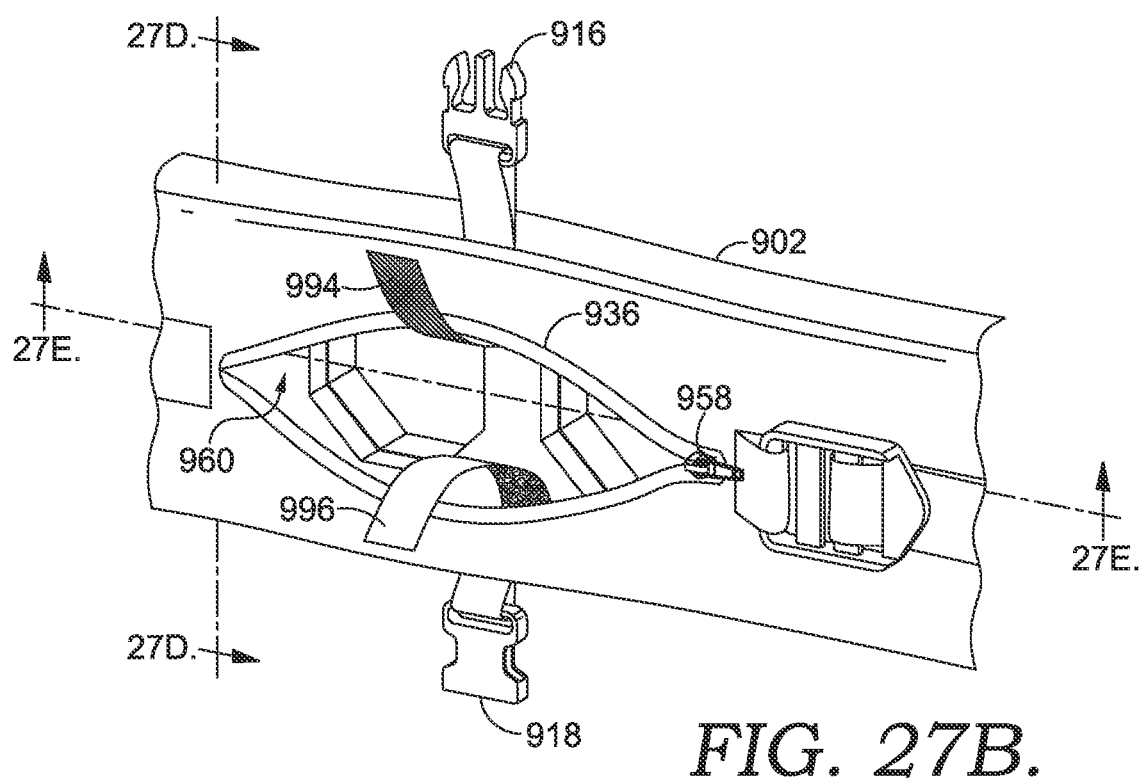
Figure 27C:
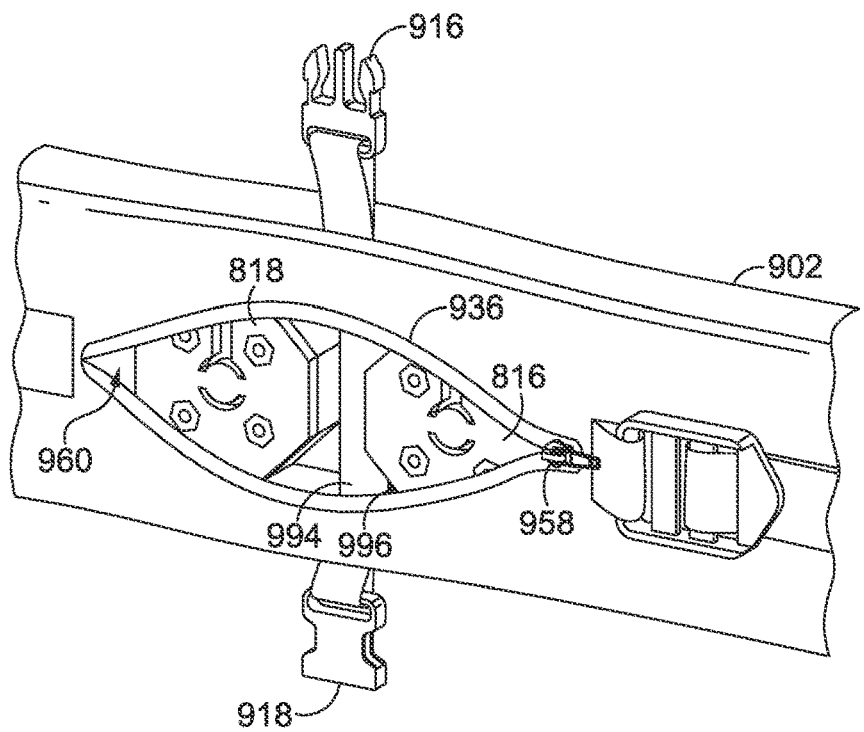
FIG. 27C is an enlarged perspective view of a portion of the exemplary apparatus unit of FIGS. 26A-B, in accordance with an exemplary embodiment hereof.

Turning now to FIGS. 27A-E, a more detailed discussion of the construction of the cover 902 will be provided. FIGS. 27A-C provide an enlarged, front, perspective view of a portion of the cover 902. In FIG. 27A, the closeable opening 936 is in a closed position, and in FIGS. 27B-C, the closeable opening 936 is in an open position. An opening and closing mechanism 958 facilitates the transition between the open and closed positions and secures the opening in the closed position. In the figures, the opening and closing mechanism 958 is depicted as a zipper, but many other mechanism are included within the scope hereof. For example, buckles, clasps, belts, hook-and-loop fasteners, ties, and laces may be used as the opening and closing mechanism 958.

FIG. 27B shows the cover 902 having an empty interior, while FIG. 27C shows the vibration band 800 enclosed within the cover 902. As shown in FIG. 27B, the closeable opening 936 provides access to a vibrating element cavity 960 associated with pockets 946 and 948 (the pockets that are opposite the closeable opening 936). Each of the pockets is configured to receive a vibrating element. For example, the shape of the interior portion of the pockets corresponds to the shape of the vibrating elements. The vibration band 800 may be inserted into the cover 902 (e.g., inserted into one of the closeable openings and then guided along the length of the cover, using the other closeable openings as access points), and each vibrating element may be inserted into a corresponding pocket. Releasable connectors 994 and 996 may be used to secure the vibration band 800 in place and prevent the vibrating elements from slipping out of the pockets and/or the band 802 from sliding. In the figures, the length of the band 802 is comparable to the length of the cover 902. But as discussed herein with respect to additional configurations, the band 802 may be comprised of one or more segments. For example, the band 802 may be comprised of four smaller segments, each of which includes one of the pairs of vibrating elements. Each such segment may be inserted into the cover 902 through the closeable openings. Additionally or alternatively, the unit 900 may not include a vibration band, at all. The vibrating elements may be standalone components that are disposed directly in the pockets and secured in place.

Figure 27D:
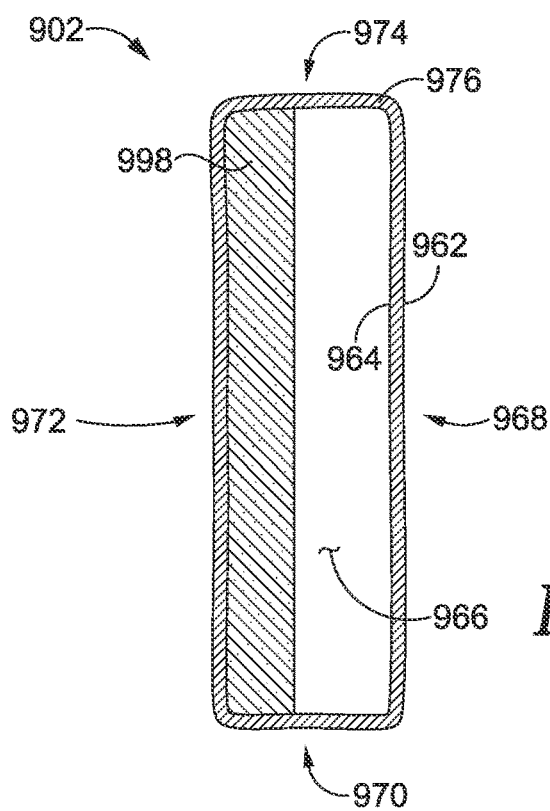
FIGS. 27D-E are cross-section views of the portion of the cover shown in FIG. 27B, in accordance with an exemplary embodiment hereof.
Figure 27E:
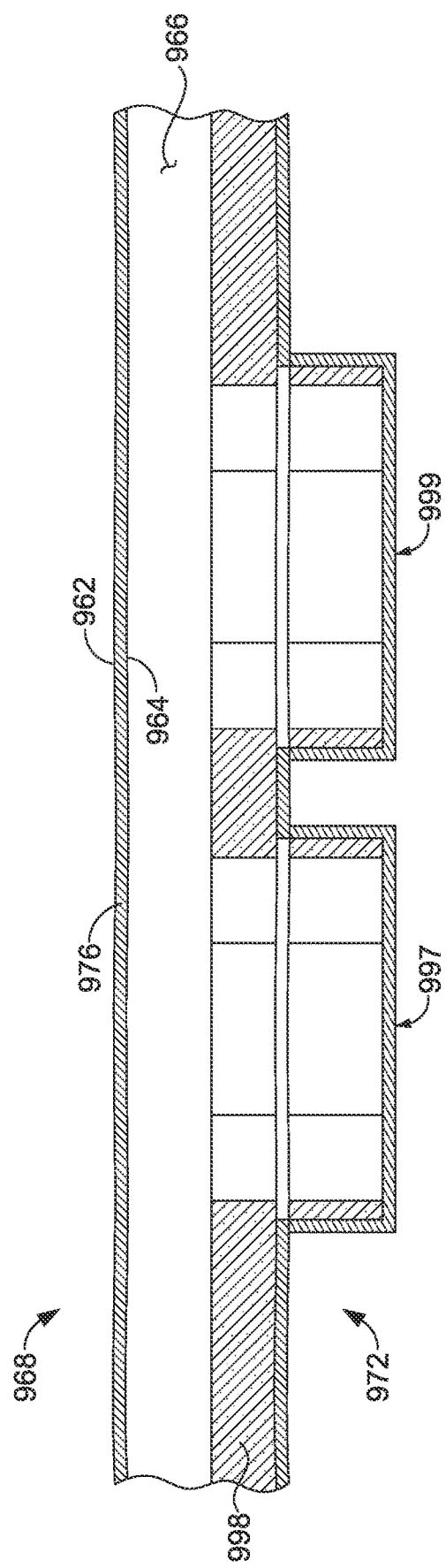

FIGS. 27D-E provide cross-section views of the cover 902. The cover 902 is comprised of a tubular sleeve, which includes a tubular wall 976 that circumscribes a space 966 that is configured to receive the vibration band 800. The tubular wall 976 may be one continuous wall, or it may be several walls sewn together. In the figures, the tubular sleeve has a rectangular cross-section, but any other cross-section shape is included within the scope hereof. The wall 976 may have several different sides, including a front side 968 that faces away from the user in an in-use configuration, a rear side 972 that faces toward the user in an in-use configuration, a bottom side 970, and a top side 974. The wall 976 has an exterior surface 962 that faces away from the space 966 and an interior surface 964 that faces towards the space 966.

The front side 968 includes the closeable openings described above. The closeable openings extend entirely through the tubular wall from the exterior surface 962 to the interior surface 964 and fluidly connect with the space 966. The interspaced connectors are coupled to the bottom side 970 and top side 974 of the wall 976.

The rear side 972 is generally opposite the front side 968 and includes the pockets described above. The pockets correspond to a portion of the wall 976 that protrudes away from the space 966 to form a recess configured to receive a vibrating element, as shown in FIG. 27E. The portion of the tubular wall 976 that protrudes away from the space 966 may include a non-slip material on the exterior surface 962 of the tubular wall 976. For example, the portions 997 and 999 of the exterior surface 962 of the tubular wall 976 may include a non-slip material, such as neoprene. The direction in which the tubular wall 976 protrudes may be substantially perpendicular to the direction in which the interspaced connectors extend from the tubular wall 976. This configuration ensures that when two units are connected in parallel, the pockets of both units are flush with a user's body.

A padding layer 998 may line the tubular wall along the entire length of the cover 902. Additionally or alternatively, the padding layer 998 may line the tubular wall only in portions of the cover corresponding to the pockets (e.g., extending 1-2 inches on either side of a pair of pockets). Including the padding layer 998 in this portion of the cover may help stabilize the vibrating elements (e.g., maintain them in a vertical position). In some instances, the recesses configured to receive the vibrating elements may also be lined with padding. The padding may enhance the comfort of the user during percussive therapy. For example, the padding may prevent the hard housing of the vibrating elements from causing discomfort, while still allowing the percussive force to reach the user's body. Accordingly, the material for the padding may be selected so that the vibrational force provided by the vibrational elements is not overly dampened. The remainder of the tubular wall may not be lined with padding in order to reduce bulk and facilitate length adjustments. The padding layer 998 may include foam or another material.

Figure 30A:
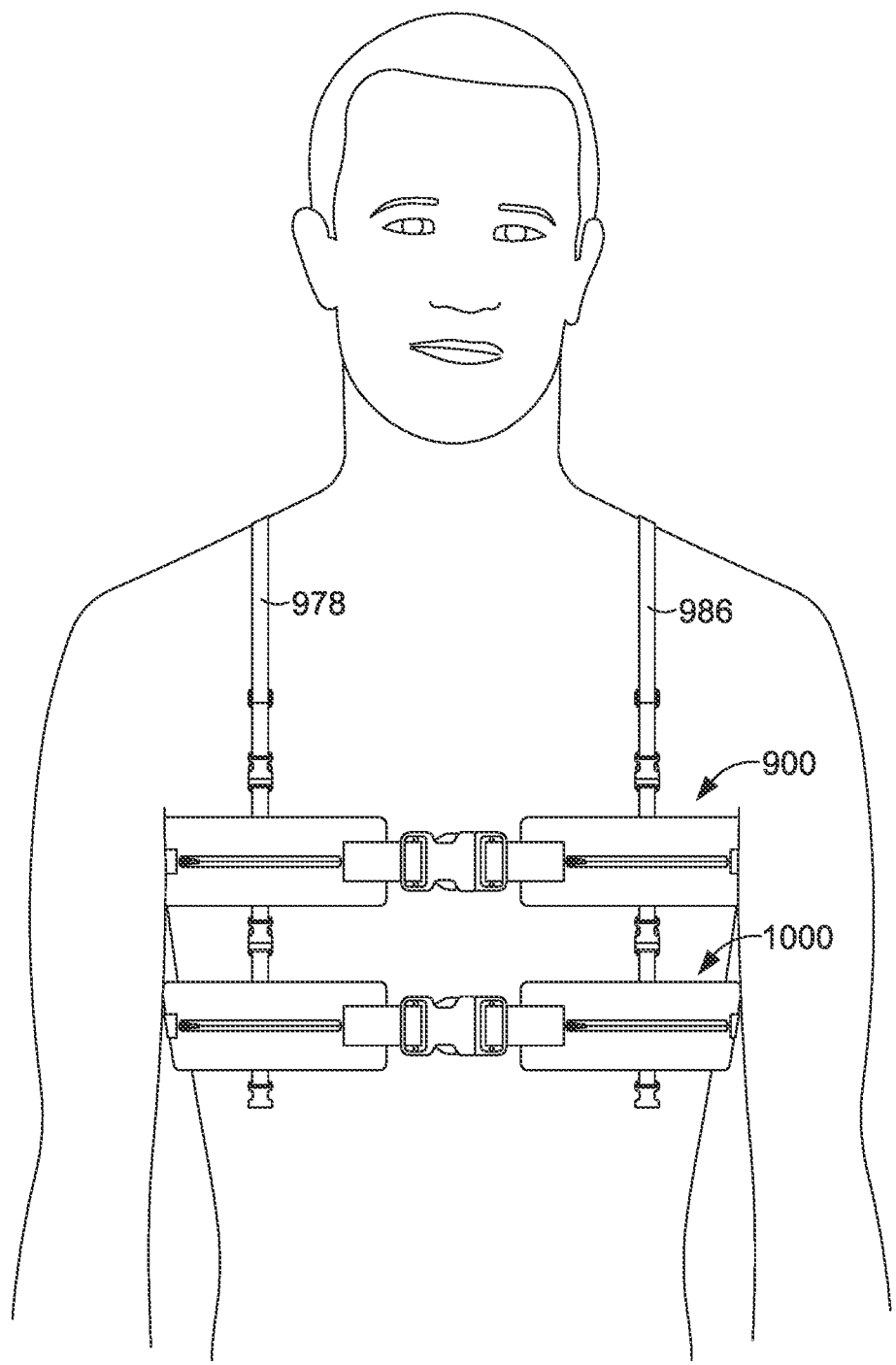
FIGS. 30A-B are front and rear, perspective views, respectively, of two exemplary units that are coupled together in parallel being worn by a user, in accordance with an exemplary embodiment hereof.
Figure 30B:
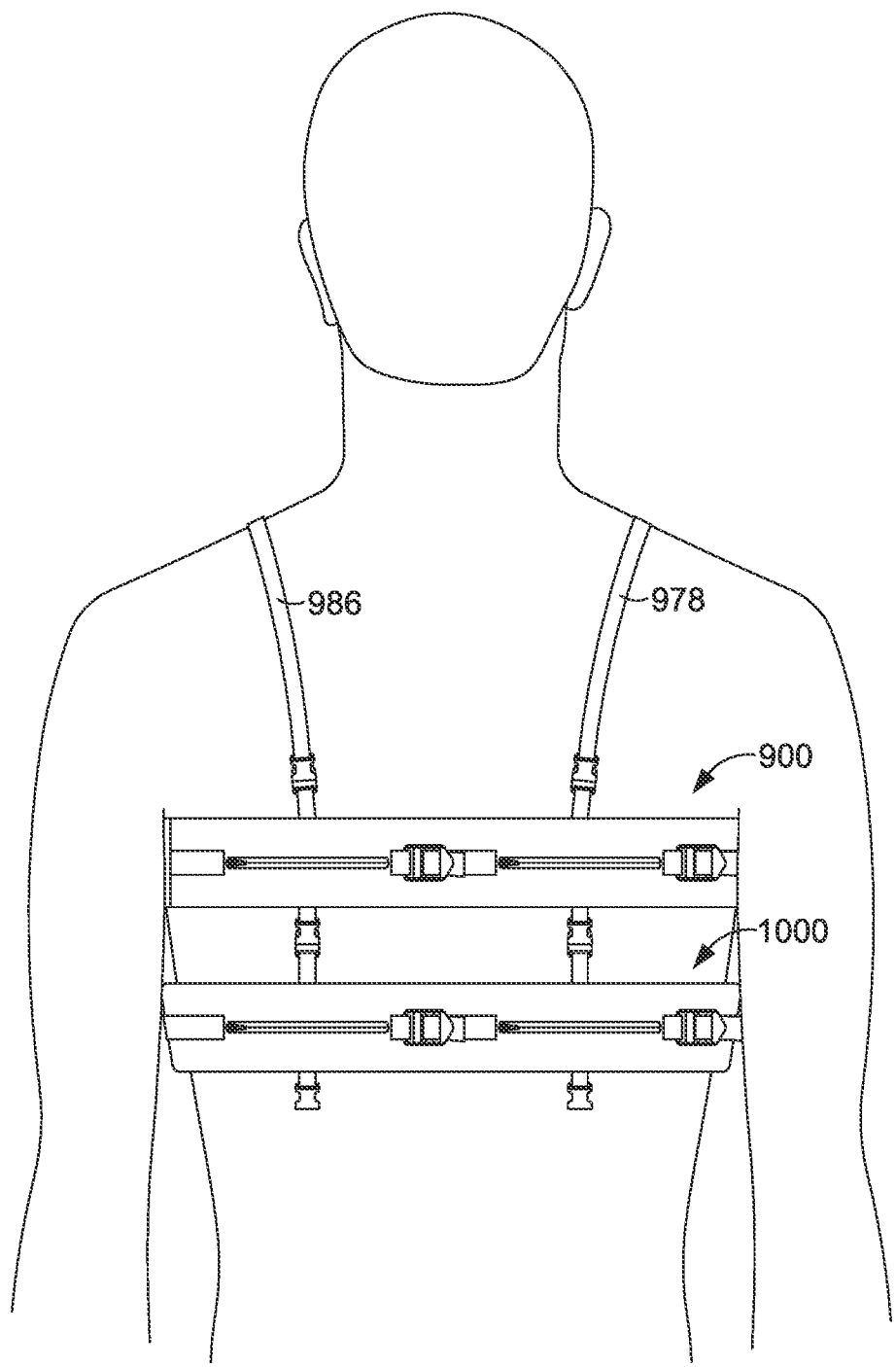
Figure 31A:
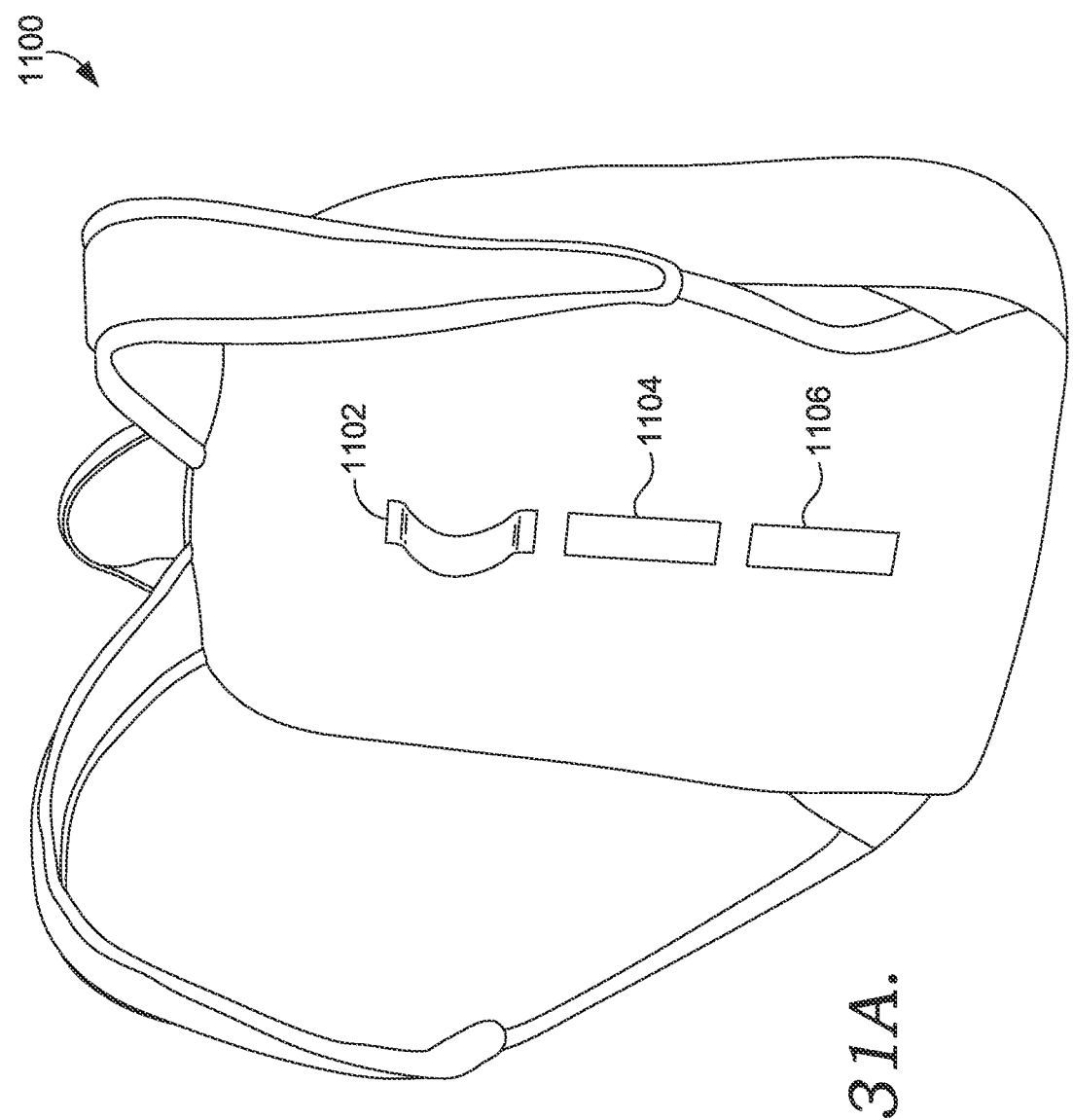
FIG. 31A is a rear, perspective view of an exemplary wearable pack, in accordance with an exemplary embodiment hereof.
Figure 31B:
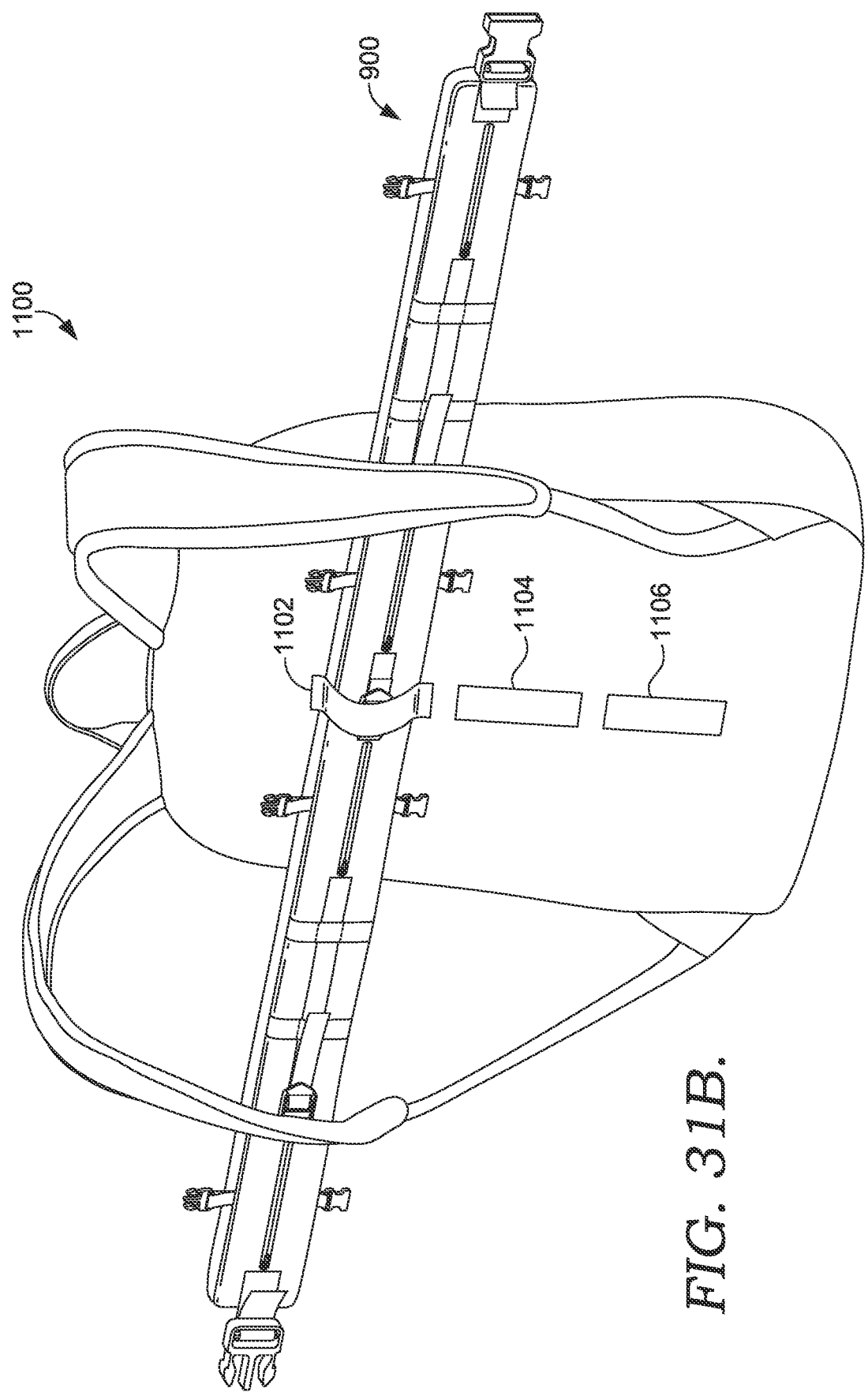
FIG. 31B is a rear, perspective view of an exemplary apparatus unit coupled to an exemplary wearable pack, in accordance with an exemplary embodiment hereof.
Figure 31C:
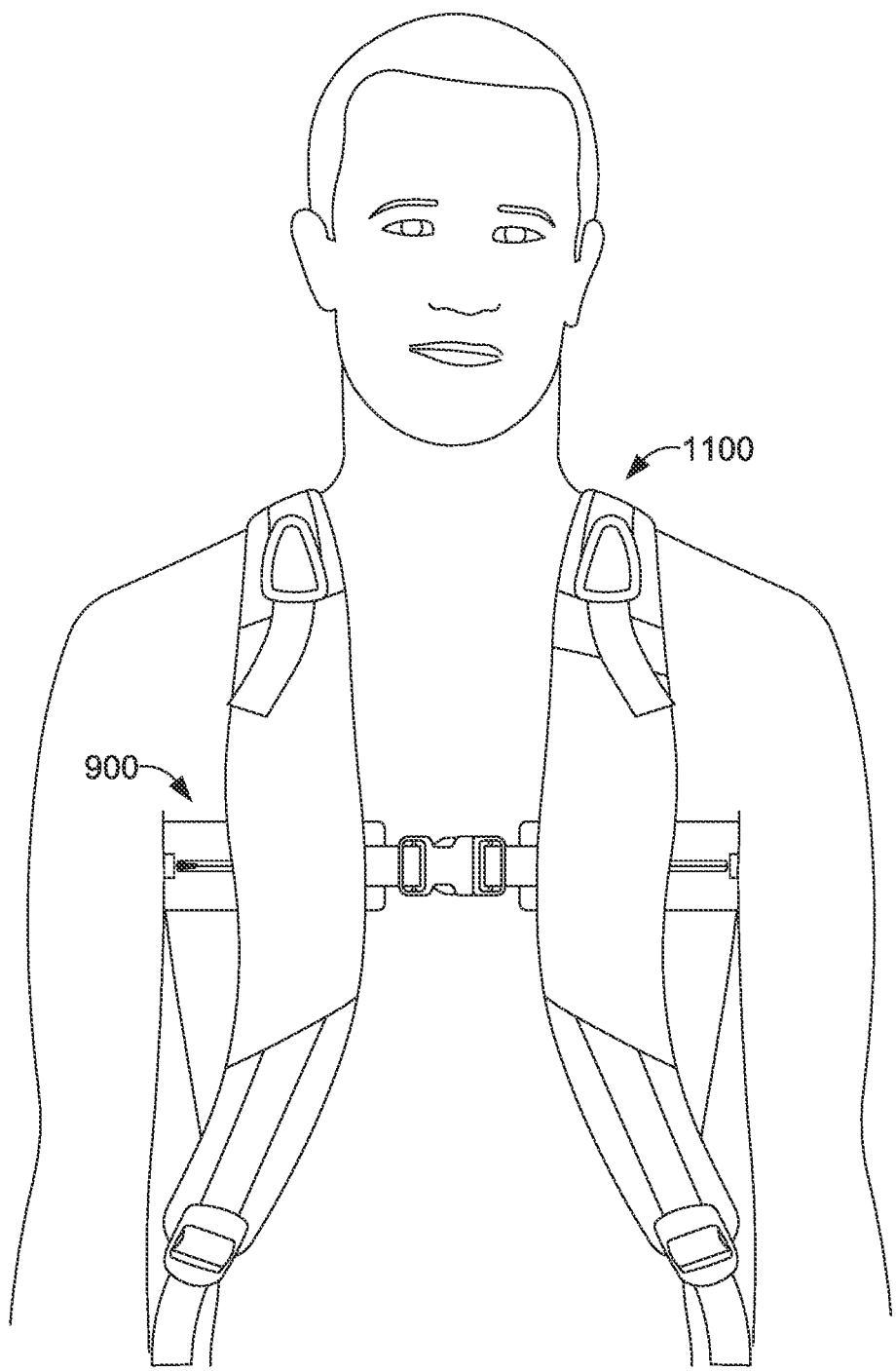
FIG. 31C is a front, perspective view of an exemplary apparatus unit coupled to an exemplary wearable pack, where the combination is being worn by a user, in accordance with an exemplary embodiment hereof.
Figure 32A:
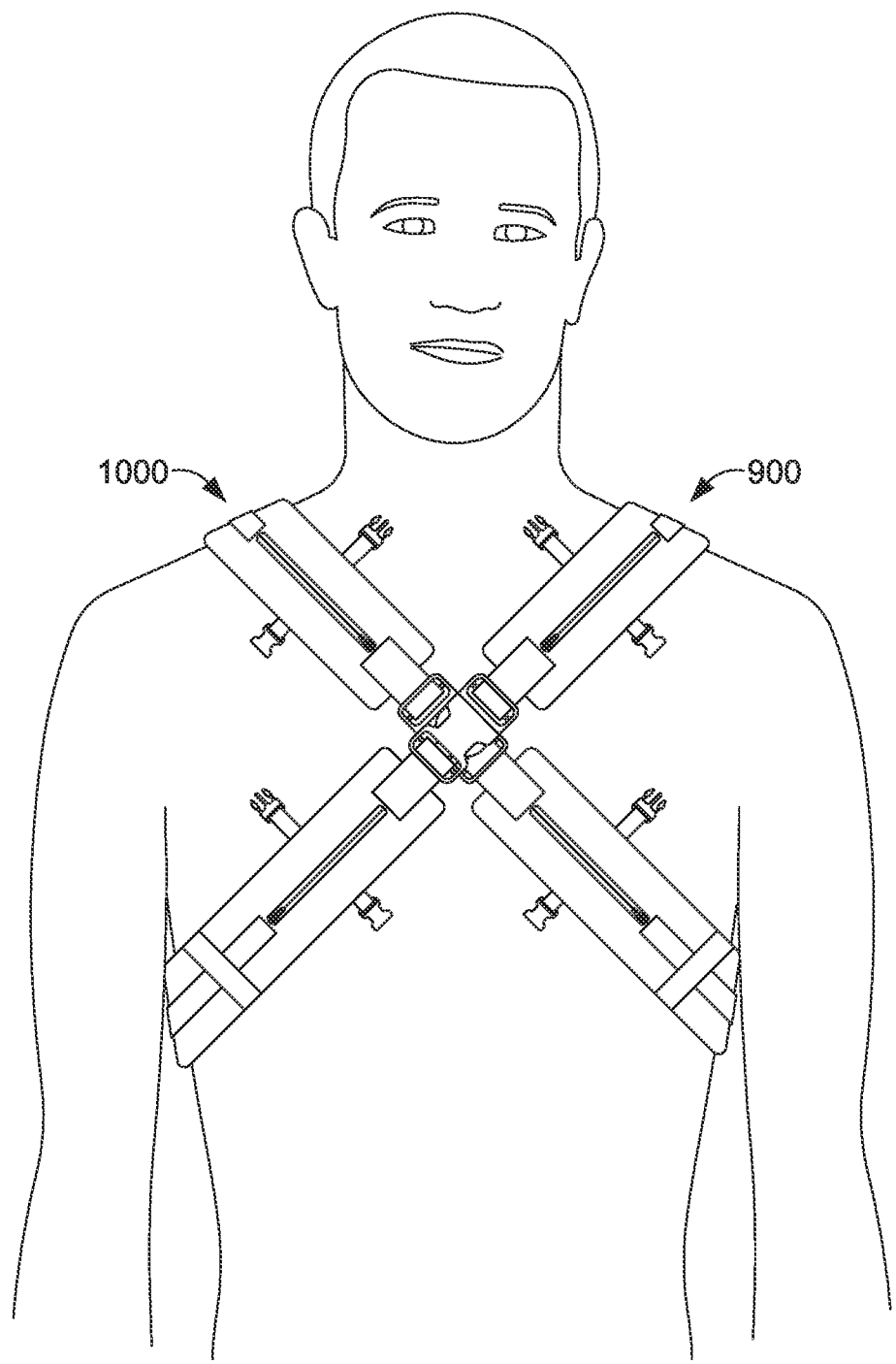
FIGS. 32A-B are front and rear, perspective views, respectively, of two exemplary apparatus units being worn in a crisscross configuration, in accordance with an exemplary embodiment hereof.
Figure 32B:
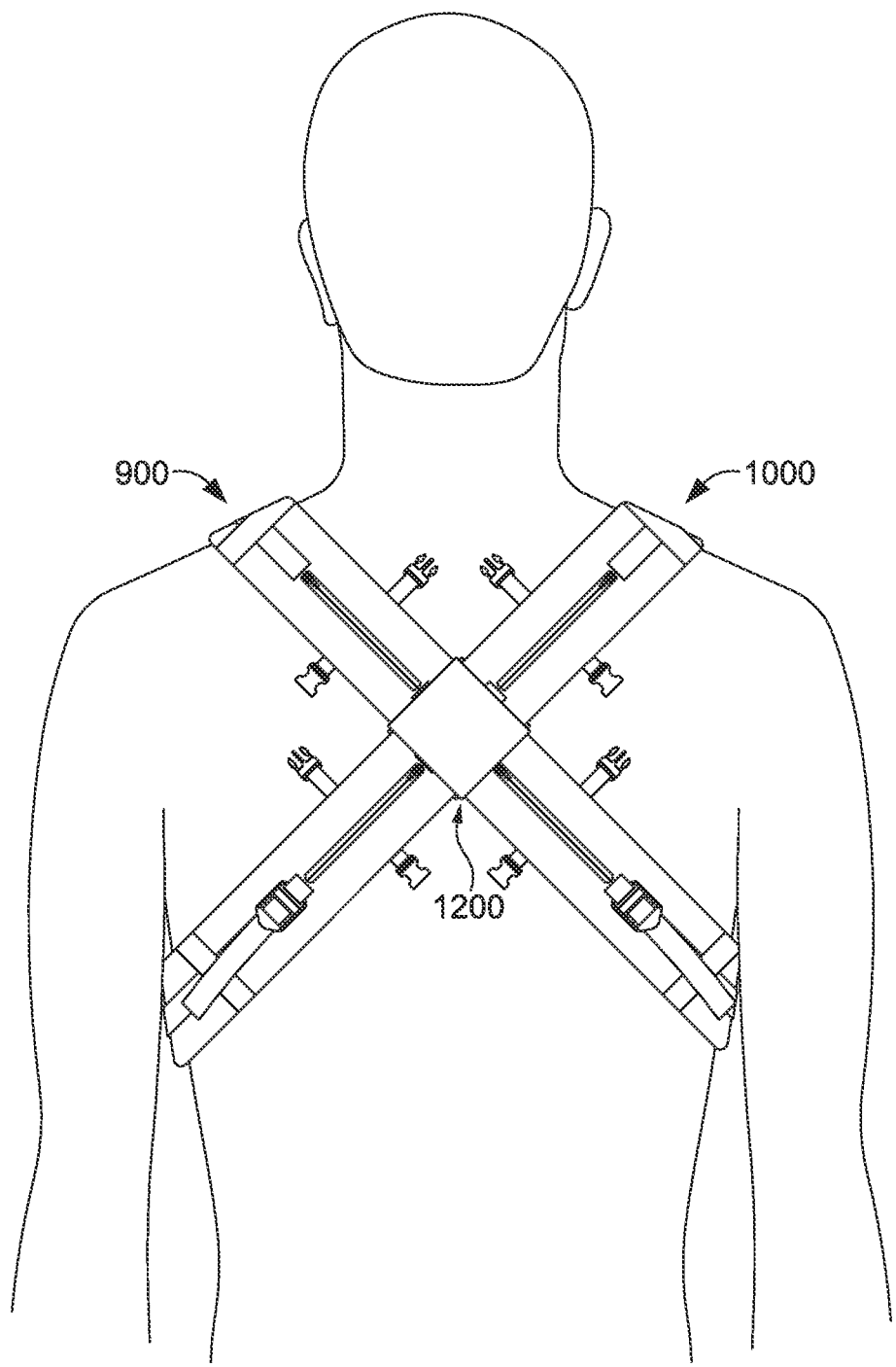
Figure 33A:
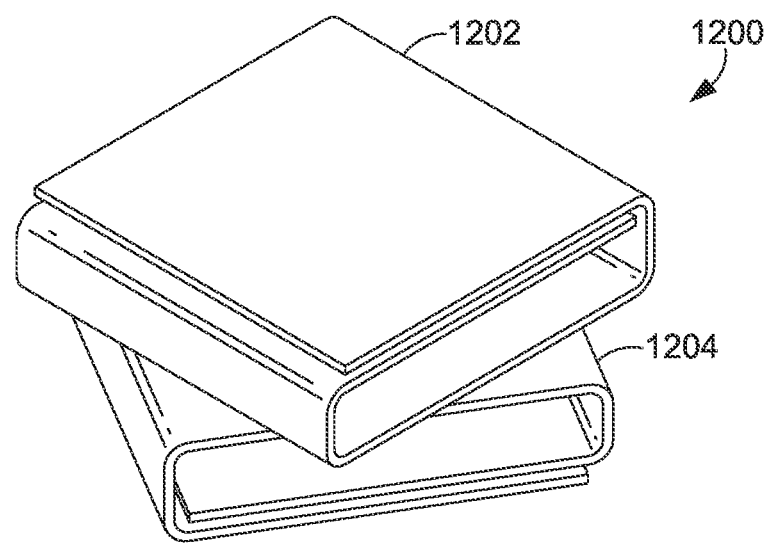
FIGS. 33A-B are perspective views of an exemplary positioning mechanism, in accordance with an exemplary embodiment hereof.
Figure 33B:
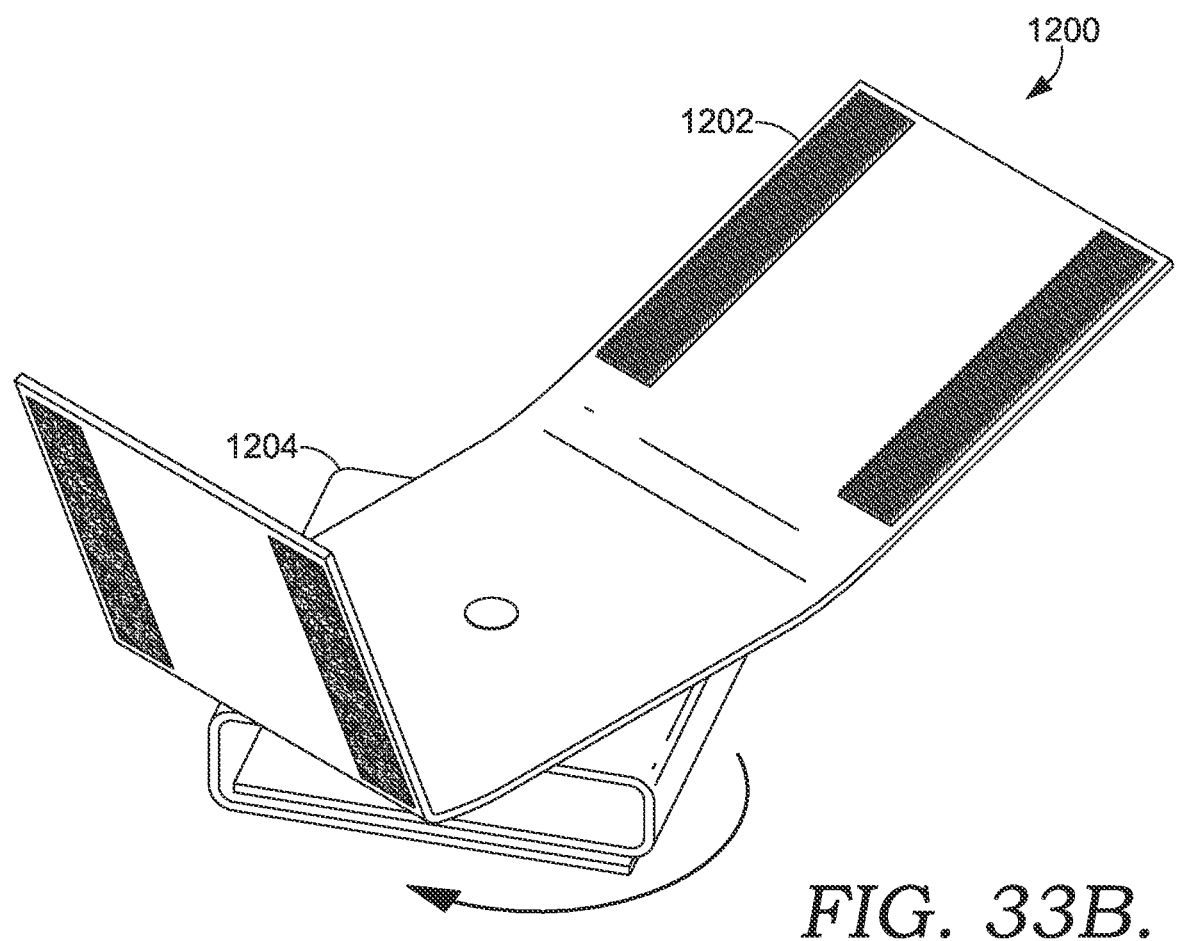
Figure 35C:
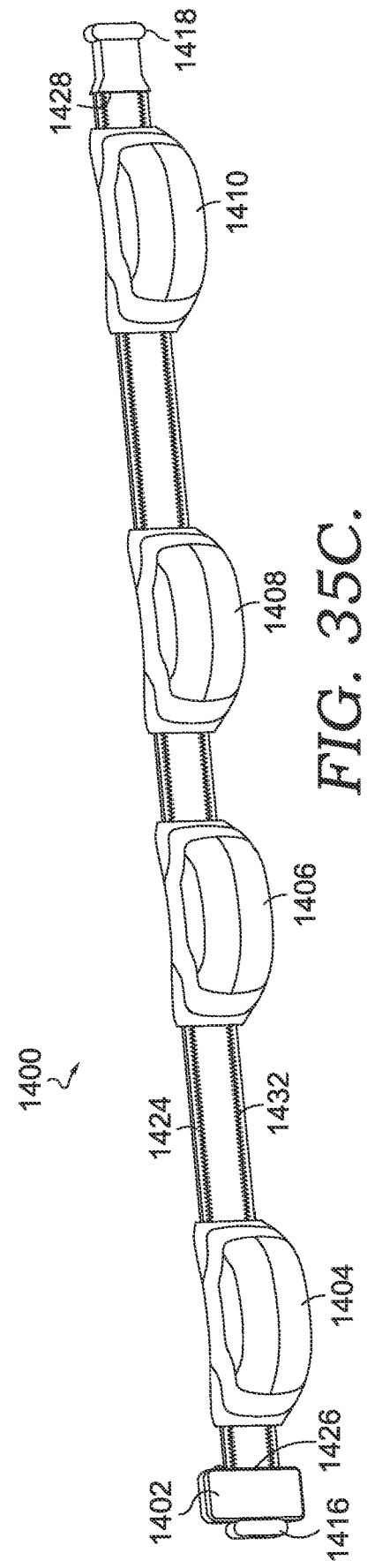
FIGS. 35C-D are front and rear, perspective views, respectively, of the exemplary vibration band of FIG. 35A, in accordance with an exemplary embodiment hereof.
Figure 35D:
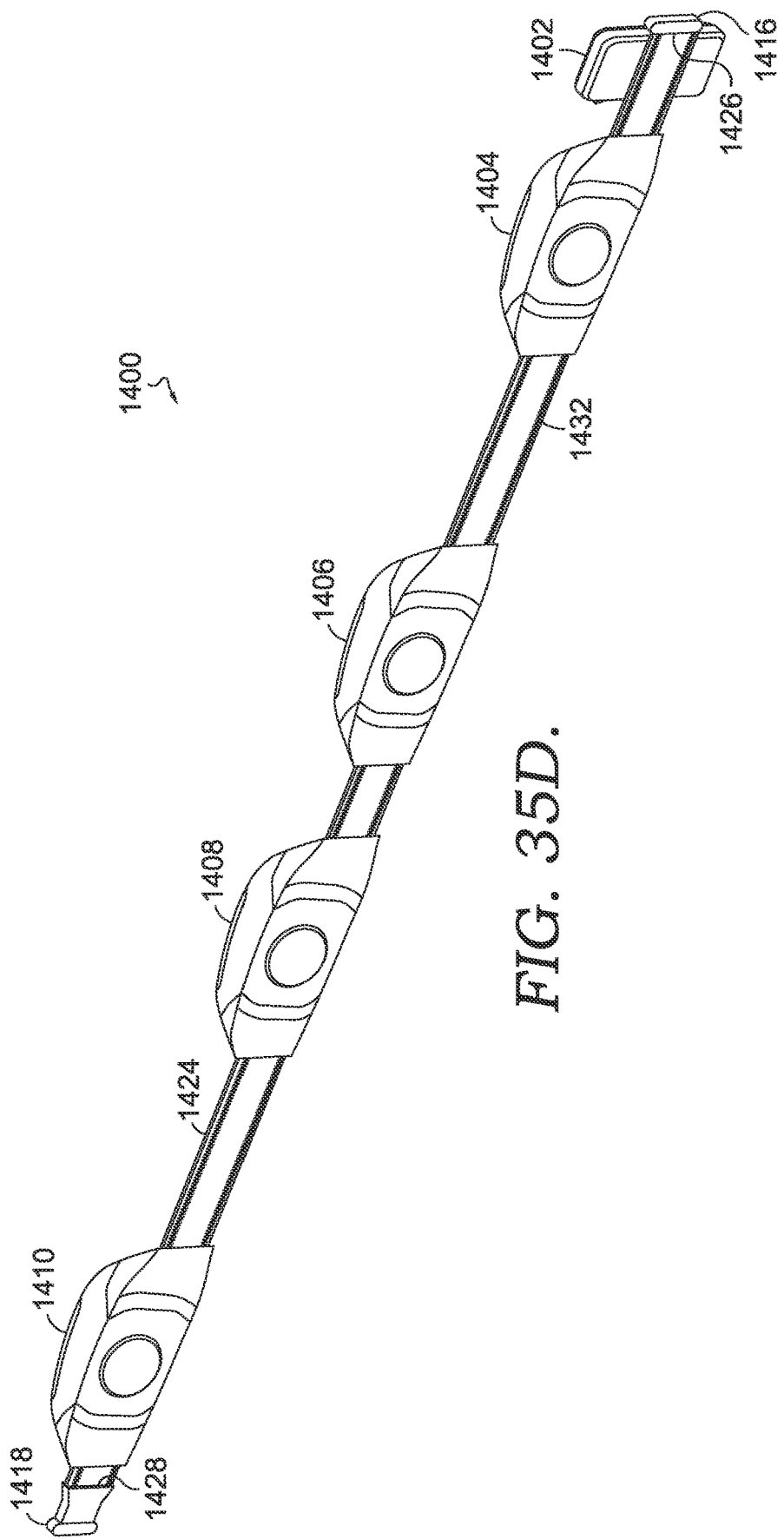

Turning now to the remaining figures, several different in-use configurations are shown. FIGS. 30A-B show the units 900 and 1000 secured around the torso of a user via releasable connection assemblies and shoulder straps. FIGS. 31A-C show a wearable pack 1100 that includes loops 1102, 1104, and 1106 for receiving the unit 900. The pack 1100 may maintain the unit 900 at a desired height on a user's body and prevent the unit 900 from slipping downward. In this way, the pack 1100 may serve a purpose that is similar to that served by the shoulder straps shown in FIGS. 30A-B. FIGS. 32A-B show a crisscross configuration of units 900 and 1000. The crisscross configuration may be facilitated by a positioning mechanism 1200 for positioning and maintaining multiple units in a crisscross configuration. For example, FIGS. 33A-B show a positioning mechanism 1200 that includes two separate sleeves 1202 and 1204 that are rotatably coupled to one another. A unit may be placed in each sleeve, and the sleeves may then be rotated until they are offset by a desired angle, such as an angle of approximately 90 degrees, as is shown in FIG. 32B. The sleeves may include hook-and-loop fasteners, or any other releasable connector, to facilitate placing a unit in the sleeve. An additional exemplary configuration of a positioning mechanism 1300 is shown in FIG. 34. The positioning mechanism 1300 may be a disc that includes channels for receiving a unit and routing the unit in a desired direction.

The controller and user input features previously discussed herein may be incorporated into the unit 900 (and any additional units used in conjunction with unit 900). For example, the unit 900 may be communicatively coupled to a mobile device application and/or a remote control. When multiple units are used in conjunction with one another, they may be controlled in a coordinated manner. For example, a mobile device application and/or remote may allow a user to select a number of units that are to be used, allow the user to pair each unit to the mobile device and/or remote, such as via a Bluetooth® connection, and enable the user to customize a percussive therapy session based on the user's particular needs. Additionally or alternatively, user input components may be provided on the units, themselves. The units may include a display screen that displays information regarding operational settings.

It will be understood by those having skill in the relevant art that the features described herein with respect to various exemplary embodiments may be combined and/or interchanged. For example, the features described with respect to the exemplary chest bands 100 or 600 may be combined and/or interchanged with the features described with respect to the exemplary vibration band 800 and/or unit 900. As one example, rather than mounting chest band segments 604, 606, 608, and 610 on the belt 602, these chest band segments may be coupled together in a linear chain via a series of connectors, as are chest band segments 102 and 104 in FIGS. 1-4, for example. As another example, chest band segments 102 and 104 may include connectors in order to facilitate the formation of parallel chains of chest band segments, as discussed with respect to other embodiments. Accordingly, the exemplary embodiments discussed with respect to the figures herein are not intended to be mutually exclusive, but instead set forth various features that may be combined and incorporated into an apparatus for providing percussive therapy.

As mentioned, the aspects discussed above are exemplary. Turning now to the remaining figures, additional aspects are discussed.

FIG. 35A-D illustrate an exemplary apparatus 1400 comprising a single vibration band for providing chest therapy. The apparatus 1400 includes an elongated band 1424; covers 1404, 1406, 1408, and 1410, each of which encloses one or more vibrating elements for providing percussive chest therapy; a controller enclosure 1402; and a releasable connection assembly including connector 1416 and connector 1418.

Exemplary features of various components of the apparatus 1400 will now be discussed, beginning with the elongated band 1424. In the exemplary configuration depicted, the band 1424 is elongated in shape. As used herein, the term "elongated" is used to describe an object that has a length exceeding its width. For example, the ratio of the length to width of the band 1424 may be between approximately 5:1 and 30:1. In other exemplary configurations, the band 1424 may have a different shape, such as a non-elongated shape. The band 1424 may be constructed of elastic materials, non-elastic materials, or a combination of elastic and non-elastic materials, including multiple layers of varying elasticity. An elastic material may facilitate a user coughing during a chest therapy session. The length of the band 1424 may be adjustable in order to provide a customized fit for a particular user.

The band 1424 has a first terminal end 1426 and a second terminal end 1428 opposite the first terminal end 1426. The band 1424 also has a top surface 1420 and a bottom surface 1422 opposite the top surface 1420. The top surface 1420 of the band 1424 faces away from a user's body when the user wears the apparatus 1400 (i.e. the portion that is visible to an observer). The bottom surface 1422 faces toward the user's body when the user wears the apparatus 1400. While not shown in FIGS. 35A-D, the band 1424 also includes at least one opening that extends through the top surface 1420 and the bottom surface 1422. This opening will be discussed in more detail with respect to FIG. 37B.

A plurality of covers 1404, 1406, 1408, and 1410 are coupled to the band 1424. FIGS. 36A-D depict exemplary features of cover 1404, which may also be features of covers 1406, 1408, and 1410. As shown in FIGS. 36A-D, cover 1404 encloses an internal cavity 1500 that is configured to receive one or more vibrating elements, such as vibrating element 1600, to provide percussive chest therapy to a user wearing the apparatus 1400. The configuration of the covers depicted in the figures is exemplary only, and the term "cover" is intended to include a wide variety of structures for covering, enclosing, and/or receiving a vibrating element. Other terms may be used to refer to the covers, such as pockets, housings, casings, enclosures, and others.

Each of covers 1404, 1406, 1408, and 1410 is disposed between the first terminal end 1426 and the second terminal end 1428 of the band 1424. The number and location of the covers 1404, 1406, 1408, and 1410 in the figures is exemplary only. There may be any number of covers, and they may be disposed at any number of locations along the length of the band 1424. In exemplary figures, the covers 1404, 1406, 1408, and 1410 are not equally distanced from one another. For example, the distance 1414 between covers 1406 and 1408 is less than the distance 1412 between covers 1404 and 1406. In some exemplary configurations, the covers 1404, 1406, 1408, and 1410 may be spaced equally apart on the band 1424, such that the distance between each adjacent pair of covers is the same. Any number of covers and any spacing between adjacent covers is included within the scope hereof.

The covers 1404, 1406, 1408, and 1410 (and the vibrating elements enclosed therein) may be removably and/or adjustably coupled to the band 1424. For example, they may be moveable (e.g., slidable) along a length of the band 1424 in order to provide a percussive force at a customized location on a user's body based on the unique needs of a particular user. The covers may be configured to slide or otherwise move within a predetermined distance along the length of the band 1424. For example, each of the covers (and the one or more vibrating elements enclosed therein) may be configured to move several inches, or more, along the length of the band. An exemplary means for enabling this adjustability will be discussed in more detail with respect to FIGS. 37A-D.

The apparatus 1400 also includes a plurality of wire tunnels, such as wire tunnel 1430. The dashed lines indicate that in this example, the wire tunnels comprise a layer within the band 1424, between the top surface 1420 and the bottom surface 1422. The wire tunnels provide a secure passageway for one or more wires along the band 1424 and ensure that the wires do not become entangled when the covers are moved or the apparatus 1400 is in use. The wires within the wire tunnels extend between the controller enclosure 1402, which may include a controller and/or a power source, and the vibrating elements within the covers, thereby powering and/or controlling the vibrating elements, which then provide percussive or vibrational forces for therapeutic use. Discrete wire tunnels may be disposed between the controller enclosure 1402 and cover 1404, between covers 1404 and 1406, between covers 1406 and 1408, and between covers 1408 and 1410. Additionally or alternatively, one or more wire tunnels may span longer sections of the band 1424, and may even run continuously along the length of the entire band.

In the exemplary figures, the wire tunnels comprise an inner layer of the band 1424, but it will be understood that other configurations are included within the scope hereof. For example, the wire tunnels could be coupled to the top surface 1420 or to the bottom surface 1422 of the band 1424, or if the band includes multiple layers of material, the wire tunnels could be sandwiched between any such layers. Additional aspects of the wire tunnels will be discussed with respect to FIGS. 38-39.

As mentioned, the apparatus 1400 also includes a controller enclosure 1402, which houses a controller (for controlling the vibrating elements within covers 1404, 1406, 1408, and 1410) and/or a power source, such as a rechargeable battery. In the exemplary embodiment depicted, the controller enclosure 1402 is coupled directly to a releasable connection assembly (discussed below). Other placements are included within the scope hereof. For example, the controller enclosure 1402 may be incorporated into, or integral with, the connection assembly. The controller within the controller enclosure 1402 receives user input to control the action of the vibrating elements to provide the desired chest therapy. It will be understood that the previous discussion of controller features is also applicable to the controller within controller enclosure 1402. Additional details regarding the controller and the elements housed therein are discussed with respect to FIG. 40.

The apparatus 1400 includes a releasable connection assembly for securing the apparatus 1400 around the body of a user to form a circumferential band. The illustrated connection assembly includes connectors 1416 and 1418, which are coupled to opposite terminal ends of the band 1424. For example, connectors 1416 and 1418 may be releasably coupled to one another in order to form a circumferential chest band around the user, a diagonal configuration over a shoulder and around the torso of the user (to form a crisscross configuration when paired with a second vibration band), or any number of other configurations. As used herein, the term "releasably connectable" refers to components that are intended to be connected and disconnected repeatedly without degrading the structural integrity of the components. Exemplary releasable connection assemblies include snap-fit buckles, clasps, belts, hook-and-loop fasteners, ties, laces, zippers, G-hooks, other hooks, and any other means of releasably connecting terminal ends 1426 and 1428 to one another. In additional aspects, a non-releasable connection between terminal ends 1426 and 1428 may be provided. As used herein, the term "non-releasably connectable" refers to components that cannot be connected and disconnected repeatedly without degrading the structural integrity of the components. For example, the terminal ends 1426 and 1428 may be glued or stitched together such that the band 1424 is permanently or semi-permanently configured as a circumferential band.

The connector 1416 may be a stationary connector coupled to the first terminal end 1426 of the band 1424, and the connector 1418 may be an adjustable connector 1418 coupled to the second terminal end 1428 of the band 1424. The adjustable connector 1418 may facilitate adjusting a length of the band 1424 (i.e. adjusting a distance between the first terminal end 1426 and the second terminal end 1428) and provide a customized fit for a particular user. For example, a user with a relatively small torso may shorten the length of the apparatus 1400, such that when the apparatus 1400 is planar (i.e. is lying flat), the distance between the first terminal end 1426 and the second terminal end 1428 is reduced.

The apparatus 1400 also includes stitching 1434 on the band 1424 and/or the covers 1404, 1406, 1408, and 1410. This stitching may aid in "gripping" the apparatus 1400 to a user's body and preventing it from slipping when in use. Material selection may also facilitate such gripping.

While FIGS. 35A-D show one vibration band (as noted previously, the term "vibration band" refers to the combination of a band and one or more vibrating elements) as a part of the apparatus 1400, it is contemplated that two or more vibration bands having similar configurations may be utilized, as shown in FIGS. 41A-B and 42A-B and as will be discussed in more detail with respect to those figures. In this instance, the vibration bands may be releasably connected to one another or positioned securely on the user's torso in a variety of different configurations (e.g., positioned in parallel; crisscrossed forming an "X" shape, similar to FIGS. 32A-B). Utilizing multiple vibration bands facilitates the application of a percussive force across a larger area of the user's body. Accordingly, the apparatus can be customized based on user size and/or body shape (e.g., an adult may use two or more vibration bands, while a child may use only one), severity of medical condition (e.g., a person having a very severe medical condition may use more vibration bands than a person having a less severe condition uses), and other considerations.

Turning to FIGS. 36A-D, exemplary features of the covers 1404, 1406, 1408, and 1410 will now be discussed, using cover 1404 as an example. Although the following discussion references cover 1404, it will be understood that other covers may have the same or similar features.

Figure 36A:
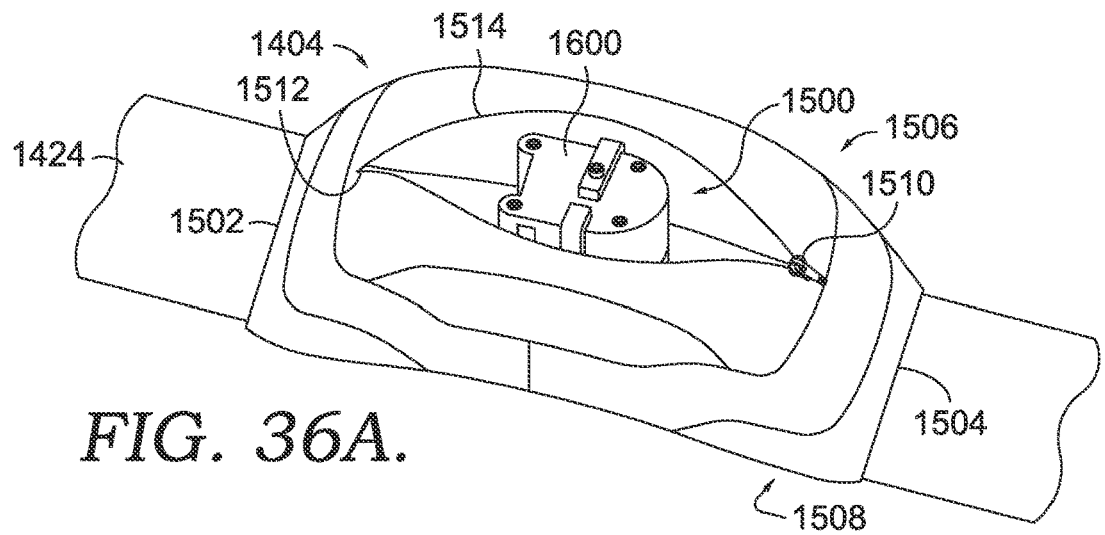
FIG. 36A is top, perspective view of an exemplary cover in an open position and having a vibrating element disposed therein, in accordance with an exemplary embodiment hereof.
Figure 36B:
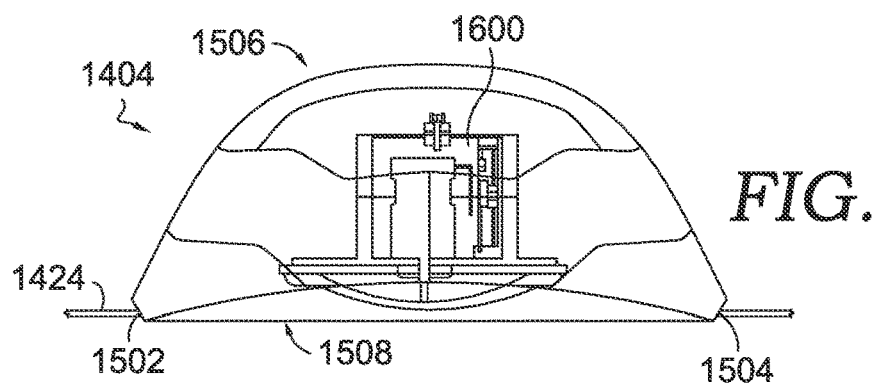
FIG. 36B is a side view of the cover of FIG. 36A, in accordance with an exemplary embodiment hereof.
Figure 36C:
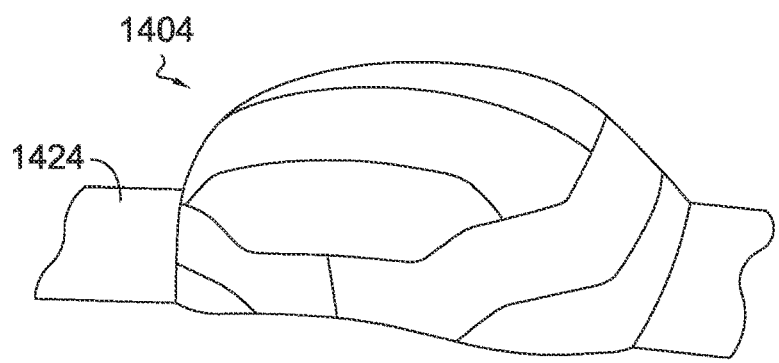
FIG. 36C is a top, perspective view of the cover of FIG. 36A in a closed position, in accordance with an exemplary embodiment hereof.

FIGS. 36A and 36C illustrate top perspective views of cover 1404 in an open position and a closed position, respectively. Cover 1404 has a first terminal end 1502, a second terminal end 1504, a top surface 1506 (which faces away from the user's body when in use), a bottom surface 1508 (which faces the user's body when in use), and a closeable opening 1514 that provides access to an internal cavity 1500, which is configured to receive the vibrating element 1600. Although a single vibrating element is pictured, it will be understood that any number of vibrating elements may be disposed within the internal cavity 1500. Access to the internal cavity 1500 may be desirable for performing maintenance on the vibrating element 1600 (e.g., repairing the vibrating element 1600, removing the vibrating element 1600 and replacing it with a new one) or other components contained within the internal cavity. Such access may also facilitate adjusting the position of the covers and the vibrating elements housed therein, as will be discussed in more detail below.

An opening and closing mechanism facilitates the transition between the open position seen in FIG. 36A and the closed position seen in FIG. 36C. In the figures, the opening and closing mechanism is depicted as a zipper 1510, but many other mechanisms are included within the scope hereof. For example, buckles, clasps, belts, hook-and-loop fasteners, ties, and laces may be used as the opening and closing mechanism. When in the closed position, the zipper may be tucked under one end of the closeable opening 1514, such as end 1512, so that the opening 1514 will be secured closed. In some configurations, it is contemplated that in order to open the zipper 1510 to grant access to the internal cavity 1500, a small tool will be used to "grab" the zipper 1510 to open it. This may prevent users from opening the zipper 1510 and may thus limit access to only authorized users (e.g., service technicians).

Figure 36D:
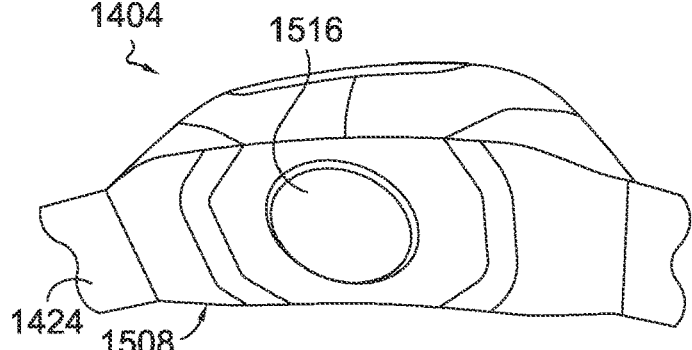
FIG. 36D is a bottom, perspective view of the cover of FIG. 36A, in accordance with an exemplary embodiment hereof.

FIG. 36B provides a transparent side view of the cover 1404 and shows the positioning of the vibrating element 1600 within the cover 1404, and FIG. 36D illustrates a bottom perspective view of the cover 1404. When power is provided to the vibrating element 1600, it creates percussive or vibrational forces that travel through the bottom surface 1508 of the cover 1404 and thereby provides percussive therapy to a user at the location of the cover 1404 and the vibrating element 1600 contained therein. As shown in FIG. 36D, the bottom surface 1508 includes an impact area 1516 corresponding to the area that the vibrating element 1600 strikes. The material composition of impact area 1516 may be different from other portions of the cover 1404. For example, the material may be selected to enhance a user's comfort during a therapy session. It may include a layer of padding to prevent the hard portions of the vibrating element 1600 from causing discomfort while still allowing the percussive force to reach the user's body. Accordingly, the material for the padding may be selected so that the vibrational force provided by the vibrational elements is not overly dampened. This may include foam (e.g., closed cell foam), neoprene, rubber, or another material. Additionally or alternatively, a layer of padding may be disposed adjacent to the entire bottom surface 1508, and the impact area 1516 may have the same or different padding as the remainder of the bottom surface 1508. Impact area 1516 is depicted as circular, but it will be understood that any shape or configuration of this area is included within the scope hereof.

Additionally, the cavity 1500 of cover 1404 may be filled with material around the vibrating element 1600, such as padding or foam (not shown), to protect the vibrating element from external forces, provide stability during use (e.g., maintain the vibrating element in a substantially vertical position and/or disposed within the central region of the cover 1404), provide comfort for the user when the apparatus 1400 is worn, and dampen sound from the motor to provide quieter operation. For example, the padding may prevent the hard housing of the vibrating elements from causing discomfort, while still allowing the percussive force to reach the user's body. Accordingly, the material for the padding may be selected so that the vibrational force provided by the vibrational elements is not overly dampened. The padding layer may include foam, such as closed cell foam, or another material. The padding layer may be customized to fit the vibrating element 1600 and any associated driver, electronics, or other component in the cavity 1500. In other words, the padding may completely fill the void around such components.

The cover 1404 includes various stitch lines. The depicted design of these lines is exemplary only and other design configurations may be utilized for functional and/or decorative reasons. As mentioned, certain stitching on the covers and/or other portions of the apparatus 1400, including the band 1424, may aid in "gripping" the apparatus 1400 to a user's body and preventing the apparatus 1400 from slipping when in use. Material selection may also facilitate such gripping.

Although details of the wiring and other electrical connections are not depicted for ease of viewing, it will be understood that the cover 1404 may contain wires for connecting the vibrating element 1600 to a power source and/or controller. Exemplary configurations will be discussed with respect to FIGS. 38-39. In additional exemplary configurations, the power source (e.g., battery) for the vibrating element 1600 and/or the controller for controlling the vibrating element 1600 may be contained within the cover 1404. The configuration of the vibrating element 1600 depicted in the figures is exemplary only, and it will be understood that the vibrating element 1600 may include different and/or additional features, including those discussed herein with respect to other vibrating element configurations.

The cover 1404 may be comprised of any type and/or number of materials. In embodiments, the cover 1404 is a durable textile that is semi-flexible. Any combination of rigid, semi-rigid, and flexible materials may be used to form the cover 1404.

The cover 1404 may be coupled to the band 1424 in any number of ways. The cover 1404 may be detachably or permanently affixed to the band 1424. For example, the cover 1404 may have openings through which the band 1424 extends. Such openings may be at the first terminal end 1502 and at the second terminal end 1504 of the cover 1404. Additionally or alternatively, the cover 1404 may be affixed to the band 1424 via hook-and-loop fasteners, loops, buckles, sewing, glue, or any other means. The cover 1404 may be removable, such that a user can customize the number of covers on a vibration band. Additionally or alternatively, the location of the cover 1404 along the length of the band 1424 may be adjusted, as discussed in more detail below.

Figure 37A:
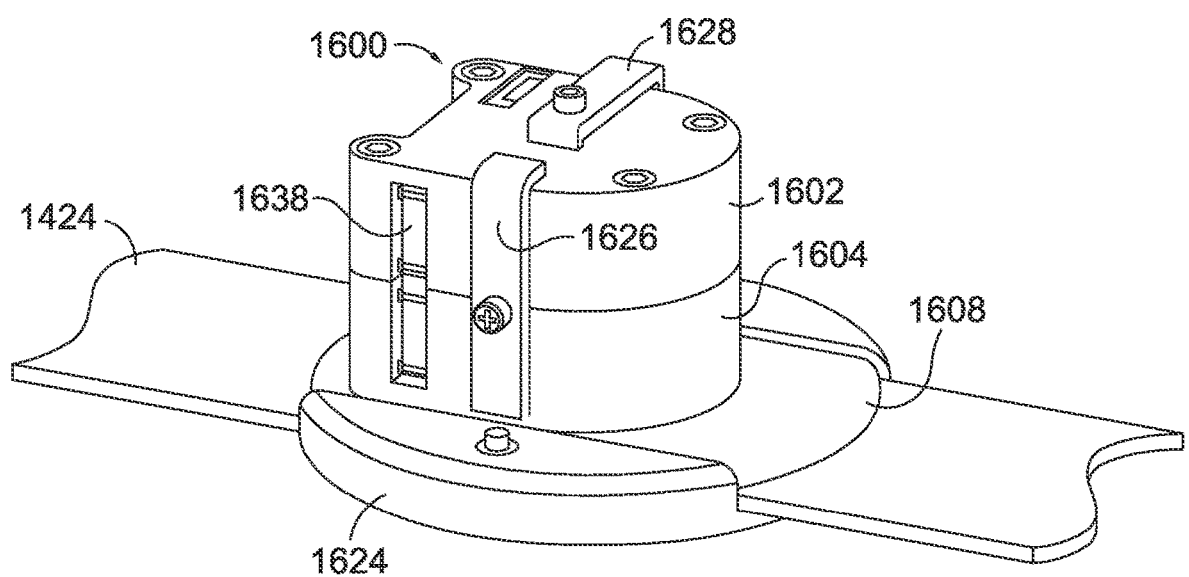
FIG. 37A is a side, perspective view of a vibrating element coupled to a band, in accordance with an exemplary embodiment hereof.
Figure 37B:
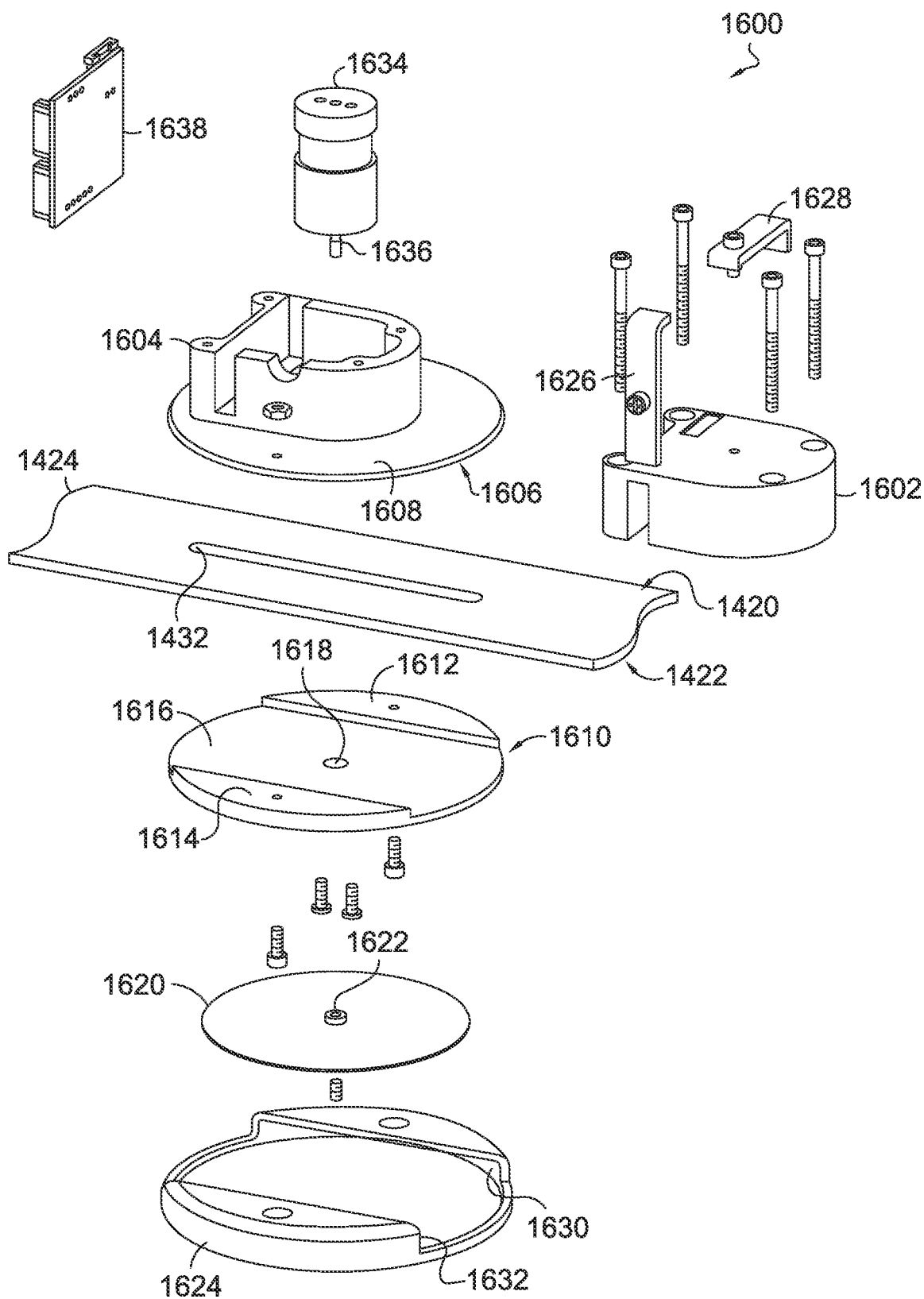
FIG. 37B is an exploded view of the vibrating element and band of FIG. 37A, in accordance with an exemplary embodiment hereof.
Figure 37C:
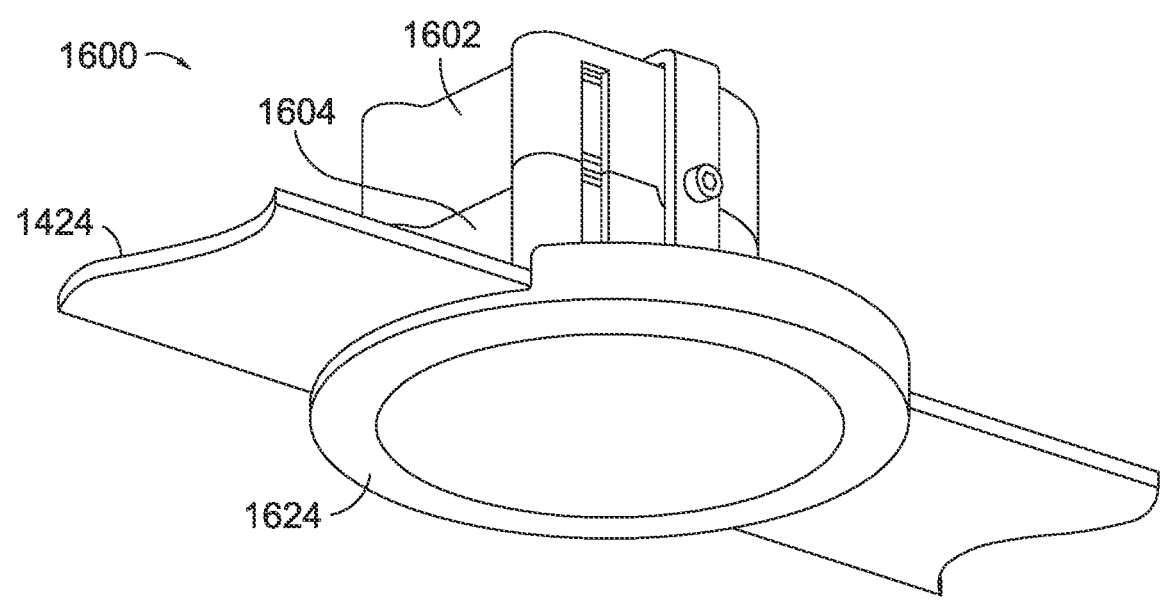
FIG. 37C is a bottom, perspective view of the vibrating element and band of FIG. 37A, in accordance with an exemplary embodiment hereof.
Figure 37D:
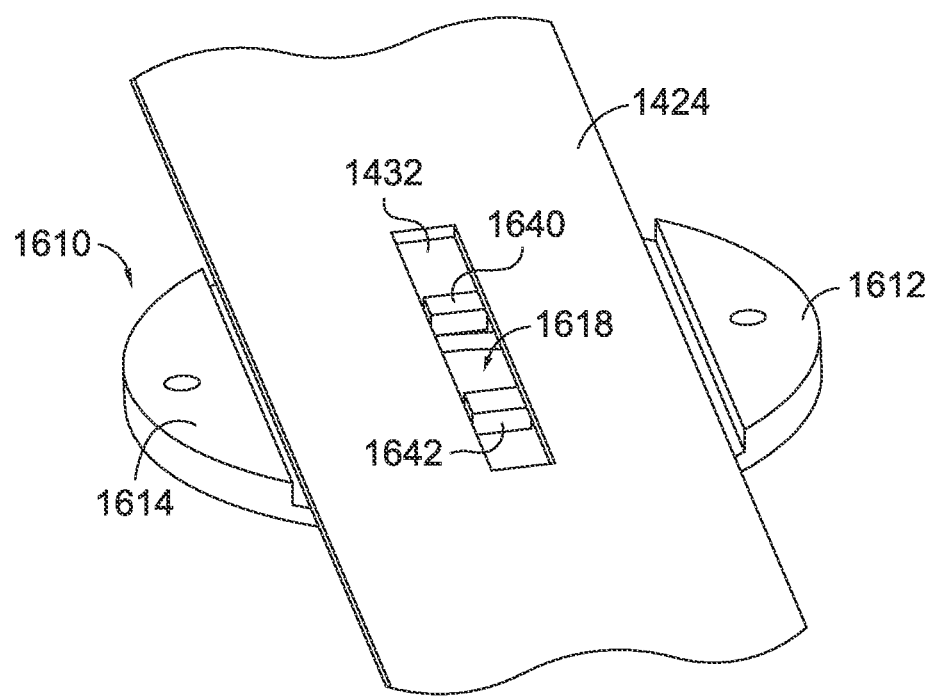
FIG. 37D is a top perspective view of the band slidably coupled to a component of the vibrating element of FIG. 37A, in accordance with an exemplary embodiment hereof.

Exemplary details regarding the vibrating elements and the manner in which they may be coupled to the band 1424 will now be discussed with respect to FIGS. 37A-D, which illustrate aspects of vibrating element 1600. Vibrating element 1600 is representative of the one or more vibrating elements that may be disposed within each of the covers of the apparatus 1400. FIGS. 37A and 37C provide perspective views of the vibrating element 1600, and FIG. 37B provides an exploded view. FIG. 37D provides a perspective view of a mounting plate 1610 included in the vibrating element 1600 and adjacent to the band 1424.

As previously discussed with respect to various configurations, vibrating element 1600 provides percussive or vibrational forces to a user's body when in use. This may be accomplished in any number of ways. Exemplary mechanisms for generating a percussive force include unbalanced motors, eccentric rotating mass vibration motors, linear motors, voice coil motors, and any other motor or assembly that generates a percussive or vibrational force. For example, the vibrating element 1600 includes a motor 1634 coupled to a shaft 1636 (also referred to as a "rod" or "plunger"), which is coupled to a mass 1620. When powered, the motor 1634 causes the mass to linearly reciprocate (e.g., as in a voice coil motor). Thus, when the vibrating element is positioned adjacent to the torso of a user, as when a vibration band is in use, a tapping force is provided to the user's torso.

At a high level, vibrating element 1600 has an upper housing portion 1602 and a lower housing portion 1604 that, together, house the motor 1634. The lower housing portion 1604 is disposed adjacent to the top surface 1420 of the band 1424. On the opposite side of the band 1424, a mounting plate 1610 is disposed adjacent to the bottom surface 1422 of the band 1424. The mounting plate 1610 includes a channel 1616 for receiving the band 1424 and allowing the band 1424 to slide within the channel. The shaft 1636 of the motor 1634 extends through an opening in the lower housing portion 1604, through an opening 1432 in the band 1424, through an opening 1618 in the mounting plate 1610, and is then coupled to the mass 1620. A boot 1624 fits over the mass 1620, mounting plate 1610, and lower housing portion 1604. (A cross-section view of this assembly is provided in FIG. 38A.) Each of these aspects will now be discussed in more detail. Various elements discussed herein may be additively manufactured to be lightweight and thus reduce the overall weight of the apparatus 1400.

The upper housing portion 1602 and lower housing portion 1604 may include tongues and grooves or other complimentary and/or interlocking components that facilitate securing the housing portions in place with respect to one another. In the figures, removable fasteners (e.g., bolts or screws) may be inserted into aligned openings on both the upper housing portion 1602 and the lower housing portion 1604 to secure them together. Additionally, the side bar 1626 and the top bar 1628 may be secured to the upper housing portion 1602 and the lower housing portion 1604 via removable fasteners. The upper housing portion 1602 and lower housing portion 1604, as well as other components, may be honeycombed in order to reduce the weight of the vibrating element 1600 and thus the overall weight of the apparatus 1400.

The bottom surface 1606 of the base 1608 of the lower housing portion 1604 is disposed adjacent to the top surface 1420 of the band 1424. The mounting plate 1610 is disposed adjacent to the bottom surface 1422 of the band 1424, with the band 1424 disposed in the channel 1616 of the mounting plate 1610, flanked by protrusions 1612 and 1614 on either side. The mounting plate 1610 is coupled to the base 1608 of the lower housing portion 1604. For example, openings in the protrusions 1612 and 1614 of the mounting plate 1610 may be aligned with openings in the base 1608, and removable fasteners may be used to secure the mounting plate 1610 to the lower housing portion 1604. This configuration allows the vibrating element 1600 to slide along the band 1424. The depth of the channel 1616 (as may be defined by the height of the protrusions 1612 and 1614), as compared to a thickness of the band 1424, may be chosen to provide a desired level of resistance against sliding. For example, a channel depth significantly greater than the band thickness would enable the band 1424 to move easily within the channel 1616. A channel depth less than the band thickness would pinch the band 1424 and resist its movement. In embodiments, the channel depth is 5-75% greater than the band thickness. Similarly, the width of the channel 1616 (as may be defined by the distance between the protrusions 1612 and 1614), as compared to a width of the band 1424, may be chosen to facilitate the band 1424 sliding within the channel 1616. In embodiments, the channel is 5-75% greater than the band width. The relative dimensions of the band 1424 and the channel 1616 are illustrated in FIG. 37D. It will be understood that the configuration of the mounting plate 1610 is exemplary only. It embodiments, it may comprise different sizes and/or shapes, or may be omitted from the vibrating element 1600, altogether.

As previously noted, when the motor 1634 is disposed within the housing portions, a shaft 1636 coupled to the motor 1634 extends through an opening in the lower housing portion 1604, through an opening 1432 in the band 1424, through an opening 1618 in the mounting plate 1610, where it is then coupled to the mass 1620. The shaft 1636 may be coupled to the mass 1620 via a removable fastener (e.g., a set screw) and the opening 1622 in the mass 1620, or in any other manner. A cross-section view of this assembly is provided in FIG. 38A. When power is provided to the motor 1634, the shaft 1636 acts similar to a plunger, reciprocating back and forth, tapping the mass against the user's body and thereby providing percussive therapy to the area of the user over which the vibrating element 1600 is disposed.

Exemplary aspects that facilitate adjustability and/or movability of the vibrating element 1600 will now be described. As previously mentioned, the vibrating element 1600 may move along the length of the band 1424 to provide better adaptability and customization for the individual (the previously described covers may move in conjunction with their respective vibrating elements, as will be further discussed with respect to FIG. 38A). This is facilitated by the shaft 1636 of the motor 1634 moving along the length of the opening 1432 and the band 1424 sliding within the channel 1616 of the mounting plate 1610. In this configuration, the degree to which the location of the vibrating element 1600 on the band 1424 may be adjusted is defined by the length of the opening 1432. At either end of the opening 1432, the shaft 1636 of the motor 1634 runs into the end of the opening 1432 and is prevented from moving any further. In embodiments, the length of the opening 1432 is one to two inches. In embodiments, the opening is longer, such as up to six inches. It will be understood that any length of opening is included within the scope hereof. In embodiments, the ratio of the length of the opening 1432 to the width or diameter of the shaft 1636 is at least 5:1, and the ratio of the width of the opening 1432 to the width or diameter of the shaft 1636 is between 1:1 and 2:1. In FIG. 37B, the opening 1432 is shown as a narrow oblong opening. However, it is contemplated that the opening 1432 on the band 1424 may be any shape or size that allows for movement of the vibrating element 1600. Additionally or alternatively, the opening 1432 may approximate the width or diameter of the shaft 1636, such that the vibrating element 1600 is fixed within the opening 1432. Any combination of stationary and moveable vibrating elements may be incorporated into a vibration band. In all embodiments, additional means of adjusting and/or customizing the vibration band may be provided, including other mechanisms described herein.

The boot 1624 may be secured around the mass 1620, the mounting plate 1610, and the base 1608 of the lower housing portion 1604. Specifically, cavities 1630 and 1632 may be configured to receive the outer edges of the mounting plate 1610 and the base 1608 of the lower housing portion 1604 (e.g., the portions corresponding to the protrusions 1612 and 1614). The channel running down the center of the boot 1624 may avoid interference with the movement of the band 1424. The boot may be secured in position, such as via removable fasteners or other means. The boot may be comprised of any number of materials. For example, silicon may be used. Different and/or additional materials may be selected based on the ease with which they can be positioned around the mounting plate 1610 and the base 1608 of the lower housing portion 1604 and/or the comfort they provide to a user during a therapy session.

FIG. 37D illustrates a perspective view of the band 1424 slidably coupled to the mounting plate 1610. As shown, mounting plate 1610 may include protrusions 1640 and 1642 on opposite sides of the opening 1618. When vibrating element 1600 is assembled, these protrusions 1640 and 1642 flank the shaft 1636 and protect the shaft from directly contacting the band at either end of the opening 1432. In other words, as the shaft 1636 moves within the opening 1432 (as may occur when the cover 1404 and the vibrating element 1600 housed therein slide along the length of the band 1424), when the shaft 1636 nears either end of the opening 1432, the protrusion 1640 or 1642 will contact the end of the opening 1432, rather than the shaft 1636 directly contacting the end of the opening 1432. This may protect the shaft 1636 from wear and tear during adjustments. This may also protect the shaft 1636 from wear and tear during use.

For example, without the protrusions 1640 and 1642, when the cover 1404 is adjusted to the far end of the opening 1432, the shaft 1636 may rub against the band 1424 as it reciprocates, spins, or otherwise moves. The protrusions 1640 and 1642 may protect against such contact. It will be understood that the configuration of the protrusions 1640 and 1642 is exemplary only and that other configurations are included within the scope hereof. For example, protrusions may surround additional sides, or even the entire circumference of the opening 1618 to protect the shaft 1636 from contacting the band 1424 in other areas.

Although wires and other power connections are not depicted for ease of viewing in FIGS. 37A-D, it will be understood that the vibrating element 1600 may include wires for connecting the motor 1634 to a power source. Such wires may extend through one or more apertures in the housing for the vibrating element, such as one or more apertures in the upper housing portion 1602 or lower housing portion 1604. For example, electrical component 1638 (shown as a printed circuit board) may include ports for electrically coupling the vibrating element 1600 to a power source. In embodiments, each vibrating element may be powered by a battery or other means, which may be located in the controller enclosure 1402 and/or within one or more covers. The configuration of the vibrating element 1600 depicted in the figures is exemplary only, and it will be understood that the vibrating element 1600 may include different and/or additional features, such as those discussed herein with respect to other vibrating element configurations. It will also be understood that the components and assembly of vibrating element 1600 are exemplary only. The vibrating element 1600 may include fewer, additional, and/or different components than those discussed above. Additionally, other means of coupling a vibrating element discussed with respect to other figures herein may also apply to vibrating element 1600 and band 1424.

Turning now to FIGS. 38A-B, FIG. 38A illustrates a cross-section of a portion of the apparatus 1400, and FIG. 38B illustrates a perspective view of the wire tunnel 1430 coupled to the band 1424 (without the cover 1404). As shown in FIG. 38A, the apparatus 1400 includes the band 1424, the cover 1404 that encloses the vibrating element 1600, the wire tunnel 1430, and hook-and-loop fasteners 1518 and 1520. The wire tunnel 1430 is coupled to the top surface 1420 of the band 1424. This may be done via hook-and-loop fasteners, loops, buckles, sewing, glue, or any other means. Within the wire tunnel 1430 are one or more wires 1702 that are connected to the vibrating element 1600 within cover 1404. The wire tunnel 1430 extends into the cover 1404, and inside the cover 1404, the tunnel 1430 terminates and the wires 1702 emerge from an opening 1708 in the tunnel 1430 and are connected with the vibrating element 1600 via a connector 1706. In embodiments, the connector 1706 may couple with a port on electrical component 1638. In this example, the wire tunnel 1430 provides an extra layer of material on top of the band 1424. Depending on the materials selected, this may increase the rigidity of the apparatus 1400, while still allowing enough flexibility to conform to a wide variety of body types and enough elasticity to permit coughing during treatment. In embodiments, the extra layer provided by the wire tunnel 1430 may terminate before the opening 1432 in the band 1424 (as shown in FIG. 38B), which facilitates movement of the vibrating element 1600 along the opening 1432.

The cover 1404 includes hook-and-loop fasteners 1518 and 1520. These may be releasably coupled to the band 1424, either directly or indirectly. For example, one portion of a hook-and-loop fastener may be permanently attached to the cover 1404, and the complimentary portion may be permanently attached to the band 1424. The complimentary portion may cover a portion of the band corresponding to an area over which the cover 1404 may move, or it may cover a larger portion of the band. In the figure, the hook-and-loop fasteners are coupled to the wire tunnel, which is coupled to the top surface 1420 of the band 1424. If a user desires to move the cover 1404 (and the vibrating element 1600 contained therein), the user may release the hook-and-loop fasteners 1518 and 1520 and slide the cover along the length of the band 1424. As the user applies force to the cover 1404 along the length of the band, it will cause the vibrating element 1600 to slide along the length of the opening 1432. For example, if the cavity 1500 is filled with padding around the vibrating element 1600, then the cover 1404 and the vibrating element 1600 may move as a single unit. If for some reason the vibrating element 1600 resists sliding, the user may use the zipper 1510 to access the cavity 1500 in which the vibrating element 1600 is disposed and apply force directly to the vibrating element 1600 (although, as mentioned, embodiments may preclude the user from easily accessing the cavity 1500). It will be understood that hook-and-loop fasteners 1518 and 1520 are exemplary only. Any number and/or type of fasteners may be used. In an embodiment, the cover 1404 may be permanently fastened to the band 1424. In such an embodiment, the vibrating element 1600 contained therein may also be stationary or may be moveable. Additional means of adjusting and/or customizing the band, such as means described elsewhere herein, may be provided.

Figure 39:
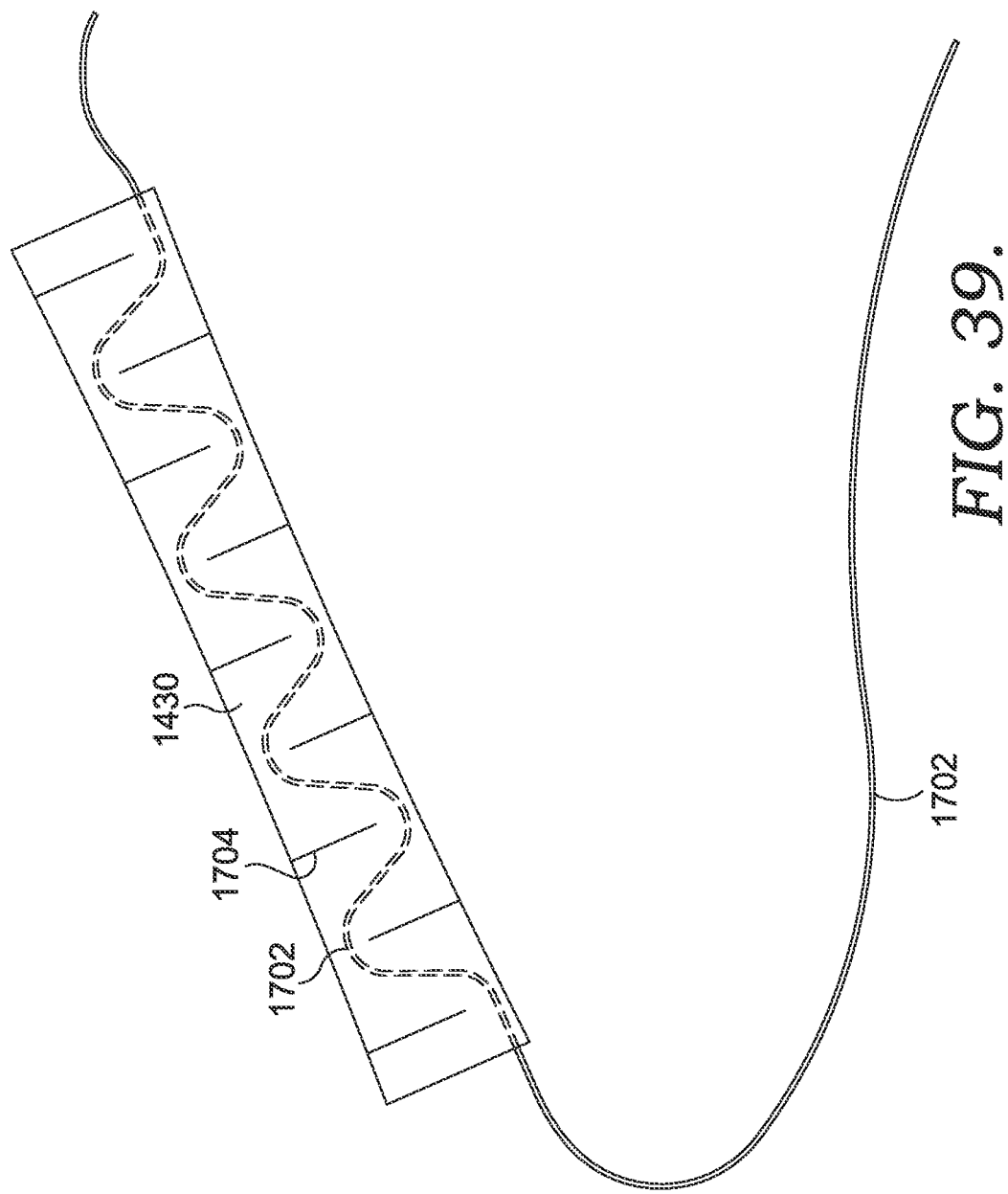
FIG. 39 is a plan view of a wire tunnel, in accordance with an exemplary embodiment hereof.

FIG. 39 illustrates additional details of the wire tunnel 1430. As shown, the wire tunnel 1430 includes one or more partitions, such as partition 1704. These partitions may be created by stitching, glue, or any other means. The partitions maintain the wire 1702 in a non-linear, curved formation, and in instances, the wire 1702 may resemble a substantially serpentine shape. This shape provides slack in the wire 1702 and thus facilitates movement of the covers and the vibrating elements along the length of the band 1424. This configuration also prevents the wires from getting stuck or tangled during use. The wire tunnels may be comprised of any number of materials. A wire tunnel comprising an elastic material may facilitate coughing during therapy.

Figure 40:
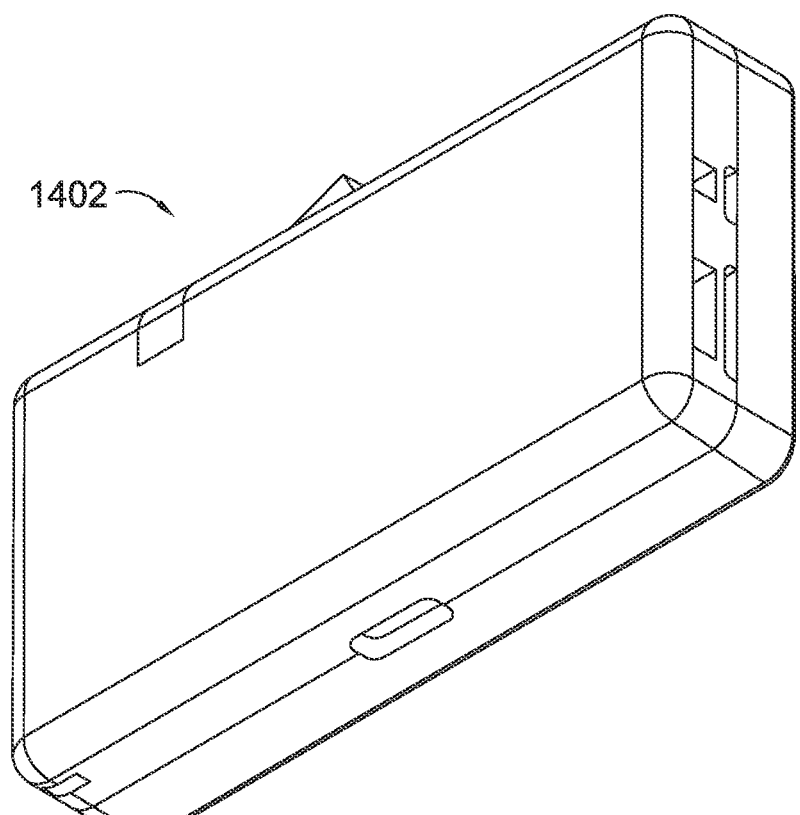
FIG. 40 is a perspective view of a controller enclosure, in accordance with exemplary embodiments hereof.

FIG. 40 depicts the controller enclosure 1402, which may house a controller and/or power source. The size of the controller may depend on the size of the battery and controller components housed therein. Control and user input features previously discussed herein may be incorporated into the controller. For example, the controller may be communicatively coupled to a mobile device application and/or a remote control. When multiple controllers are used in conjunction with one another, they may operate in a coordinated manner. For example, a mobile device application and/or remote may allow a user to select a number of controllers that are to be used, allow the user to pair each controller to the mobile device and/or remote, such as via a Bluetooth® connection, and enable the user to customize a percussive therapy session based on the user's particular needs. Additionally or alternatively, user input components may be provided on the controllers, themselves. The controllers may include a display screen that displays information regarding operational settings.

A mobile device application may run on a general purpose computing device (e.g., a user's personal mobile phone) and/or on a purpose-built device. In either instance, an application may identify each band (when the apparatus 1400 has multiple vibration bands) and each vibrating element with a unique address, such that each vibrating element may be controlled individually in terms of intensity and duration. In this way, the apparatus 1400 may operate in countless different states (with different vibrating elements operating in different manners). Additionally, because this configuration allows precision control over each vibrating element, the vibrating elements may operate precisely in unison, which may be beneficial for some users.

Figure 41A:
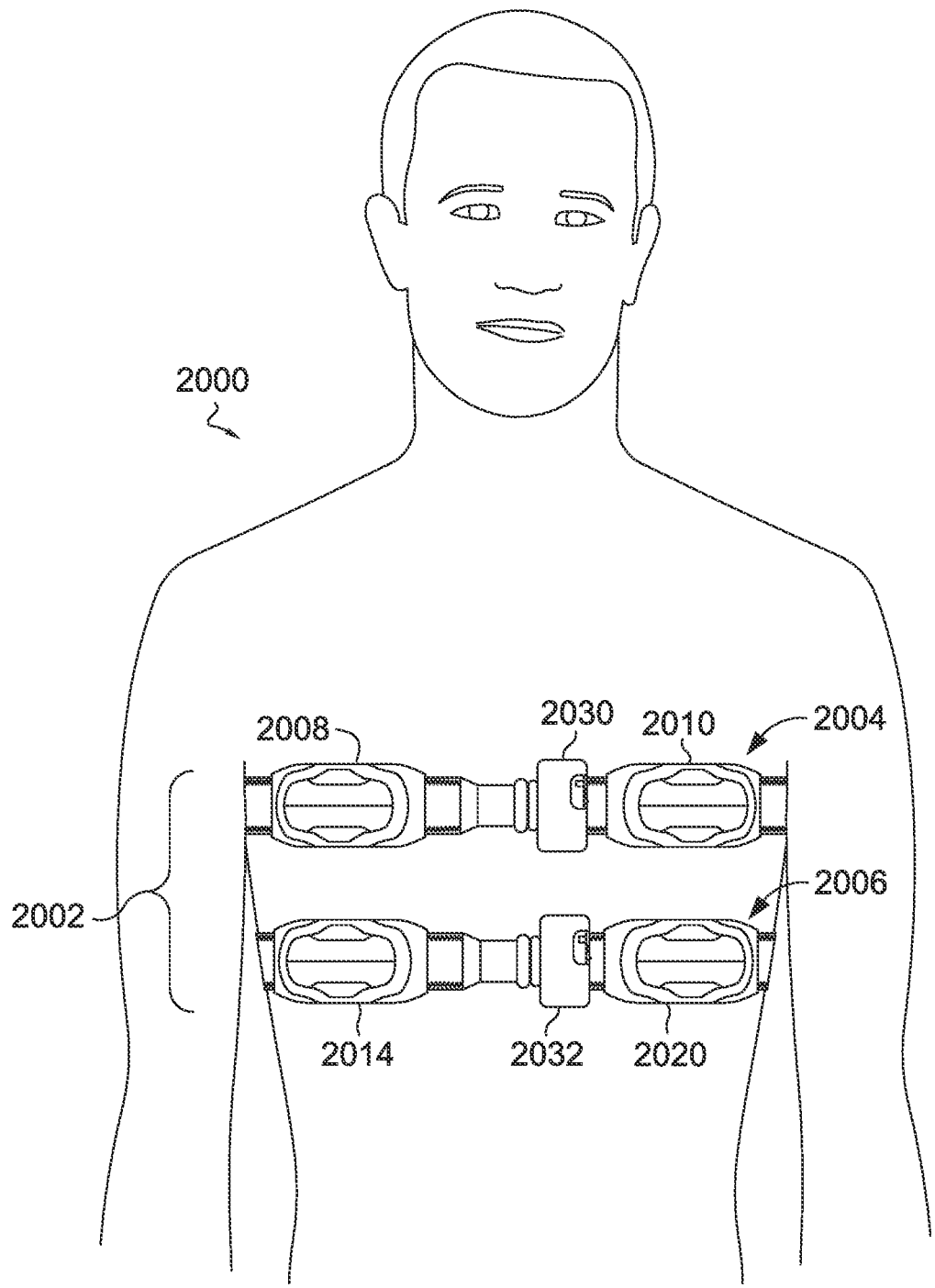
FIGS. 41A-B are front and rear views, respectively, of two vibration bands being worn by a user, in accordance with an exemplary embodiment hereof.
Figure 41B:
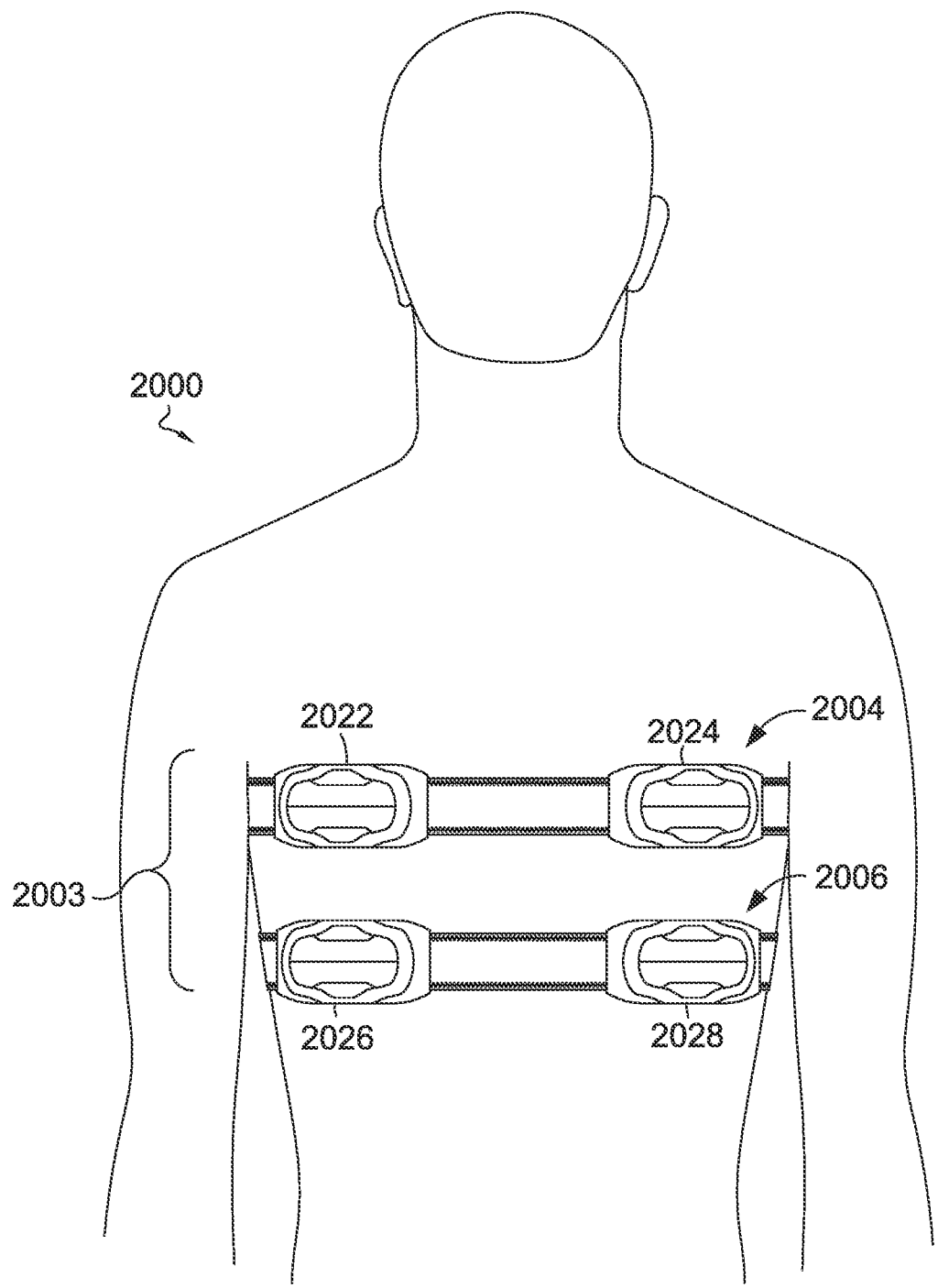
Figure 42A:
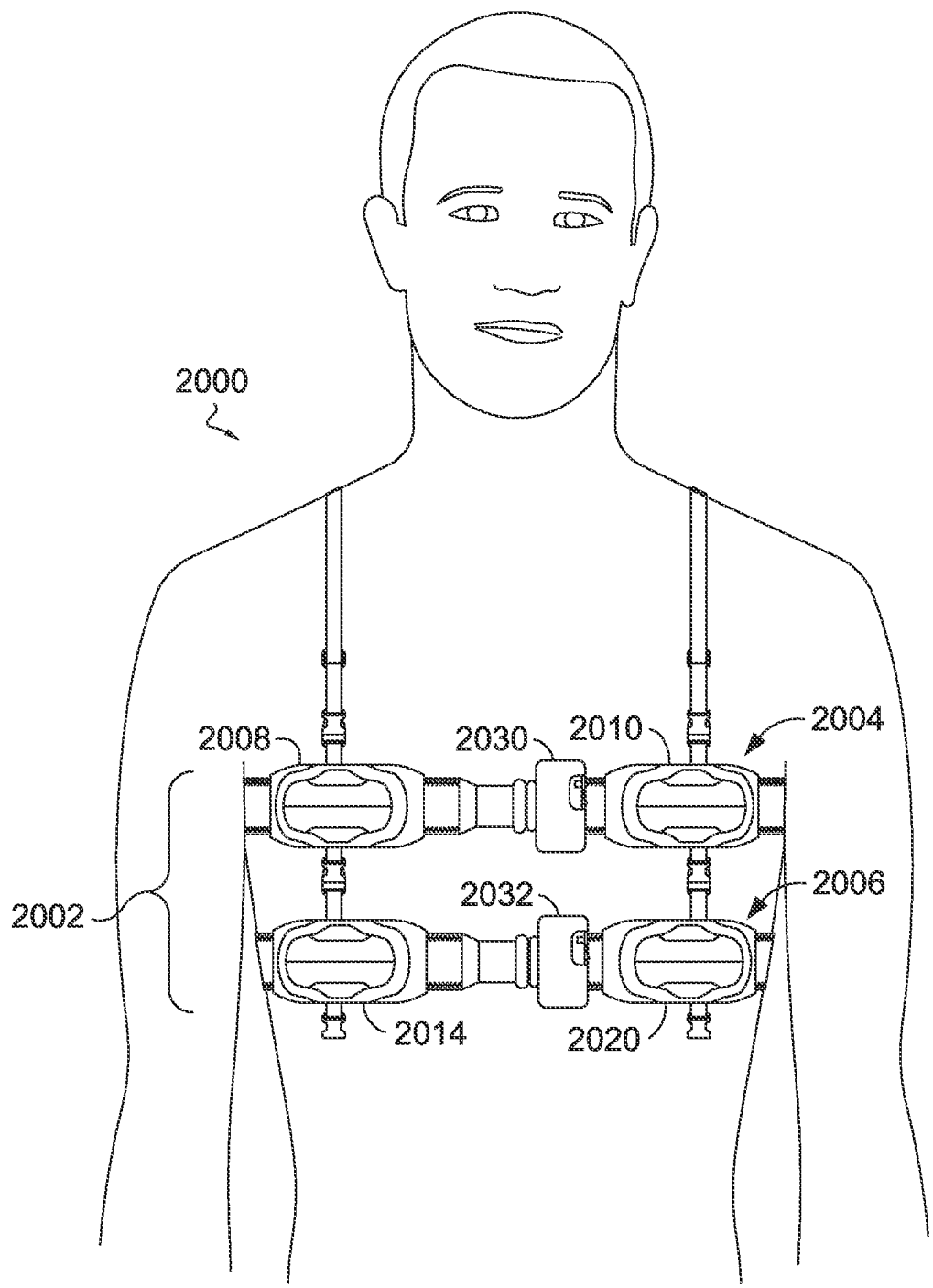
FIGS. 42A-B are front and rear views, respectively, of two vibration bands being worn by a user, in accordance with an exemplary embodiment hereof.
Figure 42B:
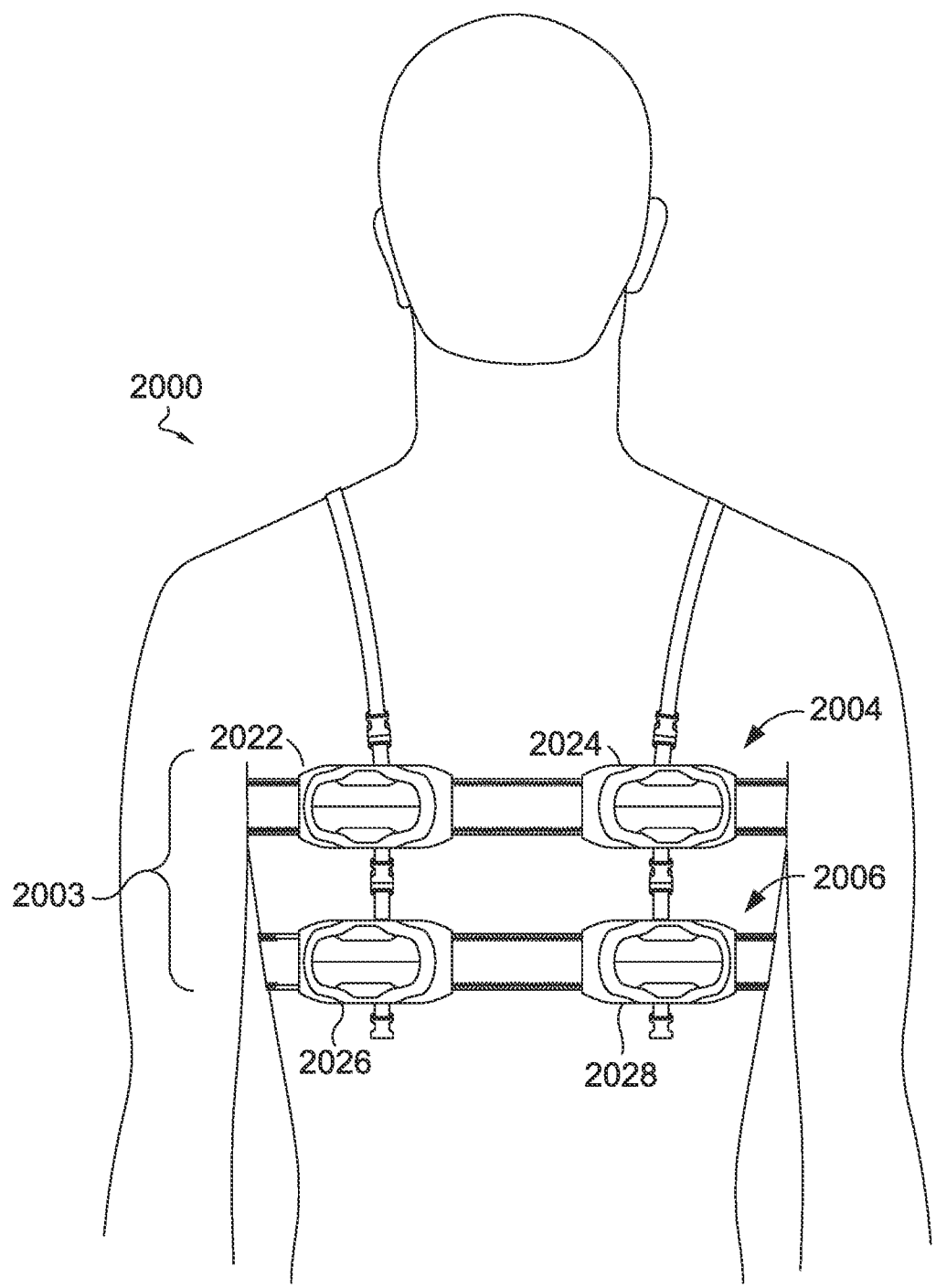

FIGS. 41A-B and 42A-B illustrate a user wearing an example apparatus 2000 for chest therapy. FIGS. 41A and 42A illustrate a front view of a user wearing the apparatus 2000 and FIGS. 41B and 42B illustrate a back view of the user wearing the apparatus 2000. The exemplary configuration in FIGS. 42A-B includes adjustable shoulder straps and releasable connection assemblies coupled to the plurality of moveable covers, either or both of which may maintain the apparatus 2000 in a desired location with respect to the user's body during use. Exemplary aspects of these features were discussed above (e.g., with respect to FIGS. 29A-B and 30A-B) and are not repeated here. In any of the illustrated configurations, the apparatus 2000 can be worn modularly (e.g., one vibration band may be used at a time). Additionally, the design of the apparatus 2000 leaves substantial portions of the user's body exposed. This may enhance comfort, and may also accommodate additional medical devices in the user's chest area. For example, a user may have a permanent drain in his or her lung. The apparatus 2000 can be positioned such that it does not interfere with that drain or cause discomfort in that area. The apparatus 2000 may be lightweight, with each band weighing approximately 1.5 to 2 pounds, and the entire apparatus weighing 3 to 4 pounds. Although not pictured, the apparatus 2000 may further include a carrying case designed to fit into a small backpack or briefcase.

As shown, the apparatus 2000 includes two vibration bands 2004 and 2006 (each of which may be similar to apparatus 1400) that have been wrapped around the chest area 2002 of the wearer's body. The vibration bands 2004 and 2006 may be used to provide percussive therapy at other portions of a user's body, as well. Each of vibration bands 2004 and 2006 may be sized according to the area of the body at which percussive therapy will be provided. Releasable connection assemblies, such as buckles, may be secured to the terminal ends of the vibration bands 2004 and 2006 in order to facilitate securing the vibration bands 2004 and 2006 around a user's body.

FIGS. 41A-B and 42A-B illustrate a one-to-one correspondence between the covers on the two vibration bands, but based on the modular design, this need not necessarily be the case. For example, one vibration band may include more covers (and vibrating elements) than another. It may be desirable to omit a particular cover if percussive therapy is not desired at a particular location on a user's body and/or if a cover at that particular location would impair the user's mobility.

As shown in FIGS. 41A and 42A, the vibration band 2004 has two moveable covers 2008 and 2010 positioned on the front chest area 2002 of the user. Similarly, the vibration band 2006 has two moveable covers 2014 and 2020 positioned on the front chest rest area 2002 of the user. The vibration bands 2004 and 2006 both continue around the sides of the torso and onto the back portion of the chest area 2003 shown in FIGS. 41B and 42B. Each of the two vibration bands 2004 and 2006 has two moveable covers on the back side of the torso area, as well. Vibration band 2004 includes moveable covers 2022 and 2024 and vibration band 2006 includes moveable covers 2026 and 2028. Each of the moveable covers 2008, 2010, 2014, and 2020 provide percussive therapy to the front chest area of the user while the moveable covers 2022, 2024, 2026, and 2028 provide percussive therapy to the back chest area 2003. Additionally, as shown in FIGS. 41A and 42A, releasable connection assemblies are used to secure the vibration bands around the user's torso. While the two vibration bands 2004 and 2006 are shown as being parallel to one another, it is contemplated that in other aspects, the vibration bands 2004 and 2006 may be in crisscross configuration, similar to the configuration described previously with regard to FIGS. 32A-B.

Two controller enclosures, 2030 and 2032 are also illustrated. These enclosures may house power and/or controller components. Each controller may receive input to control the on/off and type of percussive forces transmitted by the vibrating elements. While FIGS. 41A and 42A show each vibration band 2004 and 2006 as having a separate controllers, in additional configurations, a single controller may control the function of both bands. In embodiments, the vibration bands may be controlled manually or electronically via the use of an application on a user device (e.g., application on a mobile device).

It will be understood by those having skill in the relevant art that the features described herein with respect to various exemplary embodiments may be combined and/or interchanged. For example, the features described with respect to the exemplary apparatus 1400 may be combined and/or interchanged with the features described with respect to any combination of the exemplary band 100, exemplary band 600, exemplary vibration band 800, and/or exemplary unit 900. Accordingly, the exemplary embodiments discussed with respect to the figures herein are not intended to be mutually exclusive, but instead set forth various features that may be combined and incorporated into an apparatus for providing percussive therapy.

Figure 16:
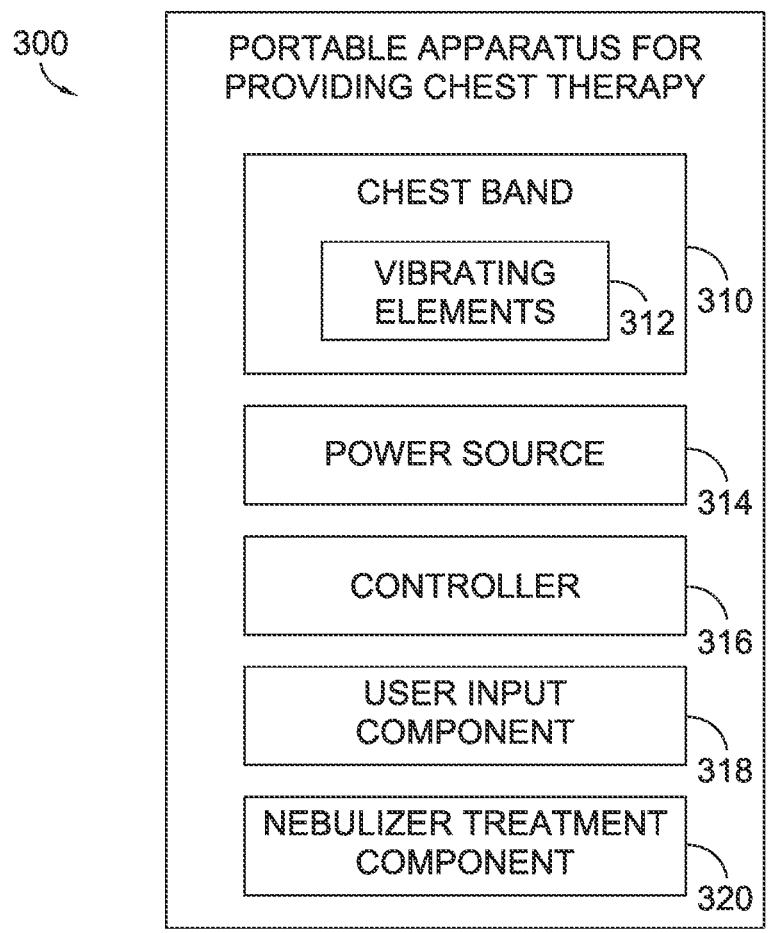
FIG. 16 is a block diagram showing exemplary components that may be included in an exemplary portable apparatus for providing chest physical therapy, in accordance with an exemplary embodiment hereof.

FIG. 16 provides a block diagram that shows exemplary components that may be included in an exemplary portable apparatus 300 for providing chest therapy. As previously discussed, the portable apparatus 300 may include a chest band (also referred to as a "vibration band" or a "band" herein) 310 having one or more vibrating elements 312. The portable apparatus 300 may further include a power supply 314 and a controller 316. A user input component 318 and a nebulizer treatment component 320 may also be included. As described above, the controller 316 may control the operation of the chest band 310 and the nebulizer treatment component 320 based on a user input received at the user input component 318. One or more of these components may be electrically and/or communicatively coupled to one another. It will be understood that the components illustrated in FIG. 16 are exemplary in nature and in number and should not be construed as limiting. Any number of components may be employed to achieve the functionality described herein. Components in addition to those illustrated in FIG. 16 may also be included within the apparatus 300 and are included within the scope hereof.

As described above, a portable apparatus for providing chest therapy to a user may include a controller that controls various operations of the apparatus. The controller may be, for example, a computing device, such as the exemplary computing device 400 of FIG. 17. Accordingly, embodiments of the invention may be described in the general context of computer code or machine useable instructions, including computer executable instructions, such as program modules, being executed by a computer or other machine. Generally, program modules including routines, programs, objects, components, data structures, etc., refer to code that performs particular tasks or implements particular abstract data types. Embodiments hereof may be practiced in a variety of system configurations, including hand held devices, consumer electronics, general purpose computers, more specialty computing devices, etc. Moreover, embodiments hereof may also be practiced in a distributed computing system where tasks are performed by separate or remote-processing devices that are linked through a communications network. Computing device 400 is but one example of a suitable operating environment and is not intended to suggest any limitation as to the scope of use or functionality of embodiments hereof. The computing device 400 should not be interpreted as having any dependency or requirement relating to any one component nor any combination of components illustrated.

Figure 17:
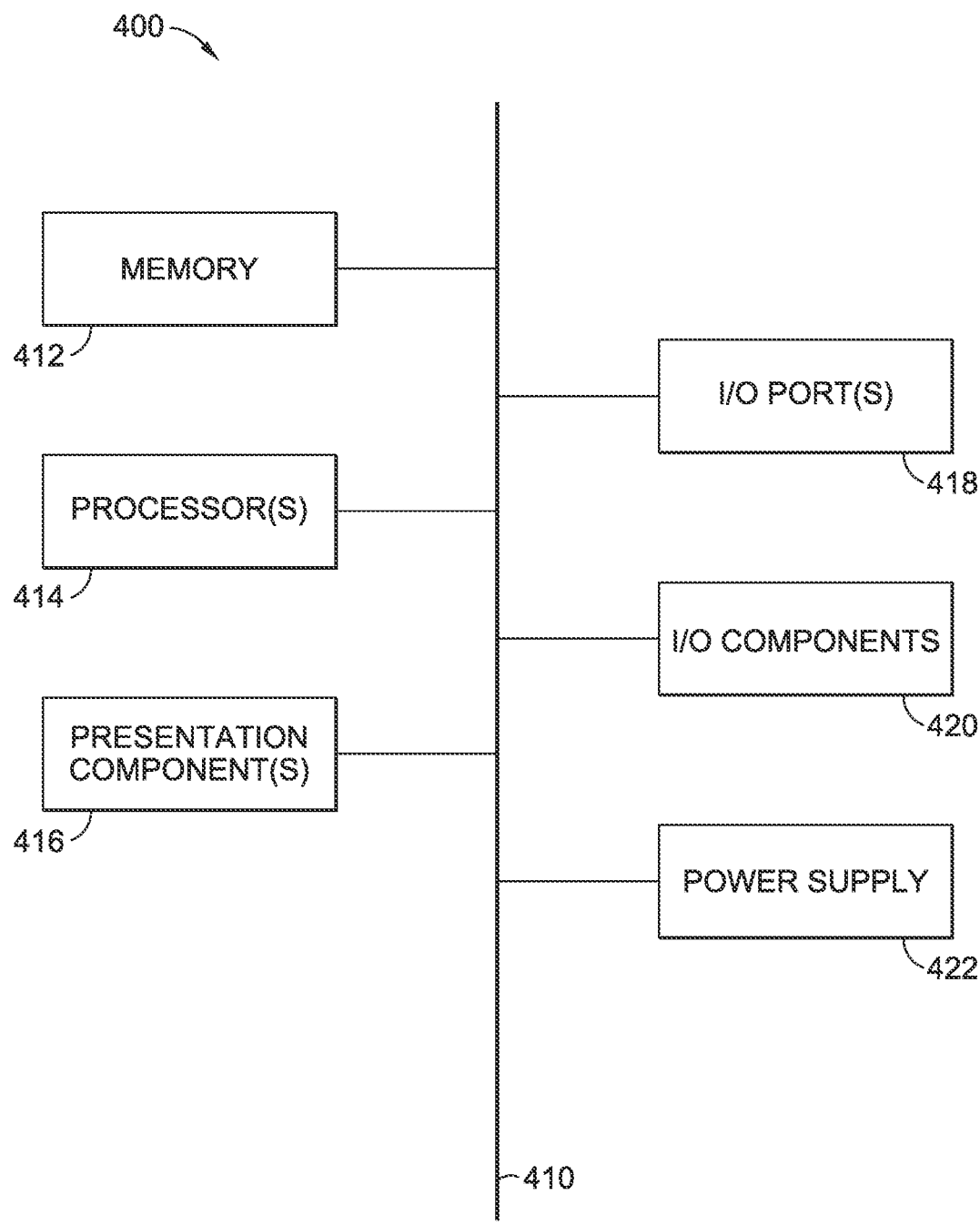
FIG. 17 is a block diagram of an exemplary computing device that may be used in conjunction with a portable apparatus for providing chest physical therapy, in accordance with an exemplary embodiment hereof.

As shown in the example of FIG. 17, the computing device 400 may have a bus 410 that directly or indirectly couples the following components: a memory 412, one or more processors 414, one or more presentation components 416, one or more input/output (I/O) ports 418, one or more I/O components 420, and an illustrative power supply 422. Bus 410 represents what may be one or more buses (such as an address bus, data bus, or combination thereof). Although the various components of FIG. 17 are shown with lines for the sake of clarity, in reality, delineating various components may not be so clear. For example, a presentation component, such as a display device, may be considered to be an I/O component. Additionally, processors may have memory.

The power supply 422 might include a rechargeable battery. For example, the power supply 422 may be a rechargeable battery that provides power to various components of a portable apparatus, including the vibrating elements, the nebulizer treatment component, and the controller, among others. As mentioned above, the rechargeable battery may be a lithium-ion battery of a desired voltage. As will be understood, the components of exemplary computing device 400 may be used in connection with one or more embodiments of the invention. In embodiments, computing device 400 may include fewer components than those depicted in FIG. 17, or other components in addition to those depicted in FIG. 17.

Computing device 400 typically may have a variety of non-transitory computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices, carrier wave or any other medium that can be used to encode desired information and be accessed by computing device 400.

Memory 412 may be comprised of tangible computer-storage media in the form of volatile and/or nonvolatile memory. Memory 412 may be removable, nonremovable, or a combination thereof. Exemplary hardware devices include solid-state memory, hard drives, optical-disc drives, etc.

Computing device 400 is depicted to have one or more processors 414 that read data from various entities such as memory 412 or I/O components 420. Exemplary data that is read by a processor may be comprised of computer code or machine-useable instructions, which may be computer-executable instructions such as program modules, being executed by a computer or other machine.

Presentation component(s) 416 may present data indications to a user or other device. Exemplary presentation components include a display device, speaker, printing component, vibrating component, light-emitting component, etc. I/O ports 418 allow computing device 400 to be logically coupled to other devices including I/O components 420, some of which may be built in.

In the context of embodiments hereof, the computing device 400 may be used to control various components included in a portable apparatus for providing chest therapy to a user. For example, the controller discussed above may include at least some of the components of computing device 400.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. An apparatus comprising:
    a first elongated band comprising a first terminal end, a second terminal end opposite the first terminal end, a top surface, a bottom surface opposite the top surface, and a plurality of openings extending through the top surface and the bottom surface of the first elongated band;
    a plurality of moveable vibrating elements coupled to the first elongated band at the plurality of openings of the first elongated band;
    a plurality of moveable covers coupled to the first elongated band, each of the plurality of moveable covers enclosing an internal cavity configured to receive one or more moveable vibrating elements of the plurality of moveable vibrating elements of the first elongated band;
    a releasable connection assembly comprising a first terminal-end connector coupled to the first terminal end and a second terminal-end connector coupled to the second terminal end of the first elongated band, wherein the second terminal-end connector is releasably connectable to the first terminal-end connector; and
    wherein each of the plurality of moveable vibrating elements comprises a motor moving a mass via a shaft that extends through an opening of the plurality of openings of the first elongated band.

2. The apparatus of claim 1, further comprising a wire tunnel comprising partitions, the partitions configured to maintain a wire in a substantially serpentine shape.

3. The apparatus of claim 2, wherein the first elongated band extends through openings in the plurality of moveable covers.

4. The apparatus of claim 1, wherein the releasable connection assembly comprises a stationary connector and an adjustable connector.

5. The apparatus of claim 4, wherein a controller is directly coupled to the releasable connection assembly.

6. The apparatus of claim 1, wherein the plurality of openings comprise elongated shapes that are configured to allow movement of the plurality of moveable vibrating elements along a length of the plurality of openings.

7. The apparatus of claim 1, wherein each of the plurality of moveable vibrating elements comprises:
    a motor housing that houses the motor and is adjacent to the top surface of the first elongated band;
    a mounting plate that is adjacent to the bottom surface of the first elongated band, wherein the mounting plate comprises a channel that is configured to receive the first elongated band, and wherein the mounting plate is coupled to the motor housing;
    the shaft that is coupled to the motor at a first terminal end of the shaft and that is coupled to the mass at a second terminal end of the shaft, wherein the shaft extends through the motor housing, the opening of the plurality of openings of the first elongated band, and the mounting plate.

8. The apparatus of claim 7, wherein each of the plurality of moveable vibrating elements further comprises a boot that is adjacent to the mass.

9. The apparatus of claim 1, further comprising:
    a second elongated band comprising a first terminal end, a second terminal end opposite the first terminal end, a top surface, a bottom surface opposite the top surface, and a plurality of openings extending through the top surface and the bottom surface of the second elongated band;
    a plurality of moveable vibrating elements coupled to the second elongated band at the plurality of openings of the second elongated band;
    a plurality of moveable covers coupled to the second elongated band, each of the plurality of moveable covers enclosing an internal cavity configured to receive one or more moveable vibrating elements of the plurality of moveable vibrating elements coupled to the second elongated band; and
    a releasable connection assembly comprising a first terminal-end connector coupled to the first terminal end and a second terminal-end connector coupled to the second terminal end of the second elongated band, wherein the second terminal-end connector is releasably connectable to the first terminal-end connector.

10. The apparatus of claim 9, wherein the first elongated band is releasably coupled to the second elongated band via one or more releasable connection assemblies coupled to one or more of the plurality of moveable covers.

11. The apparatus of claim 1, wherein each of the plurality of moveable covers comprises a closeable opening.

12. The apparatus of claim 1, wherein each of the plurality of moveable covers is coupled to the first elongated band via hook-and-loop fasteners.

13. The apparatus of claim 12, further comprising a plurality of wire tunnels enclosing wires that couple the plurality of moveable vibrating elements to a controller and a power source.

14. The apparatus of claim 13, wherein each of the plurality of wire tunnels comprises partitions configured to maintain a wire in a substantially serpentine shape.

15. An apparatus comprising:
    a band comprising a first terminal end, a second terminal end opposite the first terminal end, a top surface, a bottom surface opposite the top surface, and one or more openings disposed between the first terminal end and the second terminal end;
    one or more moveable vibrating elements coupled to the band at the one or more openings; and one or more moveable covers coupled to the band, each of the one or more moveable covers enclosing an internal cavity configured to receive a moveable vibrating element of the one or more moveable vibrating elements; and wherein each of the one or more moveable vibrating elements comprises a motor, a mass, and a shaft comprising a first terminal end and a second terminal end, wherein the shaft extends through an opening of the one or more openings, and wherein the motor is coupled to the first terminal end of the shaft and the mass is coupled to the second terminal end of the shaft.

16. The apparatus of claim 15, wherein each of the one or more openings comprises an elongated shape, and wherein a length of the elongated shape is greater than a width of the shaft.

17. The apparatus of claim 16, wherein a ratio of the length of the elongated shape to the width of the shaft is at least 5:1, and wherein a ratio of a width of the elongated shape to the width of the shaft is less than 2:1.

18. An apparatus comprising:

a first vibration band comprising:

a first elongated band comprising one or more elongated openings disposed along a length of the first elongated band, and one or more moveable vibrating elements coupled to the first elongated band at the one or more elongated openings of the first elongated band, wherein each of the one or more moveable vibrating elements comprises a motor moving a mass via a shaft that extends through an opening of the plurality of openings of the first elongated band; and a second vibration band comprising:

a second elongated band comprising one or more elongated openings disposed along a length of the second elongated band, and one or more moveable vibrating elements coupled to the second elongated band at the one or more elongated openings of the second elongated band, wherein each of the one or more moveable vibrating elements comprises a motor moving a mass via a shaft that extends through an opening of the plurality of openings of the second elongated band.

* * * * *